United States Patent
Chen et al.

(10) Patent No.: US 10,118,901 B2
(45) Date of Patent: Nov. 6, 2018

(54) THERAPEUTIC AGENTS

(71) Applicant: Purdue Pharmaceutical Products L.P., Stamford, CT (US)

(72) Inventors: Yu Chen, San Jose, CA (US); Yi Chen, Pleasanton, CA (US)

(73) Assignee: Purdue Pharmaceutical Products L.P., Stamford, CT (US)

( * ) Notice: Subject to any disclaimer, the term of this patent is extended or adjusted under 35 U.S.C. 154(b) by 599 days.

(21) Appl. No.: 14/374,995

(22) PCT Filed: Jan. 31, 2013

(86) PCT No.: PCT/EP2013/051944
§ 371 (c)(1),
(2) Date: Jul. 28, 2014

(87) PCT Pub. No.: WO2013/113838
PCT Pub. Date: Aug. 8, 2013

(65) Prior Publication Data
US 2015/0086551 A1    Mar. 26, 2015

(51) Int. Cl.
| | |
|---|---|
| C07D 235/04 | (2006.01) |
| C07D 235/08 | (2006.01) |
| A61K 39/00 | (2006.01) |
| C07D 235/30 | (2006.01) |
| C07D 235/14 | (2006.01) |
| A61K 45/06 | (2006.01) |
| A61K 31/4184 | (2006.01) |
| C07D 235/18 | (2006.01) |

(52) U.S. Cl.
CPC ........ *C07D 235/30* (2013.01); *A61K 31/4184* (2013.01); *A61K 45/06* (2013.01); *C07D 235/14* (2013.01); *C07D 235/18* (2013.01); *Y02A 50/414* (2018.01)

(58) Field of Classification Search
None
See application file for complete search history.

(56) References Cited

U.S. PATENT DOCUMENTS

| | | |
|---|---|---|
| 4,522,811 A | 6/1985 | Eppstein et al. |
| 5,134,127 A | 7/1992 | Stella et al. |
| 5,376,645 A | 12/1994 | Stella et al. |
| 5,571,534 A | 11/1996 | Jalonen et al. |
| 5,874,418 A | 2/1999 | Stella et al. |
| 6,046,177 A | 4/2000 | Stella et al. |
| 6,087,367 A | 7/2000 | Breslow et al. |
| 6,133,248 A | 10/2000 | Stella |
| 6,214,852 B1 | 4/2001 | Kim et al. |
| 6,407,079 B1 | 6/2002 | Muller et al. |
| 8,609,864 B2 | 12/2013 | Chen et al. |
| 8,962,855 B2 | 2/2015 | Chen et al. |
| 9,096,627 B2 | 8/2015 | Chen et al. |
| 9,376,395 B2 | 6/2016 | Chen et al. |
| RE46,144 E | 9/2016 | Chen et al. |
| 2002/0076409 A1 | 6/2002 | March et al. |
| 2006/0079528 A1 | 4/2006 | Finn et al. |
| 2006/0159713 A1* | 7/2006 | Brittain ................ A61K 9/0019 424/400 |
| 2008/0146556 A1 | 6/2008 | Diebold et al. |
| 2010/0022512 A1 | 1/2010 | Wisdom et al. |
| 2010/0216858 A1 | 8/2010 | Popek et al. |
| 2011/0190363 A1 | 8/2011 | Drager et al. |
| 2011/0269706 A1 | 11/2011 | Chen et al. |
| 2011/0311624 A1 | 12/2011 | Loury et al. |
| 2013/0209558 A1 | 8/2013 | Patzak et al. |
| 2015/0086551 A1 | 3/2015 | Chen et al. |
| 2017/0095482 A1 | 4/2017 | Mehrling |
| 2017/0151218 A1 | 6/2017 | Mehrling et al. |
| 2017/0189382 A1 | 7/2017 | Mehrling et al. |
| 2017/0296513 A1 | 10/2017 | Mehrling et al. |
| 2018/0098969 A1 | 4/2018 | Mehrling et al. |

FOREIGN PATENT DOCUMENTS

| | | |
|---|---|---|
| CL | 0501-2003 | 3/2003 |
| CL | 2272-2005 | 9/2005 |
| CL | 3232-2006 | 11/2006 |
| CN | 1764648 | 4/2006 |

(Continued)

OTHER PUBLICATIONS

Meanwell (J. Med. Chem, 2011, 54, 2529-2591).*
Vippagunta et al. "Crystalline Solids," Advanced Drug Delivery Reviews, 2001, 48, pp. 18.*
Braga et al.; Stuct. Bond. 2009, 132, 25-50.*
Barman Balfour and Goa, "Bendamustine," *Drugs*, 61(5):631-638 (2001).
Chow et al., "In vitro induction of apoptosis of neoplastic cells in low-grade non-Hodgkin's lymphomas using combinations of established cytotoxic drugs with bendamustine," *Haematologica*, 86:485-493 (2001).
Herold et al., "Bop Versus Cop in Advanced Low Grade Non-Hodgin's Lymphomas—Results of a Randomized Multicenter Study," *Blood*, 94(Suppl 1):262a (1999) (Abstract #4382).

(Continued)

*Primary Examiner* — Mark Halvorson
*Assistant Examiner* — Kauser M Akhoon
(74) *Attorney, Agent, or Firm* — McCarter & English, LLP; Yu Lu; Wei Song

(57) ABSTRACT

The present invention relates to a class of hydroxamic acid compounds of Formula (I), which act as alkylating agents and/or inhibitors of the HDAC pathway, having potential utility in the treatment of a neoplastic disease and immune diseases.

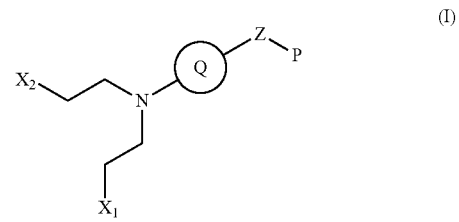

17 Claims, No Drawings

(56) References Cited

FOREIGN PATENT DOCUMENTS

| | | |
|---|---|---|
| CN | 101084876 A | 12/2007 |
| CN | 101928234 A | 12/2010 |
| CN | 102993102 A | 3/2013 |
| DE | 34727 A1 | 12/1964 |
| EP | 0717638 B1 | 3/2002 |
| JP | 2007-531793 A | 11/2007 |
| WO | 1995/030442 A1 | 11/1995 |
| WO | 2002/010161 A1 | 2/2002 |
| WO | 2002/022577 A2 | 3/2002 |
| WO | 2002/026696 A1 | 4/2002 |
| WO | 2004/076386 A2 | 9/2004 |
| WO | 2005/097747 A1 | 10/2005 |
| WO | 2006/120456 A1 | 11/2006 |
| WO | 2007/134169 A2 | 11/2007 |
| WO | WO-2008/050125 A1 | 5/2008 |
| WO | 2008/067027 A2 | 6/2008 |
| WO | 2009/036016 A1 | 3/2009 |
| WO | 2009/067453 A1 | 5/2009 |
| WO | 2009/100045 A1 | 8/2009 |
| WO | 2010/042568 A1 | 4/2010 |
| WO | 2010/075542 A1 | 7/2010 |
| WO | WO-2010/085377 A2 | 7/2010 |
| WO | 2010/097700 A1 | 9/2010 |
| WO | 2013/039488 A1 | 3/2013 |
| WO | 2013/040286 A2 | 3/2013 |
| WO | 2013/113838 A1 | 8/2013 |
| WO | 2015/085289 A1 | 6/2015 |
| WO | 2015/181154 A1 | 12/2015 |
| WO | 2015/181157 A1 | 12/2015 |
| WO | 2016/087950 A1 | 6/2016 |

OTHER PUBLICATIONS

Kollmannsberger et al., "Phase II study of bendamustine in patients with relapsed or cisplatin-refractory germ cell cancer," *Anticancer Drugs*, 11:535-539 (2000).
Minucci and Pelicci, "Histone deacetylase inhibitors and the promise of epigenetic (and more) treatments for cancer," *Nat. Rev. Cancer*, 6:38-51 (2006).
Poenisch et al., "Bendamustine/Prednisone Versus Melphalane/Prednisone in the Primary Treatment of Multiple Myeloma: An Updated Analysis of the 94BP01 Protocol," *Blood*, 96, Suppl 1:759a (2000) (Abstract #3284, Poster Board #Session: 748-111).
Anastasia, et al., Bendamustine for Hodgkin Lymphoma Patients Failing Autologous or Autologous and allogeneic Stem Cell Transpantation: A Retrospective Study of the Fondazione Italiana Linfomi; British Journal of Haematology, 166:140-153 (2014).
Bachmann et al., "Epigenetic silencing of BIM in glucocorticoid poor-responsive pediatric acute lymphoblastic leukemia, and its reversal by histone deacetylase inhibition," Blood, 116(16):3013-3022 (2010).
Barendsen et al Leukemia Research 14(5) 1990 pp. 467-474.
Botrugno, et al., "Molecular Pathways: Old Drugs Define New Pathways: Non-Histone Acetylation at the Crossroads of the DNA Damage Response and Autophagy," Clin. Cancer Res., 18:2436-42 (2012).
Brewster and Loftsson, "Cyclodextrins as pharmaceutical solubilizers," Adv. Drug Delivery Rev., 59:645-666 (2007).
Beatriz Aguado Bueno et al., "Preliminary Experience of the Spanish Compassionate Use Registry of Bendamustine in Patients with Relapsed and/or Refractory Multiple Myeloma," Blood, 120(21)[Abstract 4035] (2012).
Buglio D. et al., "Vorinostat inhibits STAT6-mediated TH2 cytokine and TARC production and induces cell death in Hodgkin lymphoma cell lines". Blood, vol. 112 (4):1424-1433, Aug. 15, 2008.
Cai et al., "Discovery of 7-(4-(3-Ethynylphenylamino)-7-methoxyquinazolin-6-yloxy)-N-hydroxyheptanamide (CUDC-101) as Potent Multi-Acting HDAC, EGFR, and HER2 Inhibitor for Treatment of Cancer," J. Med. Chem., 53:2000-2009 (2010).
Cai al., "Solubilization of vorinostat by cyclodextrins," J. Clin. Pharm. Thera., 35:521-526 (2010).
Cancer [online], [retrieved on Jul. 6, 2007] Retrieved from the Internet, URL: http://www.nlm.nih.gov/medlineplus/cancer.html.
Chen Li-Ping et al., "Dexamethasone and vorinostat cooperatively promote differentiation and apoptosis in Kasumi-1 leukemia cells through ubiquitination and degradation of AML1-ETO," Database Medline [online]—US National Library of Medicine (NLM), Bethesda, MD, US, XP002742548, Database Accession No. NLM24103869 [Abstract] (Sep. 2013).
Chamberlain et al Journal of Neuro Oncology 118(1) 2014 155-162.
Corazzelli, et al., "Efficacy and safety of bendamustine for the treatment of patients with recurring Hodgkin lymphoma," British Journal of Haematology, 60:207-215 (2013).
Deangelo et al Blood 108(12) 2006 3674-3681.
Mehrling, "Mundipharma EDO GmbH Announces FDA Investigational New Drug Approval of its First Anti-Cancer Compound, EDO-S101, for the Treatment of Patients with Relapsed/Refractory Haematologic Malignancies and Solid Tumours (http://mundipharma-edo.com/2015/07/31/mundipharma-edo-gmbh-announces-fda-investigational-new-drug-approval-of-its-first-anti-cancer-comound-deo-s101-for-the-treatment-of-patients-with-relapsedrefractory-haematologic-malignancies-and-s/)," EDO-S101 FDA IND Press Release—Basel, Switzerland, Jul. 31, 2015.
Enrique M. Ocio et al., "Triple Combinations of the HDAC Inhibitor Panobinostat (LBH589) + Dexamethasone with Either Lenalidomide or Bortezomib are Highly Effective in a Multiple Myeloma Mouse Model," Blood—Annual Meeting Abstracts, 110(11)(Part 1)(2007)[Abstract].
Filippi et al., "The First-in-Class Alkylating Histone-Deacetylase Inhibitor(HDACi) Fusion Molecule Edo-S101 Exerts Potent Preclinical Activity Against Tumor Cells of Hodgkin Lymphoma (HL) Including Bendamustine-Resistant Clones" ASH, 57th annual meeting and exposition, Dec. 2015, Abstract 2481.
Furumai et al. "Potent histone deacetylase inhibitors built from trichostatin A and cyclic tetrapeptide antibiotics including trapoxin," PNAS, 98(1):87-92 (2001).
Ghesquieres et al., "Clinical experience of bendamustine in relapsed or refractory Hodgkin lymphoma: a retrospective analysis of the French compassionate use program in 28 patients," Leukemia & Lymphoma, 54 (11):2399-2404 (2013).
Golub et al., "Molecular Classification of Cancer Class Discovery and Class Prediction by Gene Expression Monitoring," Science, 286:531-537 (1999).
Griffith et al., "A novel anti-cancer bifunctional platinum drug candidate with dual DNA binding and histone deacetylase inhibitory activity," Chem. Commun., 44:6735-6737 (2009).
Griffith et al., "Novel platinum pyridinehydroxamic acid complexes: synthesis, characterisation, X-ray crystallographic study of nitric oxide related properties," Polyhedron, 26:4697-4706 (2007).
Harrison S J et al: "High Response Rates with the Combination of Bortezomib. Dexamethasone and the Pan-HistoneDeacetylase Inhibitor Romidepsin in Patients with Relapsed or Refractory Multiple Myeloma in a Phase 1/11 Clinical Trial". Blood; ASH Annual Meeting Abstracts. Jan. 1, 2008 (Jan. 1, 2008). pp. 1-2.
Hedgethorne et al Drugs of the Future 35(11) 2010 pp. 893-902.
Herold et al Journal of Cancer Research and Clinin Oncol 2006 (132) pp. 105-112.
Hoffman et al., "Brentuximab Vedotin Plus Bendamustine Active in Heavily Pretreated Hodgkin Lymphoma, ALCL" Cancer Therapy Advisor, Dec. 7, 2015, Orlando FL [http://www.cancertherapyadvisor.com/ash-2015/hodgkin-lymphoma-alcl-brentuximab-vedotin-better-treatment-risk/article/458249/].
J. Han van Krieken, "New developments in the pathology of malignant lymphoma Areview of the literature published from Jan.-Apr. 2016" J Hematopathol (2016) 9:73-83.
Jonathan L Kaufman et al: "Lenalidomide, Bortezomib, and Dexamethasone (RVD) in Combination with Vorinostat As Front-Line Therapy for Patients with Multiple Myeloma (MM): Results of a Phase 1 Study," BLOOD, vol. 120, No. 21, Nov. 16, 2012 (Nov. 16, 2012). p. 336.
Kampa-Schittenhelm et al., "Quizartinib (AC220) is a potent second generation class III tyrosine kinase inhibitor that displays a distinct inhibition profile against mutant-FLT3, -PDGFRA and -KIT isoforms," Molecular Cancer, Biomed Central, London, GB, 12(1):1-15 [Abstract].

(56) References Cited

OTHER PUBLICATIONS

Keating et al., "Bendamustine," Nature Rev./Drug Disc., 7:473-474 (2008).
Knauf, "Bendamustine in the treatment of chronic lymphocytic leukemia," Exp. Rev. Anticancer Ther., 9(2):165-174 (2009).
Lala et al., Role of nitric oxide in tumor progression: Lessons from experimental tumors, Cancer and Metastasis Reviews (1998), 17,91-106.
Layman et al, Severe and prolonged lymphopenia observed in patients treated with bendamustine and erlotinib for metastatic triple negative breast cancer, Cancer Chemotherapy and Pharma 2013 (71) pp. 1183-1190.
Lentzsch, Blood, 119(20):46008-46113 (2012).
Leoni, "Bendamustine: Rescue of an Effective Antineoplastic Agent From the Mid-Twentieth Century," Semin Hematol., 48 Suppl 1:S4-11 (2011).
Leoni, et al., "Bendamustine (Treanda) Displays a Distinct Pattern of Cytotoxicity and Unique Mechanistic Features Compared with Other Alkylating Agents," Clin. Cancer Res., 14(1):309-17 (2008).
Liu et al., "A DNA/HDAC dual-targeting drug CY190602 with significantly enhanced anticancer potency," EMBO Mol. Med., 12 pages, Published online: Mar. 9, 2015.
Liu, "Characterization of TCL1-Tg:P53- / -Mice that Resemble Human Chronic Lymphocytic Leukemia with 17P-Deletion," UT GSBS Thesis, Graduate School of Biomedical Sciences, Digital Commons@The Texas Medical Center, May 2013.
Loftsson and Duchêne, "Cyclodextrins and their pharmaceutical applications," Intl. J. Pharmaceutics, 329:1-11 (2007).
Lopez-Iglesias et al., "Preclinical anti-myeloma activity of the alkylating-HDACi molecule EDO-S101 through DNA-damaging and HDACi effects," Poster, Jun. 1, 2014 (http://mundipharma-edo.com/2014/06/01/preclinical-anti-myeloma-activity-of-the-allcylating-hdaci-molecule-edo-s101-through-dna-damaging-and-hdaci-effects/)[Abstract].
Ludwig et al., "Dexamethasone is an active and well-tolerated regimen in patients with relapsed or refractory multiple myeloma," Blood, 123(7):985-991 (2014).
Marks, "Discovery and development of SAHA as an anticancer agent," Oncogene, 26:1351-1356 (2007).
Marmion et al., "Hydroxamic Acids—An Intriguing Family of Enzyme Inhibitors and Biomedical Ligands," Eur. J. Inorg. Chem., 2004(15):3003-3016 (2004).
Mehrling, "The Alkylating-HDAC Inhibition Fusion Principle: Taking Chemotherapy to the Next Level with the First in Class Molecule EDO-S101," Anti-Cancer Agents in Medicinal Chemistry, 2016, 16:20-28.
Mehrling, Mundipharma EDO GmbH announces first-in-human clinical trial of its lead compound, EDO-S101 (http://mundipharma-edo.com/2016/07/20/mundipharma-edo-gmbh-announces-first-in-human-clinical-trial-of-lead-compound-edo-s101/)—First-in-human clinical trial of its lead compound, EDO-S101, Switzerland, May 31, 2016, p. 1-2.
Mehrling, Chemotherapy is getting 'smarter', Future Oncol.—Editorial, 11(4):549-552 (2015).
Miller et al., "Histone Deacetylase Inhibitors," J. Med. Chem., 46(24):5097-5116 (2003).
Moosman et al Leukemia & Lymphoma 51(1) 2010 149-152.
Moradei et al., "Histone Deacetylase Inhibitors: Latest Developments, Trends and Prospects," Curr. Med. Chem.—Anti-Cancer Agents, 5:529-560 (2005).
Moskowitz, et al., "Bendamustine: a bridge to longer term solutions in heavily treated hodgkin lymphoma," Leukemia & Lymphoma, 54(11):2339-2340 (Nov. 2013).
Moskowitz A.J. et al., "Phase II study of Bendamustine in relapsed and refractory Hodgkin lymphoma", J.Clin. Oncol. Feb. 1, 2013; 31(4):456-60.
Munker et al Blood 110(11) part 2 2007 274B Abstract No. 4804.
Offidani et al Blood Cancer Journal 3 2013 e162.
Paris et al., "Histone Deacetylase Inhibitors: From Bench to Clinic," J. Med. Chem., 51(6):1505-1529 (2008).
Philippe Moreau et al., "Phase 1 b Dose Escalation Study of Oral fluisinostat, a Histone Deacetylase Inhibitor (HDACi), In Combination With Velcade (Bortezomib) and Dexamethasone for Patients With Relapsed Multiple Myeloma (MM)," Blood, vol. 122, No. 21, Nov. 15, 2013 [Abstract].
Pitha et al., "Parenteral hydroxypropyl cyclodextrins: intravenous and intracerebral administration of lipophiles," J. Pharm. Sci., 83(6):833-837 (1994).
Ponisch et al Journal of Cancer Research and Clin Oncol (2006) 132; 205-212.
Ponisch et al Journal of Cancer Research and Clin Oncol (2013) 139;499-508.
Pulsoni et al. "Bendamustine for Hodgkin lymphoma patients failing autologous or autologous and allogeneic stem cell transplantation: a retrospective study of the Fondazione Italiana Linfomi" British Journal of Haematology, 2014, 166, 140-153.
Rajewski et al., "Preliminary safety evaluation of parenterally administered sulfoalkyl ether ?-cyclodextrin derivatives," J. Pharm. Sci., 84(8):927-932 (1995).
Rasheed et al Expert Opinion on Investigational Drugs 2007 16(5) pp. 659-678.
Rosaria De Filippi et al., The First-in-Class Alkylating Histone-Deacetylase Inhibitor (HDACi) Fusion Molecule Edo-S101 Exerts Potent Preclinical Activity Against Tumor Cells of Hodgkin Lymphoma (HL) Including Bendamustine-Resistant Clones; 57th Annual Meeting & Exposition, Orlando, FL—Dec. 5-8, 2015 [Downloaded from: https://ash.confex.com/ash/2015/webprogram/Paper84797.html].
Sanchez et al., "Anti-Myeloma Effects of Cartilzomib with Cyclophosphamide (CY) or Bendamustine (Ben)," Blood, 120(21)[Abstract] (2012).
Saulnier et al., "An efficient method for the synthesis of guanidino prodrugs," Bioorganic and Medicinal Chemistry Letters, 4:1985-1990 (1994).
Sawas A. et al., "The combination of brentuximab vedotin (Bv) and bendamustine (B) demonstrates marked activity in heavily treated patients with relapsed or refractory Hodgkin lymphoma (HL) and anaplastic large T-cell lymphoma (ALCL): Results of an international multi center phase I/II experience". Oral presentation at 57th American Society of Hematology (ASH9 Annual Meeting & Exposition; Dec. 5-8, 2015; Orlando, FL.<http://www.bloodjournal.org/content/126/23/586?sso-checked=true>.
Shipley et al.; "Acute Myelogenous Leukemia," Experimental Hematology, 37:649-658 (2009).
Sturn A. et al., "Genesis: cluster analysis of microarray data," Bioinformatics, 18(1):207-8 (2002).
Vyas et al., "Cyclodextrin based novel drug delivery systems," J. Incl. Phenom. Macrocycl. Chem., 62:23-42 (2008).
Wang et al Leukemia and Lymphoma 53(8) 2012 pp. 1543-1551.
Wang et al., "Effect of histone deacetylase inhibitor NL101 on rat neurons" XP002740556 Database Medline accession No. NLM24998648 ZheJiang Hua Xue Xue Bao, Yi xue ban 43 (3) May 2014, pp. 265-272 Abstract.
Wang et al., "Toward Selective Histone Deacetylase Inhibitor Design: Homology Modeling, Docking Studies, and Molecular Dynamics Simulations of Human Class 1 Histone Deacetylases," J. Med. Chem., 48:6936-6947 (2005).
Wyndham H. Wilson, Relationship of p53, bcl-2, and Tumor Proliferation to Clinical Drug Resistance in Non-Hodgkin's Lymphomas, Blood, vol. 89, No. 2 Jan. 15, 1997: p. 601-609.
Xie et al. "Quantitative Structure-Activity Relationship Study of Histone Deacetylase Inhibitors," Curr. Med. Chem.—Anti-Cancer Agents, 4:273-299 (2004).
Yan et al., "Abstract 2741: Synergistic Inhibition of Tumor Growth and Overcoming Chemo-resistance by simultaneously targeting key components in DNA damage/respair, epigenetic, and putative cancer stem cell signaling pathways using novel dual-functional DNA-alkylating/HDAC inhibitor and tumor suppressor gene nano," Cancer Research, 72(8)(Supplement)[Abstract], pp. 2741 (Apr. 15, 2012).
Zulkowski et al Journal of Cancer Research and Clinical Oncology 128 2002 111-113.

(56) References Cited

OTHER PUBLICATIONS

ClinicalTrials.gov, "A Phase 1 Study to Investigate the Safety, Pharmacokinetic Profiles and the Efficacy of EDO-S101, a First-in-Class Alkylating Histone Deacetylase Inhibition (HDACi) Fusion Molecule, in Relapsed/Refractory Hematologic Malignancies," Clinical Trials Identifier: NCT02576496 (Oct. 14, 2015)[Downloaded from: https://clinicaltrials.gov/archive/NCT02576496/2015_10_14].

Kalsi et al., The impact of low-grade toxicity in older people with cancer undergoing chemotherapy. Br J Cancer. Dec. 9, 2014;111(12):2224-8.

Khot et al., Panobinostat in lymphoid and myeloid malignancies. Expert Opin Investig Drugs. Sep. 2013;22(9):1211-23.

Kigawa J. New strategy for overcoming resistance to chemotherapy of ovarian cancer. Yonago Acta Med. Jun. 2013;56 (2):43-50.

Kim et al., Histone deacetylase inhibitors: molecular mechanisms of action and clinical trials as anti-cancer drugs. Am J Transl Res. Feb. 2011;3(2):166-79.

Knittel et al., Two mouse models reveal an actionable PARP1 dependence in aggressive chronic lymphocytic leukemia. Nat Commun. Jul. 28, 2017;8(1):153. 13 pages.

Kraus et al., EDO-S101, A New Alkylating Histone-Deacetylase Inhibitor (HDAC) Fusion Molecule has Superior Activity Against Myeloma and B Cell Lympoma and Strong Synergy, With Proteasome Inhibitors in vitro. ASH, 2014.

Kraus et al., EDO-S101, A New Alkylating Histone-Deacetylase Inhibitor (HDACi) Fusion Molecule, has Superior Activity Against Myeloma and B Cell Lympoma and Strong Synergy With Proteasome Inhibitors in vitro. ASH, 2014. Publication No. 2249.

Kraus et al., EDO-S101, A New Alkylating Histone-Deacetylase Inhibitor (HDACi) Fusion Molecule, Has Superior Activity Against Myeloma and B Cell Lympoma and Strong Synergy with Proteasome Inhibitors in vitro. Blood. 2014;124;2249.

Le Moigne et al., The p97 Inhibitor CB-5083 Is a Unique Disrupter of Protein Homeostasis in Models of Multiple Myeloma. Molecular Cancer Therapeutics. Nov. 2017;16(11):2375-2386.

Leung-Hagesteijn et al., Xbp1s-negative tumor B cells and preplasmablasts mediate therapeutic proteasome inhibitor resistance in multiple myeloma. Cancer Cell. Sep. 9, 2013;24(3):289-304.

Liby et al., Elevated and Deregulated Expression of HDAC3 in Human Astrocytic Glial Tumours. Folia Biologica (Praha). 2006;52:21-33.

Lin et al., Anti-rheumatic activities of histone deacetylase (HDAC) inhibitors in vivo in collagen-induced arthritis in rodents. Br J Pharmacol. Apr. 2007;150(7):862-72.

Lin et al., Treatment of Brain Metastases. J Clin Oncol. Oct. 20, 2015;33(30):3475-84.

Little et al., Experimental autoimmune vasculitis: an animal model of anti-neutrophil cytoplasmic autoantibody- associated systemic vasculitis. Am J Pathol. Apr. 2009;174(4):1212-20.

Little et al., Therapeutic effect of anti-TNF-alpha antibodies in an experimental model of anti-neutrophil cytoplasm antibody-associated systemic vasculitis. J Am Sac Nephrol. Jan. 2006;17(1):160-9.

Lombardi et al., Predictors of survival and effect of short (40 Gy) or standard-course (60 Gy) irradiation plus concomitant temozolomide in elderly patients with glioblastoma: a multicenter retrospective study of AINO (Italian Association of Neuro-Oncology). J Neurooncol. Nov. 2015;125(2):359-67.

Lopez-Iglesias et al., Preclinical anti-myeloma activity of EDO-S101, a new bendamustine-derived molecule with added HDACi activity, through potent DNA damage induction and impairment of DNA repair. J Hematol Oncol. Jun. 20, 2017;10(1):127. 14 pages.

Lopez-Iglesias et al., Preclinical Anti-Myeloma Activity of the Alkylating-HDACi Molecule EDO-S101 Through DNA-Damaging and HDACi Effects. EHA 2014 Poster, Jun. 12, 2014.

Lopez-Iglesias et al., Preclinical antimyeloma activity of EDO-S101 (bendamustine-vorinostat fusion molecule) through DNA-damaging and HDACi effects. 15th International Myeloma Workshop. Sep. 23-26, 2015. Rome, Italy. Clinical Lymphoma, Myeloma & Leukemia. Sep. 2015;15(3 Suppl. 3):e218, Abstract P0-238.

Lopez-Iglesias et al., The Alkylating Histone Deacetylase Inhibitor Fusion Molecule Edo-S101 Displays Full Bi-Functional Properties in Preclinical Models of Hematological Malignancies. Blood. 2014;124:2100.

Lopez-Iglesias et al., The Hybrid Molecule, Edo-S101, Impairs Double Strand Breaks Repair in Multiple Myeloma and Synergizes with Bortezomib and Dexamethasone. Blood. 2015;126(23):5354-5354.

Lucio-Eterovic et al., Differential expression of 12 histone deacetylase (HDAC) genes in astrocytomas and normal brain tissue: class II and IV are hypoexpressed in glioblastomas. BMC Cancer. Aug. 19, 2008;8:243.

Marchion et al., Development of histone deacetylase inhibitors for cancer treatment. Expert Rev Anticancer Ther. Apr. 2007;7(4):583-98.

McInnis et al., Dysregulation of autoantigen genes in ANCA-associated vasculitis involves alternative transcripts and new protein synthesis. J Am Soc Nephrol. Feb. 2015;26(2):390-9.

Medline/NLM AN: NLM24998648, 1 page.

Mehrling et al., Activity of the alkylating histone-deacetylase inhibition fusion molecule EDO-S-101 in preclinical models of human glioblastoma independent from MGMT expression. Journal of Clinical Oncology. May 29, 2017;33(Suppl. 15), Abstract e13031.

Mehrling et al., Is there hope to treat glioblastoma effectively? CNS Oncol. 2015;4(6):377-9.

Mehrling, Fusion Therapy, a New Approach to Combining Treatments. Drug Discovery World. 2016;71-76.

Mey et al., Bendamustine, lenalidomide and dexamethasone (BRd) has high activity as 2(nd)-line therapy for relapsed and refractory multiple myeloma—a phase II trial. Br J Haematol. Mar. 2017;176(5):770-782.

MRF, Melanoma Research Foundation, Melanoma Central Nervous System Metastases, Current Approaches, Challenges and Opportunities. 5 pages (2015).

O'Donnell et al., Cancer pharmacoethnicity: ethnic differences in susceptibility to the effects of chemotherapy. Clin Cancer Res. Aug. 1, 2009;15(15):4806-14.

O'Reilly et al., Urinary Soluble CD163 in Active Renal Vasculitis. J Am Soc Nephrol. Sep. 2016;27(9):2906-16.

Oken et al., Toxicity and response criteria of the Eastern Cooperative Oncology Group. Am J Clin Oncol. Dec. 1982;5 (6):649-55.

Oriol et al., Outcome after relapse of acute lymphoblastic leukemia in adult patients included in four consecutive risk-adapted trials by the PETHEMA Study Group. Haematologica. Apr. 2010;95(4):589-596.

Phan et al., An update on ethnic differences in drug metabolism and toxicity from anti-cancer drugs. Expert Opin Drug Metab Toxicol. Nov. 2011;7(11):1395-410.

Puetzer et al., Towards novel strategies of targeting specific vulnerabilities of T-PLL cells. AACR Annual Meeting. Jul. 2017;77(Suppl 13), Abstract 1372.

Rasschaert et al., A phase I study of bendamustine hydrochloride administered day 1+2 every 3 weeks in patients with solid tumours. Br J Cancer. Jun. 2007 4;96(11):1692-8.

Rasschaert et al., A phase I study of bendamustine hydrochloride administered once every 3 weeks in patients with solid tumors. Anticancer Drugs. Jun. 2007;18(5):587-95.

Rengstl et al., Small and big Hodgkin-Reed-Sternberg cells of Hodgkin lymphoma cell lines L-428 and L-1236 lack consistent differences in gene expression profiles and are capable to reconstitute each other. PLoS One. May 15, 2017;12(5):e0177378.

Rodriguez-Tenreiro y Sanchez, Hydrogels of Cyclodextrin Co-crosslinked and Interpenetrated for Controlled Drug Release. University of Santiago de Compostela, School of Pharmacy. pp. 29-32, (2006).

Santacruz et al., The prognostic impact of minimal residual disease in patients with chronic lymphocytic leukemia requiring first-line therapy. Haematologica. May 2014;99(5):873-80.

Sarkaria et al., Mechanisms of chemoresistance to alkylating agents in malignant glioma. Clin Cancer Res. May 15, 2008;14(10):2900-8.

(56) References Cited

OTHER PUBLICATIONS

Schöffski et al., Repeated administration of short infusions of bendamustine: a phase I study in patients with advanced progressive solid tumours. J Cancer Res Clin Oncol. Jan. 2000;126(1):41-7.
Schöffski et al., Weekly administration of bendamustine: a phase I study in patients with advanced progressive solid tumours. Ann Oncol. Jun. 2000;11(6):729-34.
Shah et al., Comprehensive analysis of MGMT promoter methylation: correlation with MGMT expression and clinical response in GBM. PLoS One. Jan. 7, 2011;6(1):e16146.
Simon, Optimal two-stage designs for phase Ii clinical trials. Control Clin Trials. Mar. 1989;10(1):1-10.
Song et al., Increased expression of histone deacetylase 2 is found in human gastric cancer. APMIS. 2005;113:264-8.
Stiborová et al., The synergistic effects of DNA-targeted chemotherapeutics and histone deacetylase inhibitors as therapeutic strategies for cancer treatment. Curr Med Chem. 2012;19(25):4218-38.
Storer, Design and analysis of phase I clinical trials. Biometrics. Sep. 1989;45(3):925-37.
Tesar et al., Limitations of standard immunosuppressive treatment in ANCA-associated vasculitis and lupus nephritis. Nephron Clin Pract. 2014;128(3-4):205-15.
Thurn et al., Rational therapeutic combinations with histone deacetylase inhibitors for the treatment of cancer. Future Oncol. Feb. 2011;7(2):263-83.
Trivedi et al., Management of Chemotherapy-Induced Peripheral Neuropathy. American Journal of Hematology / Oncology. Jan. 2015;11(1):4-10.
Valdez et al., Synergistic cytotoxicity of the DNA alkylating agent busulfan, nucleoside analogs and suberoylanilide hydroxamic acid in lymphoma cell lines. Leuk Lymphoma. May 2012;53(5):973-81.
Viel et al., Optimizing glioblastoma temozolomide chemotherapy employing lentiviral-based anti-MGMT shRNA technology. Mol Ther. Mar. 2013;21(3):570-9.
Vlachostergios et al., Bortezomib overcomes MGMT-related resistance of glioblastoma cell lines to temozolomide in a schedule-dependent manner. Invest New Drugs. Oct. 2013;31(5):1169-81.
von Tresckow et al., An update on emerging drugs for Hodgkin lymphoma. Expert Opin Emerg Drugs. Jun. 2014;19 (2):215-24.
Wang et al., Independent validation of a model using cell line chemosensitivity to predict response to therapy. J Natl Cancer Inst. Sep. 4, 2013;105(17):1284-91.
Weil et al., Breast cancer metastasis to the central nervous system. Am J Pathol. Oct. 2005;167(4):913-20.
Wilson et al., Histone deacetylase 3 (HDAC3) and other class I HDACs regulate colon cell maturation and p21 expression and are deregulated in human colon cancer. J Biol Chem. May 12, 2006;281(19):13548-58.
Witzel et al., Long-term tumor remission under trastuzumab treatment for HER2 positive metastatic breast cancer—results from the HER-OS patient registry. BMC Cancer. Nov. 4, 2014;14:806. 7 pages.
Xiao et al., Antineutrophil cytoplasmic autoantibodies specific for myeloperoxidase cause glomerulonephritis and vasculitis in mice. J Clin Invest. Oct. 2002;110(7):955-63.
Yardley, Drug resistance and the role of combination chemotherapy in improving patient outcomes. Int J Breast Cancer. 2013;2013:137414. 15 pages.
Zhu et al., Histone deacetylase 3 implicated in the pathogenesis of children glioma by promoting glioma cell proliferation and migration. Brain Res Jul. 3, 2013;1520:15-22.
Zinzani et al., Brentuximab Vedotin in Transplant-Naïve Relapsed/Refractory Hodgkin Lymphoma: Experience in 30 Patients. Oncologist. Dec. 2015;20(12):1413-6.
U.S. Appl. No. 13/143,155, filed Jul. 1, 2011, U.S. Pat. No. 8,609,864.
U.S. Appl. No. 14/075,145, filed Nov. 8, 2013, U.S. Pat. No. 9,096,627.
U.S. Appl. No. 14/972,750, filed Dec. 17, 2015, RE46,144.

U.S. Appl. No. 14/345,562, filed Nov. 3, 2014, U.S. Pat. No. 9,376,395.
U.S. Appl. No. 15/290,546, filed Oct. 11, 2016.
U.S. Appl. No. 15/314,162, filed Nov. 28, 2016, 2017-0151218.
U.S. Appl. No. 15/314,167, filed Nov. 28, 2016, 2017-0095482.
U.S. Appl. No. 15/314,172, filed Nov. 28, 2016, 2017-0189382.
U.S. Appl. No. 15/314,180, filed Nov. 28, 2016, 2017-0296513.
Advanced Accelerator Applications, Ongoing Clinical Studies with Advanced Accelerator Applications Pipeline Candidates. Retrieved online at: http://www.adacap.com/research-development/clinical-trials/. 6 pages.
Al-Ani et al., Changes in urinary metabolomic profile during relapsing renal vasculitis. Sci Rep. Dec. 1, 2016;6:38074. 11 pages.
Alfarouk et al., Resistance to cancer chemotherapy: failure in drug response from ADME to P-gp. Cancer Cell Int. Jul. 15, 2015;15:71.
American Cancer Society, How does chemotherapy affect the risk of second cancers? Retrieved online at: https://www.cancer.org/treatment/treatments-and-side-effects/physical-side-effects/second-cancers-in-adults/chemotherapy.html. 5 pages (2017).
Andersson et al., Discovery of novel drug sensitivities in T-PLL by high-throughput ex vivo drug testing and mutation profiling. Leukemia. Aug. 14, 2017. pp. 1-14.
Attal et al., Lenalidomide, Bortezomib, and Dexamethasone with Transplantation for Myeloma. The New England Journal of Medicine. Apr. 6, 2017;376:1311-1320.
Bernhard et al., Quality of life and quality-adjusted survival (Q-TWiST) in patients receiving dose-intensive or standard dose chemotherapy for high-risk primary breast cancer. Br J Cancer. Jan. 15, 2008;98(1):25-33.
Besse et al., The first in class, alkylator-histone-deacetylase-inhibitor fusion molecule EDO-S101 in combination with proteasome inhibitors induces highly synergistic pro-apoptotic signaling through UPR activiation and suppression of c-Myc and BCL2 in multiple meyloma. ASH, 2016.
Besse et al., The first-in-class alkylating HDAC inhibitor EDO-S101 is highly synergistic with proteasome inhibition against multiple myeloma through activation of multiple pathways. Blood Cancer J. Jul. 2017;7(7):e589. 4 pages.
Besse et al., The First-in-Class, Alkylator-Histone-Deacetylase-Inhibitor Fusion Molecule EDO-S101 in Combination with Proteasome Inhibitors Induces Highly Synergistic Pro-Apoptotic Signaling through UPR Activation and Suppression of c-MYC and BCL2 in Multiple Myeloma. 58th ASH Annual Meeting, San Diego, Dec. 3-6, 2016, Publication No. 4466. 1 page.
Bose et al., Histone deacetylase inhibitor (HDACI) mechanisms of action: emerging insights. Pharmacol Ther. Sep. 2014;143(3):323-36.
Bruce et al., Glioblastoma Multiforme Treatment & Management. Medscape. Retrieved online at: https://emedicine.medscape.com/article/283252-treatment. 20 pages. Jun. 14, 2017.
Cai et al., Combination of bendamustine and entinostat synergistically inhibits proliferation of multiple myeloma cells via induction of apoptosis and DNA damage response. Cancer Lett. Jul. 28, 2013;335(2):343-50.
Campos et al., Expression of nuclear receptor corepressors and class I histone deacetylases in astrocytic gliomas. Cancer Sci. Feb. 2011;102(2):387-92.
Chen et al., A 71-gene signature of TRAIL sensitivity in cancer cells. Mol Cancer Ther. Jan. 2012;11(1):34-44.
Chen et al., Discovery of a Novel, Efficient, and Scalable Route to Bendamustine Hydrochloride: The API in Treanda. Org Process Res Dev. 2011;15(5):1063-1072.
Chesi et al., Drug response in a genetically engineered mouse model of multiple myeloma is predictive of clinical efficacy. Blood. Jul. 12, 2012;120(2):376-85.
Chesi et al., Identification of Novel Therapeutic Targets in the Clinically Predictive Vk*MYC Mouse Model of Multple Myeloma. ASH, 2 pages. 2014.
Chesi et al., Identification of Novel Therapeutic Targets in the Clinically Predictive Vk*MYC Mouse Model of Multple Myeloma. Blood. 2014;124:415.

(56) References Cited

OTHER PUBLICATIONS

Chisholm et al., Emergence of drug tolerance in cancer cell populations: an evolutionary outcome of selection, nongenetic instability, and stress-induced adaptation. Cancer Res. Mar. 15, 2015;75(6):930-9.
Ciavatta et al., Epigenetic basis for aberrant upregulation of autoantigen genes in humans with ANCA vasculitis. J Clin Invest. Sep. 2010;120(9):3209-19.
ClinicalTrials.gov, Bendamustine, Lenalidomide (Revlimid®) and Dexamethasone (BRd) as 2nd-line Therapy for Patients With Relapsed or Refractory Multiple Myeloma (BRd). Clinical Trials Identifier: NCT01701076, Aug. 24, 2016.
ClinicalTrials.gov, Phase 1 Trial of Dasatinib and Bendamustine in Chronic Lymphocytic Leukemia. ClinicalTrials Identifier: NCT00872976, Apr. 22, 2009. 3 pages.
Connors, Hodgkin lymphoma: special challenges and solutions. Hematol Oncol. Jun. 2015;33 Suppl 1:21-4.
Cooke et al., Spontaneous onset and transplant models of the Vk*MYC mouse show immunological sequelae comparable to human multiple myeloma. J Transl Med. Sep. 6, 2016;14:259. 12 pages.
Curigliano et al., Cardiovascular toxicity induced by chemotherapy, targeted agents and radiotherapy: ESMO Clinical Practice Guidelines. Annals of Oncology. Oct. 2012;23(Suppl. 7):vii155-vii166.
De Filippi et al., Continuous Exposure to Bendamustine (BDM) Results in Stable Upregulation of CD30 and Increased Sensitivity to Brentuximab Vedotin (BV) in Tumor Cells of Hodgkin Lymphoma HL. Istituto Nazionale Tumor, IRCCS-Fondazione Pascale, Dec. 6, 2015. 1k page.
deSouza et al., Has the survival of patients with glioblastoma changed over the years? Br J Cancer. Jan. 19, 2016;114 (2):146-50.
Drogaris et al., Histone deacetylase inhibitors globally enhance h3/h4 tail acetylation without affecting h3 lysine 56 acetylation. Sci Rep. 2012;2:220. 12 pages.
Döhner et al., Diagnosis and management of acute myeloid leukemia in adults: recommendations from an international expert panel, on behalf of the European LeukemiaNet. Blood. Jan. 21, 2010;115(3):453-74.
EU Clinical Trials Register, EudraCT No. 2005-002051-41. 13 pages. Dec. 7, 2016.
EU Clinical Trials Register, EudraCT No. 2005-006083-57. 28 pages. Jun. 1, 2016.
Eurordis, Rare Diseases Europe, Why Research on Rare Diseases? Position Paper. Retrieved online at: www.eurordis.org. 14 pages. Oct. 2010.
Fei et al., Development of clinically relevant orthotopic xenograft mouse model of metastatic lung cancer and glioblastoma through surgical tumor tissues injection with trocar. J Exp Clin Cancer Res. Jun. 29, 2010;29:84.
Festuccia et al., Enhancement of radiosensitivity by the novel anticancer quinolone derivative vosaroxin in preclinical glioblastoma models. EJC, European Journal of Cancer. Dec. 2016;69(Suppl 1):562. Abstract 174, Poster P145.
Festuccia et al., Targeting glioblastoma with UniPR1331, a new and stable bioavailable small molecule inhibiting Ephephrin interaction: In vitro and in vivo evidence. EJC, European Journal of Cancer. Dec. 2016;69(Suppl 1), Abstract 71, Poster P042.
Frew et al., Enhancing the apoptotic and therapeutic effects of HDAC inhibitors. Cancer Lett. Aug. 8, 2009;280 (2):125-33.
Graham RL, Cooper B, Krause JR. T-cell prolymphocytic leukemia. Proc (Bayl Univ Med Cent). Jan. 2013;26(1):19-21.
Greaves et al., Clonal evolution in cancer. Nature. Jan. 18, 2012;481(7381):306-13.
Groselj et al., Histone deacetylase inhibitors as radiosensitisers: effects on DNA damage signalling and repair. Br J Cancer. Mar. 5, 2013;108(4):748-54.
Hancock et al., HDAC inhibitor therapy in autoimmunity and transplantation. Ann Rheum Dis. Apr. 2012;71 Suppl 2: i46-54.
Hegi et al., MGMT gene silencing and benefit from temozolomide in glioblastoma. N Engl J Med. Mar. 10, 2005;352 (10):997-1003.
Her et al., Targeting DNA Double-strand Break Repair in Cancer Therapy. Journal of Molecular and Genetic Medicine. Dec. 31, 2015;9:e106, 1 page.
Howlader et al., Contributions of Subtypes of Non-Hodgkin Lymphoma to Mortality Trends. Cancer Epidemiol Biomarkers Prev. Jan. 2016;25(1):174-9.
Jagannath et al., Bortezomib in combination with dexamethasone for the treatment of patients with relapsed and/or refractory multiple myeloma with less than optimal response to bortezomib alone. Haematologica. Jul. 2006;91 (7):929-34.
Jawhari et al., In Vitro and In Vivo Preclinical Activity of EDO-S101 in Hodgkin Lymphoma. Haematologica. 2016;101 (s5):6-7, Abstract P037.
Jennette et al., Pathogenesis of antineutrophil cytoplasmic autoantibody-mediated disease. Nat Rev Rheumatol. Aug. 2014;10(8):463-73.
Jiang et al., A mammalian functional-genetic approach to characterizing cancer therapeutics. Nature Chemical Biology. Feb. 2011;7:92-100.
Kaddour et al., Transmission of Induced Chromosomal Aberrations through Successive Mitotic Divisions in Human Lymphocytes after In Vitro and ?In? Vivo Radiation. Scientific Reports. Jun. 12, 2017;7:3291, 11 pages.
Kallenberg, Pathogenesis of ANCA-associated vasculitides. Ann Rheum Dis. Mar. 2011;70 Suppl 1:i59-63.
Audeh et al., Oral poly(ADP-ribose) polymerase inhibitor olaparib in patients with BRCA1 or BRCA2 mutations and recurrent ovarian cancer: a proof-of-concept trial. Lancet. Jul. 24, 2010;376(9737):245-51.
De Filippi et al., Edo-S101, a Bendamustine (BDM)/Histone-Deacetylase Inhibitor (HDACi) Fusion Molecule, Demonstrates Potent Preclinical Activity Against T-Cell Malignancies and Overcomes BDM-Resistance. ASH, 59th Annual Meeting & Exposition. Dec. 9-12, 2017. Poster 2547. 1 page.
Dooley et al., Alkylating Histone Deacetylase Inhibitor Treatment in Animal Models of MPO-ANCA Vasculitis. Abstract TH-PO052. ASN, Kidney Week, Nov. 2, 2017, 2 pages.
Festuccia et al., The first-in-class alkylating deacetylase inhibitor molecule tinostamustine shows antitumor effects and is synergistic with radiotherapy in preclinical models of glioblastoma. J Hematol Oncol. Feb. 27, 2018;11(1):32. 19 pages.
Krause et al., Tyrosine kinases as targets for cancer therapy. N Engl J Med. Jul. 14, 2005;353(2):172-87.
Ocio et al., Deacetylase Inhibition in Haematological Malignancies—Advanced T-cell Lymphoma, Hodgkin's Lymphoma, Multiple Myeloma, Acute Myelogenous Leukaemia and Myelodysplastic Syndrome. European Haematology. 2010;4:47-50.
Ocio, Epigenetic regulation and HAC inhibitors, Still a role for these agents in MM? Institute of Biomedical Research of Salamanca, University of Salamanca, Cancer Research Center, Slideshow. 32 pages, (2016).
Qian et al., Activity of PXD101, a histone deacetylase inhibitor, in preclinical ovarian cancer studies. Mol Cancer Ther. 2006;5(8):2086-2095.
Ryu et al., Valproic acid downregulates the expression of MGMT and sensitizes temozolomide-resistant glioma cells. J Biomed Biotechnol. 2012;2012:987495. 9 pages.

* cited by examiner

THERAPEUTIC AGENTS

The present invention relates to a class of hydroxamic acid compounds, which act as alkylating agents and/or inhibitors of the HDAC pathway, to uses thereof, to processes for the preparation thereof and compositions comprising said compounds. These compounds have potential utility in a variety of therapeutic areas including the treatment of a neoplastic disease and immune diseases.

Cancer is one of the most life threatening diseases in which cells in a part of the body experience out-of-control growth. According to latest data from American Cancer Society, it is estimated to have 1.6 million new cases of cancer in USA in 2011. Cancer is the second leading cause of death in the United States (second only to heart disease) and will claim more than 570,000 lives in 2011. In fact, it is estimated that 50% of all men and 33% of all women living in the United States will develop some type of cancer in their lifetime. Therefore cancer constitutes a major public health burden and represents a significant cost in the United States. For decades, surgery, chemotherapy, and radiation were the established treatments for various cancers. Patients usually receive a combination of these treatments depending upon the type and extent of their disease. But the chemotherapy is most important option for cancer patient when the surgery treatment is impossible.

Bendamustine, a well known chemotherapy first synthesized in 1963, consists of an alkylating nitrogen mustard moiety and a purine-like benzimidazole moiety with a suggested purine-analog effect (Barman Balfour J A, et al, *Drugs* 2001; 61: 631-640). Bendamustine has been shown to have substantial activity against low-grade lymphomas (Herold M, et al., *Blood*, 1999; 94, Suppl 1: 262a), multiple myelomas (Poenisch W, et al., *Blood* 2000; 96, Suppl 1: 759a), and several solid tumors (Kollmannsberger C, et al., *Anticancer Drugs* 2000; 11: 535-539). It was also reported that bendamustine effectively induces apoptosis in lymphoma cells (Chow K U, et al., *Haematologica,* 2001; 86: 485-493). It has received FDA approval for the treatment of chronic lymphocytic leukemia (CLL) and for treatment of indolent B-cell non-Hodgkin's lymphoma (NHL) that has progressed during or within six months of treatment with rituximab or a rituximab-containing regimen.

In recent years, histone deacetylases (HDAC) has emerged as an important disease target for cancer treatment [Minucci, S. et al., *Nat Rev Cancer* 2006, 6, 38-51]. The human HDAC enzymes have 18 isoforms grouped into Class I-IV according to their sequence homology. Class I, II and IV, commonly referred to as the classical HDACs, are comprised of 11 family members. Class III HDACs consists of 7 enzymes and they are distinct from other HDAC family members, therefore are given a unique term sirtuins. The inhibition of HDAC enzyme leads to histone acetylation which is associated with the remodelling of chromatin and plays a key role in the epigenetic regulation of gene expression. In addition, HDAC inhibitors have been shown to evoke the acetylation of many important non-histone proteins such as HSP90, alpha-tubulin, Ku-70, Bcl-6, importin, cortactin, p53, STAT1, E2F1, GATA-1 and NF-kB, which can alter many important signaling networks related to cancer treatment. The underlying mechanism of action of HDAC inhibitors includes the differentiation, cell cycle arrest, inhibition of DNA repair, induction of apoptosis, upregulation of tumor suppressors, down regulation of growth factors, oxidative stress and autophagy. In the last decade, a large number of structurally diverse HDAC inhibitors have been identified and at least 12 HDAC inhibitors are currently in human clinical trials for cancer treatments, including short-chain fatty acid (valproic acid), hydroxamates (SAHA, LBH589, PXD101, JNJ-26481585, ITF2357, CUDC-101), cyclic tetrapeptides (FK-228), benzamide (MS-275), and several other compounds (CHR-3996, 4SC-201, SB939). Among them, SAHA and FK-228 has been approved by the US FDA for the treatment of advanced cutaneous T-cell lymphoma.

WO 2010/085377 refers to a class of hydroxamic acid derivatives, which inhibit the HDAC pathway and have potential utility in the treatment of a neoplastic disease or an autoimmne disease. Among the compounds disclosed is NL-101 having the structure shown below:

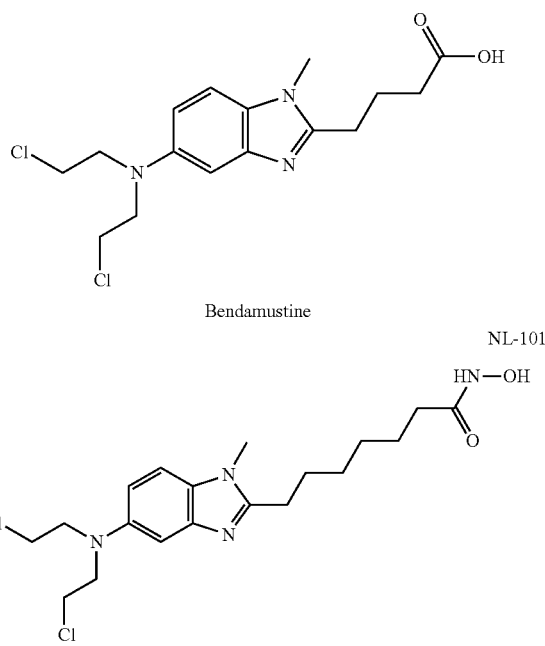

Bendamustine

NL-101

The biological assay showed that NL-101 potently inhibits HDAC enzyme (HDAC1 $IC_{50}$ of 9 nM). NL-101 was sent to NCI (NSC#751447) for NCI-60 cell line panel screening. The data showed that NL-101 is about ×25-100 fold more potent than Bendamustine in the NCI-60 cell lines that are representative of a variety of human cancer type.

There is a continuing need for further pharmaceuticals useful for the treatment of cancer and auto-immune diseases, preferably having advantages over existing therapies, such as improved potency or selectivity, or reduced toxicity.

The present invention relates to a class of hydroxamic acid derivatives, which act as alkylating agents and/or inhibitors of the HDAC pathway. The single dual-functional small molecules of the invention may attack the cancer cells synergistically from two distinct directions simultaneously (DNA damaging and the inhibitions of the HDAC pathway). Thus, the compounds of the present invention may be useful in treating a patient having a tumor, such as one treatable by Bendamustine and/or the inhibitors of HDAC pathway. The compounds of the invention may additionally be useful in the prevention and treatment of an immune disease.

Thus, in one aspect, this invention relates to a compound of Formula (I) or an N-oxide thereof, or a pharmaceutically acceptable salt, solvate, polymorph or tautomer of said compound of formula (I) or N-oxide thereof:

Formula (I)

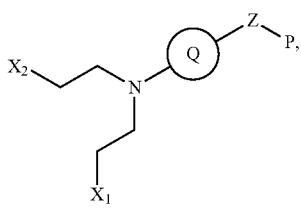

wherein
Z is $(CR_aR_b)_pN(R_a)(CR_aR_b)_q$;
$X_1$ and $X_2$ are each independently selected from halo and $OSO_2R_c$;
P is

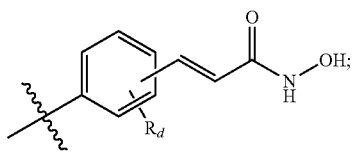

Q is heteroaryl, which is optionally substituted with alkyl, alkenyl, alkynyl, cycloalkyl, halo, nitro, oxo, cyano or $OR_e$;
$R_a$, $R_b$, $R_d$ and $R_e$ are each independently selected from H, alkyl, alkenyl and alkynyl;
$R_c$ is selected from alkyl, alkenyl and alkynyl; and
p and q are each independently selected from 0, 1, 2, 3 and 4;
a tautomer thereof or a pharmaceutically acceptable salt, solvate or polymorph of said compound or tautomer.

Preferably, p and q are each independently selected from 1, 2, and 3. More preferably, p is 1 and q is 2; or p is 2 and q is 1; or p is 0 and q is 3; or p is 3 and q is 0; or p and q are both 2.

Preferably, Z is $(CH_2)_pNH(CH_2)_q$. Most preferably, Z is $(CH_2)_2NH(CH_2)$.

Preferably, $X_1$ and $X_2$ are each independently selected from halo. More preferably, $X_1$ and $X_2$ are each independently selected from chloro, bromo and iodo. Most preferably, $X_1$ and $X_2$ are both chloro.

Preferably, Q is an optionally substituted 9-10 membered heteroaryl. More preferably, Q is an optionally substituted benzimidazolyl. Yet more preferably, Q is benzimidazolyl substituted by one or more alkyl groups. Even more preferably, Q is benzimidazolyl substituted by 1, 2, or 3 methyl groups. Most preferably, Q is benzimidazolyl substituted by a methyl group.

In a preferred embodiment, the compounds of the invention are represented by Formula (II):

Formula (II)

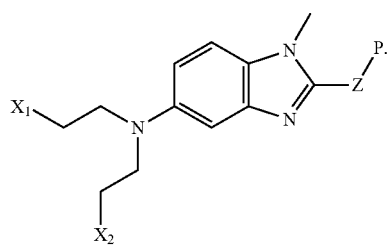

In more preferred embodiments, the compounds of the invention are represented by Formula (III) or Formula (IIIA):

Formula (III)

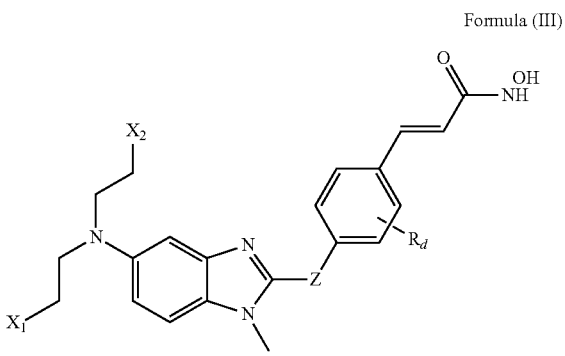

Formula (IIIA)

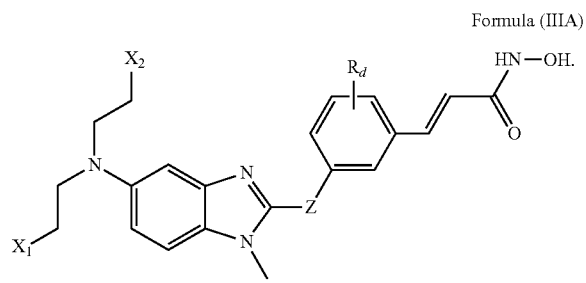

In a more preferred embodiment, the compounds of the invention are represented by Formula (III) or Formula (IIIA) wherein $X_1$ and $X_2$ are each independently selected from halo, and Z is $(CH_2)_pNH(CH_2)_q$.

In a yet more preferred embodiment, the compounds of the invention are represented by Formula (III) or Formula (IIIA) wherein $X_1$ and $X_2$ are both chloro, and Z is $(CH_2)_2NH(CH_2)$.

The following compounds are preferred:

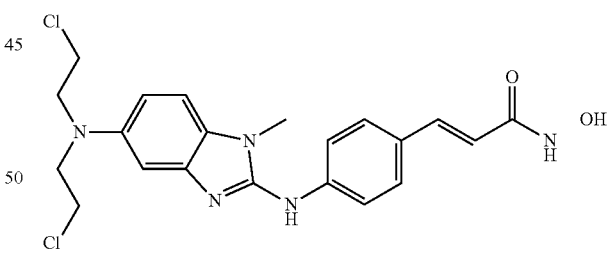

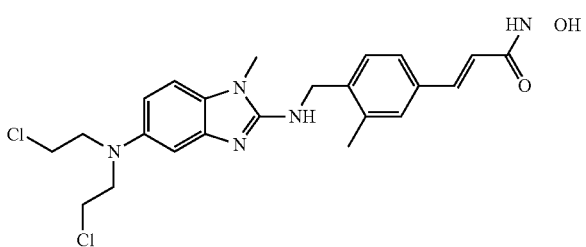

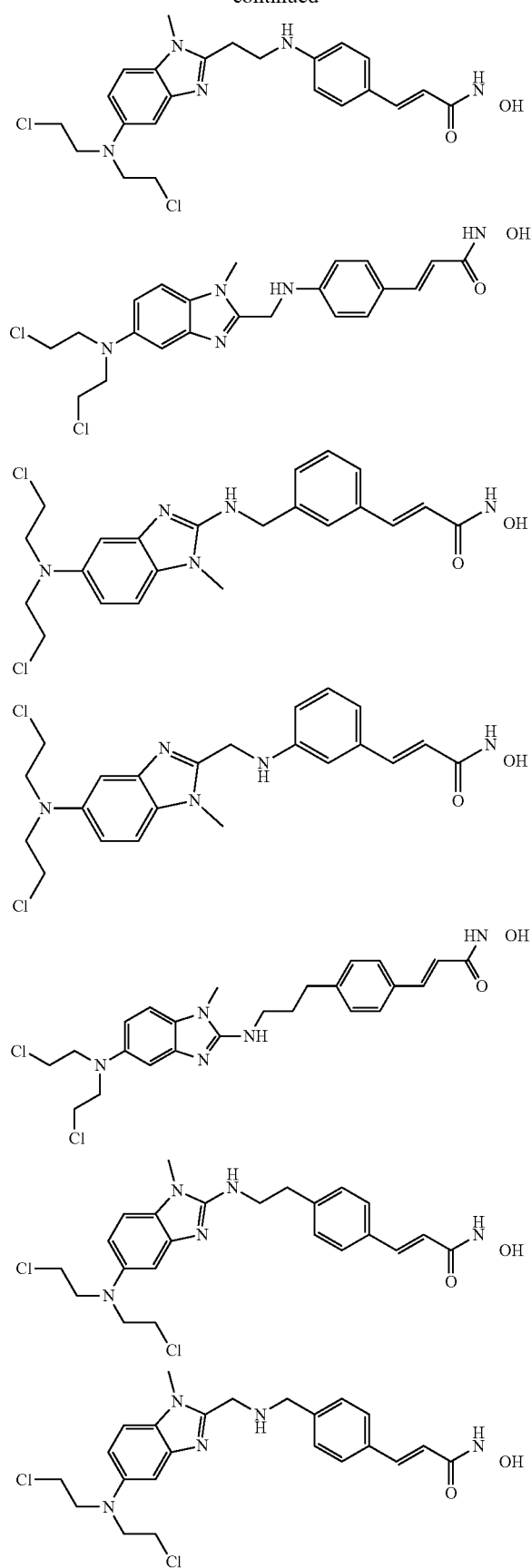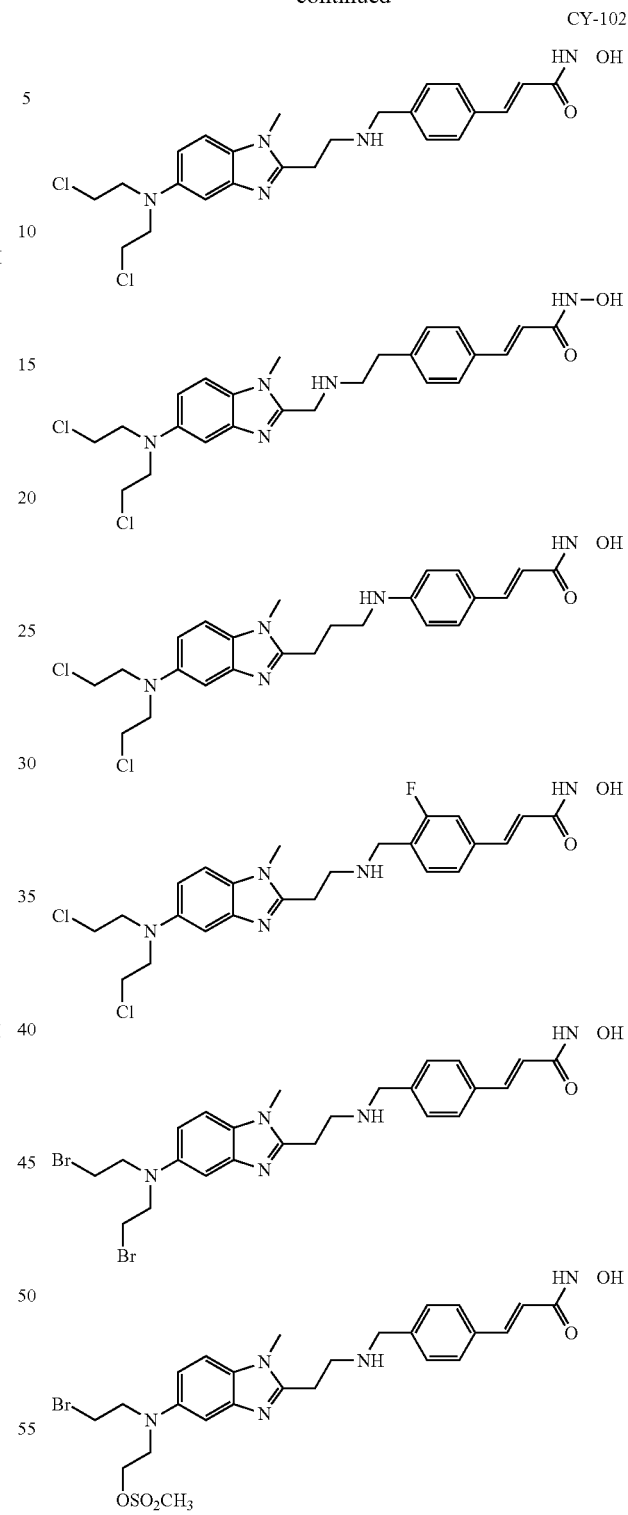
The alkene group in the compounds of Formula (I) may be in the form of either the (E) or (Z)-isomer, and are preferably the (E) isomer. In particular, the most preferred compound CY-102 is the (E)-isomer.
It should be recognized that the compounds of the present invention may be present and optionally administered in the form of salts or solvates. The invention encompasses any pharmaceutically acceptable salts and solvates of any one of the above-described compounds and modifications thereof.

The most preferred compound is the compound CY-102 or a pharmaceutically acceptable salt, solvate or polymorph thereof:

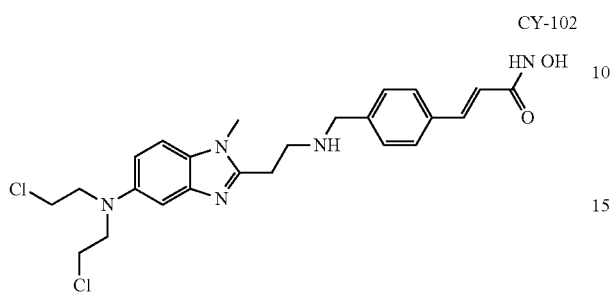

CY-102

Also within the scope of this invention is a pharmaceutical composition containing one or more of the compounds, modifications, and/or salts or solvates thereof described above for use in treating a neoplastic disease, or an immune disorder, therapeutic uses thereof, and use of the compounds for the manufacture of a medicament for treating the disease/disorder.

This invention also relates to a method of treating a neoplastic disorder (e.g., cancer, myelodysplastic syndrome, or myeloproliferative disease) by administering to a subject in need thereof an effective amount of one or more of the compounds, modifications, and/or salts or solvates, and compositions thereof described above.

Furthermore, this invention relates to a method of treating an immune disease (e.g., rheumatoid arthritis and multiple sclerosis) by administering to a subject in need thereof an effective amount of one or more of the compounds, modifications, and/or salts or solvates, and compositions thereof described above.

The details of one or more embodiments of the invention are set forth in the description below. Other features, objects, and advantages of the invention will be apparent from the description and from the claims. It should be understood that all embodiments/features of the invention (compounds, pharmaceutical compositions, methods of make/use, etc) described herein, including any specific features described in the examples and original claims, can combine with one another unless not applicable or explicitly disclaimed.

Compounds of the invention may contain one or more asymmetric carbon atoms. Accordingly, the compounds may exist as diastereomers, enantiomers or mixtures thereof. The syntheses of the compounds may employ racemates, diastereomers or enantiomers as starting materials or as intermediates. Diastereomeric compounds may be separated by chromatographic or crystallization methods. Similarly, enantiomeric mixtures may be separated using the same techniques or others known in the art. Each of the asymmetric carbon atoms may be in the R or S configuration and both of these configurations are within the scope of the invention.

A modified compound of any one of such compounds including a modification having an improved (e.g., enhanced, greater) pharmaceutical solubility, stability, bioavailability and/or therapeutic index as compared to the unmodified compound is also contemplated. The examples of modifications include but not limited to the prodrug derivatives, the deuterium-enriched compounds, and compound conjugates with polyethylene glycol, dextran, polyvinyl alcohol, carbohydrate polymer, antibody, small biomolecule such as Vitamin E or its derivatives, or mixtures thereof. For example:

Prodrug derivatives: prodrugs, upon administration to a subject, are converted in vivo into active compounds of the present invention [*Nature Reviews of Drug Discovery,* 2008, Volume 7, p 255]. It is noted that in many instances, the prodrugs themselves also fall within the scope of the range of compounds according to the present invention. The prodrugs of the compounds of the present invention can be prepared by standard organic reaction, for example, by reacting with a carbamylating agent (e.g., 1,1-acyloxyalkylcarbonochloridate, para-nitrophenyl carbonate, or the like) or an acylating agent. Further examples of methods and strategies of making prodrugs are described in *Bioorganic and Medicinal Chemistry Letters,* 1994, Vol. 4, p. 1985.

Deuterium-enriched compounds: deuterium (D or $^2$H) H) s a stable, non-radioactive isotope of hydrogen and has an atomic weight of 2.0144. Hydrogen naturally occurs as a mixture of the isotopes $^X$H (hydrogen or protium), D ($^2$H or deuterium), and T ($^3$H or tritium). The natural abundance of deuterium is 0.015%. One of ordinary skill in the art recognizes that in all chemical compounds with a H atom, the H atom actually represents a mixture of H and D, with about 0.015% being D. Thus, compounds with a level of deuterium that has been enriched to be greater than its natural abundance of 0.015%, should be considered unnatural and, as a result, novel over their nonenriched counterparts.

Compound-polymer conjugates: Many anti-cancer agents exhibit excellent antitumor activity against in vivo animal xenografts. However, their water insolubility makes it difficult to administer these drugs. One approach to overcome the pharmaceutical and pharmacokinetic shortcomings of these poor soluble drugs is to covalently bind them to polymers such as polyethylene glycol, dextran, polyvinyl alcohol, and carbohydrate polymers. Using this approach, the water solubility of the anticancer agent can be improved such that the polymeric conjugate can be parenterally administered in aqueous medium.

Compound-antibody conjugates: For many years it has been an aim of scientists in the field of specifically targeted drug therapy to use monoclonal antibodies (MAbs) for the specific delivery of toxic agents to human cancers. Conjugates of tumor-associated MAbs and suitable toxic agents have been developed. The toxic agent is most commonly a chemotherapy drug, although particle-emitting radionuclides, or bacterial or plant toxins have also been conjugated to MAbs, especially for the therapy of cancer (Sharkey and Goldenberg, C A Cancer J. Clin. 2006 July-August; 56(4):226-243). The advantages of using MAb-chemotherapy drug conjugates are that (a) the chemotherapy drug itself is structurally well defined; (b) the chemotherapy drug is linked to the MAb protein using very well defined conjugation chemistries, often at specific sites remote from the MAbs antigen binding regions; (c) MAb-chemotherapy drug conjugates can be made more reproducibly than chemical conjugates involving MAbs and bacterial or plant toxins, and as such are more amenable to commercial development and regulatory approval; and (d) the MAb-chemotherapy drug conjugates are orders of magnitude less toxic systemically than radionuclide MAb conjugates.

When the compounds of the present invention possess a free base form, the compounds can be prepared as a pharmaceutically acceptable acid addition salt by reacting the free base form of the compound with a pharmaceutically acceptable inorganic or organic acid, e.g., hydrohalides such as hydrochloride, hydrobromide, hydroiodide; other mineral acids such as sulfate, nitrate, phosphate, etc.; and alkyl and monoarylsulfonates such as ethanesulfonate, toluenesulfonate and benzenesulfonate; and other organic acids and their corresponding salts such as acetate, tartrate, maleate, succinate, citrate, benzoate, salicylate and ascorbate. Further acid addition salts of the present invention include, but are not limited to: adipate, alginate, arginate, aspartate, bisulfate, bisulfite, bromide, butyrate, camphorate, camphorsulfonate, caprylate, chloride, chlorobenzoate, cyclopentanepropionate, digluconate, dihydrogenphosphate, dinitrobenzoate, dodecylsulfate, fumarate, galacterate (from mucic acid), galacturonate, glucoheptaoate, gluconate, glutamate, glycerophosphate, hemisuccinate, hemisulfate, heptanoate, hexanoate, hippurate, 2-hydroxyethanesulfonate, iodide, isethionate, iso-butyrate, lactate, lactobionate, malonate, mandelate, metaphosphate, methanesulfonate, methylbenzoate, monohydrogenphosphate, 2-naphthalenesulfonate, nicotinate, oxalate, oleate, pamoate, pectinate, persulfate, phenylacetate, 3-phenylpropionate, phosphonate and phthalate.

When the compounds of the present invention possess a free acid form, a pharmaceutically acceptable base addition salt can be prepared by reacting the free acid form of the compound with a pharmaceutically acceptable inorganic or organic base. Examples of such bases are alkali metal hydroxides including potassium, sodium and lithium hydroxides; alkaline earth metal hydroxides such as barium and calcium hydroxides; alkali metal alkoxides, e.g., potassium ethanolate and sodium propanolate; and various organic bases such as ammonium hydroxide, piperidine, diethanolamine and N-methylglutamine. Also included are the aluminum salts of the compounds of the present invention. Further base salts of the present invention include, but are not limited to: copper, ferric, ferrous, lithium, magnesium, manganic, manganous, potassium, sodium and zinc salts. Organic base salts include, but are not limited to, salts of primary, secondary and tertiary amines, substituted amines including naturally occurring substituted amines, cyclic amines and basic ion exchange resins, e.g., arginine, betaine, caffeine, chloroprocaine, choline, N,N'-dibenzylethylenediamine (benzathine), dicyclohexylamine, diethanolamine, 2-diethylaminoethanol, 2-dimethylaminoethanol, ethanolamine, ethylenediamine, N-ethylmorpholine, N-ethylpiperidine, glucamine, glucosamine, histidine, hydrabamine, iso-propylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris-(hydroxymethyl)-methylamine (tromethamine). It should be recognized that the free acid forms will typically differ from their respective salt forms somewhat in physical properties such as solubility in polar solvents, but otherwise the salts are equivalent to their respective free acid forms for the purposes of the present invention.

In one aspect, a pharmaceutically acceptable salt is a hydrochloride salt, hydrobromide salt, methanesulfonate, toluenesulfonate, acetate, fumarate, sulfate, bisulfate, succinate, citrate, phosphate, maleate, nitrate, tartrate, benzoate, biocarbonate, carbonate, sodium hydroxide salt, calcium hydroxide salt, potassium hydroxide salt, tromethamine salt, or mixtures thereof.

The compound CY-102 is preferably formed and/or used as the hydrochloride salt.

Compounds of the present invention that comprise tertiary nitrogen-containing groups may be quaternized with such agents as $(C_{1-4})$ alkyl halides, e.g., methyl, ethyl, iso-propyl and tert-butyl chlorides, bromides and iodides; di-$(C_{1-4})$ alkyl sulfates, e.g., dimethyl, diethyl and diamyl sulfates; alkyl halides, e.g., decyl, dodecyl, lauryl, myristyl and stearyl chlorides, bromides and iodides; and aryl $(C_{1-4})$ alkyl halides, e.g., benzyl chloride and phenethyl bromide. Such salts permit the preparation of both water- and oil-soluble compounds of the invention.

Amine oxides, also known as amine-N-oxide and N-oxide, of anti-cancer agents with tertiary nitrogen atoms have been developed as prodrugs [Mol Cancer Therapy. 2004 March; 3(3):233-44]. Compounds of the present invention that comprise tertiary nitrogen atoms may be oxidized by such agents as hydrogen peroxide ($H_2O_2$), Caro's acid or peracids like meta-Chloroperoxybenzoic acid (mCPBA) to from amine oxide.

The compound CY-102 may, for example, be used in the form of its N-oxide or a salt thereof.

The invention encompasses pharmaceutical compositions comprising the compound of the present invention and pharmaceutical excipients, as well as other conventional pharmaceutically inactive agents. Any inert excipient that is commonly used as a carrier or diluent may be used in compositions of the present invention, such as sugars, polyalcohols, soluble polymers, salts and lipids. Sugars and polyalcohols which may be employed include, without limitation, lactose, sucrose, mannitol, and sorbitol. Illustrative of the soluble polymers which may be employed are polyoxyethylene, poloxamers, polyvinylpyrrolidone, and dextran. Useful salts include, without limitation, sodium chloride, magnesium chloride, and calcium chloride. Lipids which may be employed include, without limitation, fatty acids, glycerol fatty acid esters, glycolipids, and phospholipids.

In addition, the pharmaceutical compositions may further comprise binders (e.g., *acacia*, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, cyclodextrins), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the pharmaceutical compositions are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

Additionally, the invention encompasses pharmaceutical compositions comprising any solid or liquid physical form of the compound of the invention. For example, the compounds can be in a crystalline form, in amorphous form, and have any particle size. The particles may be micronized, or may be agglomerated, particulate granules, powders, oils, oily suspensions or any other form of solid or liquid physical form.

Definitions

The term "alkyl" refers to a straight or branched hydrocarbon containing 1-20 carbon atoms (e.g., $C_1$-$C_{10}$). Examples of alkyl include, but are not limited to, methyl, methylene, ethyl, ethylene, n-propyl, i-propyl, n-butyl, i-butyl, and t-butyl. Preferably, the alkyl group has one to ten carbon atoms. More preferably, the alkyl group has one to four carbon atoms.

The term "alkenyl" refers to a straight or branched hydrocarbon containing 2-20 carbon atoms (e.g., $C_2$-$C_{10}$) and one or more double bonds. Examples of alkenyl include, but are not limited to, ethenyl, propenyl, and allyl. Preferably, the alkylene group has two to ten carbon atoms. More preferably, the alkylene group has two to four carbon atoms.

The term "alkynyl" refers to a straight or branched hydrocarbon containing 2-20 carbon atoms (e.g., $C_2$-$C_{10}$) and one or more triple bonds. Examples of alkynyl include, but are not limited to, ethynyl, 1-propynyl, 1- and 2-butynyl, and 1-methyl-2-butynyl. Preferably, the alkynyl group has two to ten carbon atoms. More preferably, the alkynyl group has two to four carbon atoms.

The term "cycloalkyl" refers to a saturated hydrocarbon ring system having 3 to 30 carbon atoms (e.g., $C_3$-$C_{12}$, $C_3$-$C_8$, $C_3$-$C_6$). Examples of cycloalkyl include, but are not limited to, cyclopropyl, cyclobutyl, cyclopentyl, cyclohexyl, cycloheptyl, and cyclooctyl.

The term "heteroaryl" refers to an aromatic 5-8 membered monocyclic, or an 8-12 membered bicyclic ring system having one or more heteroatoms selected from O, N, S, P and Se). Examples of heteroaryl groups include pyridyl, furyl, imidazolyl, benzimidazolyl, pyrimidinyl, thienyl, quinolinyl, indolyl, and thiazolyl.

"Halo" means fluoro, chloro, bromo or iodo.

"Protected derivatives" means derivatives of compounds in which a reactive site are blocked with protecting groups. Protected derivatives are useful in the preparation of pharmaceuticals or in themselves may be active as inhibitors. A comprehensive list of suitable protecting groups can be found in T. W. Greene, Protecting Groups in Organic Synthesis, 3rd edition, Wiley & Sons, 1999.

"Pharmaceutically acceptable carrier" means a non-toxic solvent, dispersant, excipient, adjuvant, or other material which is mixed with the compounds of the present invention in order to form a pharmaceutical composition, i.e., a dose form capable of administration to the patient. Examples of pharmaceutically acceptable carrier includes suitable polyethylene glycol (e.g., PEG400), surfactant (e.g., Cremophor), or cyclopolysaccharide (e.g., hydroxypropyl-β-cyclodextrin or sulfobutyl ether β-cyclodextrins), polymer, liposome, micelle, nanosphere, etc.

"Therapeutically effective amount" of a composition described herein is meant an amount of the composition which confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). An effective amount of the composition described above may range from about 0.1 mg/kg to about 500 mg/kg, preferably from about 0.2 to about 50 mg/kg. Effective doses will also vary depending on route of administration, as well as the possibility of co-usage with other agents. It will be understood, however, that the total daily usage of the compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts.

As used herein, the term "treating" refers to administering a compound to a subject that has, for example, a neoplastic or immune disorder, or has a symptom of or a predisposition toward it, with the purpose to cure, heal, alleviate, relieve, alter, remedy, ameliorate, improve, or affect the disorder, the symptoms of or the predisposition toward the disorder. The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents.

A "subject" refers to a human and a non-human animal. Examples of a non-human animal include all vertebrates, e.g., mammals, such as non-human primates (particularly higher primates), dog, rodent (e.g., mouse or rat), guinea pig, cat, and non-mammals, such as birds, amphibians, reptiles, etc. In a preferred embodiment, the subject is a human. In another embodiment, the subject is an experimental animal or animal suitable as a disease model.

When compounds according to the present invention exhibit insufficient solubility, methods for solubilizing the compounds may be used. Such methods are known to those of skill in this art, and include, but are not limited to, pH adjustment and salt formation, using co-solvents, such as ethanol, propylene glycol, polyethylene glycol (PEG) 300, PEG 400, DMA (10-30%), DMSO (10-20%), NMP (10-20%), using surfactants, such as polysorbate 80, polysorbate 20 (1-10%), cremophor EL, Cremophor RH40, Cremophor RH60 (5-10%), Pluronic F68/Poloxamer 188 (20-50%), Solutol HS15 (20-50%), Vitamin E TPGS, and d-α-tocopheryl PEG 1000 succinate (20-50%), using complexation such as HPβCD and SBEβCD (10-40%), and using advanced approaches such as micelle, addition of a polymer, nanoparticle suspensions, and liposome formation.

"Combination therapy" includes the administration of the subject compounds of the present invention in further combination with other biologically active ingredients (such as, but not limited to, a second and different antineoplastic agent) and non-drug therapies (such as, but not limited to, surgery or radiation treatment). For instance, the compounds of the invention can be used in combination with other pharmaceutically active compounds, or non-drug therapies, preferably compounds that are able to enhance the effect of the compounds of the invention. The compounds of the invention can be administered simultaneously (as a single preparation or separate preparation) or sequentially to the other therapies. In general, a combination therapy envisions administration of two or more drugs/treatments during a single cycle or course of therapy.

In one embodiment, the compounds of the invention are administered in combination with one or more of traditional chemotherapeutic agents. The traditional chemotherapeutic agents encompass a wide range of therapeutic treatments in the field of oncology. These agents are administered at various stages of the disease for the purposes of shrinking tumors, destroying remaining cancer cells left over after surgery, inducing remission, maintaining remission and/or alleviating symptoms relating to the cancer or its treatment. Examples of such agents include, but are not limited to, alkylating agents such as Nitrosureas (e.g., Carmustine, Lomustine and Streptozocin), ethylenimines (e.g., thiotepa, hexamethylmelanine), Alkylsulfonates (e.g., Busulfan), Hydrazines and Triazines (e.g., Altretamine, Procarbazine, Dacarbazine and Temozolomide), and platinum based agents (e.g., Carboplatin, Cisplatin, and Oxaliplatin); plant alkaloids such as Podophyllotoxins (e.g., Etoposide and Tenisopide), Taxanes (e.g., Paclitaxel and Docetaxel), Vinca alkaloids (e.g., Vincristine, Vinblastine and Vinorelbine); anti-tumor antibiotics such as Chromomycins (e.g., Dactinomycin and Plicamycin), Anthracyclines (e.g., Doxorubicin, Daunorubicin, Epirubicin, Mitoxantrone, and Idarubicin), and miscellaneous antibiotics such as Mitomycin and Bleomycin; anti-metabolites such as folic acid antagonists (e.g., Methotrexate), pyrimidine antagonists (e.g., 5-Fluorouracil, Foxuridine, Cytarabine, Capecitabine, and Gemcitabine), purine antagonists (e.g., 6-Mercaptopurine and 6-Thioguanine) and adenosine deaminase inhibitors (e.g., Cladribine, Fludarabine, Nelarabine and Pentostatin); topoisomerase inhibitors such as topoisomerase I inhibitors (Topotecan, Irinotecan), topoisomerase II inhibitors (e.g., Amsacrine, Etoposide, Etoposide phosphate, Teniposide), and miscellaneous anti-neoplastics such as ribonucleotide reductase inhibitors (Hydroxyurea), adrenocortical steroid inhibitor (Mitotane), anti-microtubule agents (Estramustine), and retinoids (Bexarotene, Isotretinoin, Tretinoin (ATRA).

In one aspect of the invention, the compounds may be administered in combination with one or more targeted anti-cancer agents that modulate protein kinases involved in various disease states. Examples of such kinases may include, but are not limited ABL1, ABL2/ARG, ACK1, AKT1, AKT2, AKT3, ALK, ALK1/ACVRL1, ALK2/ACVR1, ALK4/ACVR1B, ALK5/TGFBR1, ALK6/BMPR1B, AMPK(A1/B1/G1), AMPK(A1/B1/G2), AMPK(A1/B1/G3), AMPK(A1/B2/G1), AMPK(A2/B1/G1), AMPK(A2/B2/G1), AMPK(A2/B2/G2), ARAF, ARK5/NUAK1, ASK1/MAP3K5, ATM, Aurora A, Aurora B, Aurora C, AXL, BLK, BMPR2, BMX/ETK, BRAF, BRK, BRSK1, BRSK2, BTK, CAMK1a, CAMK1b, CAMK1d, CAMK1g, CAMKIIa, CAMKIIb, CAMKIId, CAMKIIg, CAMK4, CAMKK1, CAMKK2, CDC7-DBF4, CDK1-cyclin A, CDK1-cyclin B, CDK1-cyclin E, CDK2-cyclin A, CDK2-cyclin A1, CDK2-cyclin E, CDK3-cyclin E, CDK4-cyclin D1, CDK4-cyclin D3, CDK5-p25, CDK5-p35, CDK6-cyclin D1, CDK6-cyclin D3, CDK7-cyclin H, CDK9-cyclin K, CDK9-cyclin T1, CHK1, CHK2, CK1a1, CK1d, CK1epsilon, CK1g1, CK1g2, CK1g3, CK2a, CK2a2, c-KIT, CLK1, CLK2, CLK3, CLK4, c-MER, c-MET, COT1/MAP3K8, CSK, c-SRC, CTK/MATK, DAPK1, DAPK2, DCAMKL1, DCAMKL2, DDR1, DDR2, DLK/MAP3K12, DMPK, DMPK2/CDC42BPG, DNA-PK, DRAK1/STK17A, DYRK1/DYRK1A, DYRK1B, DYRK2, DYRK3, DYRK4, EEF2K, EGFR, EIF2AK1, EIF2AK2, EIF2AK3, EIF2AK4/GCN2, EPHA1, EPHA2, EPHA3, EPHA4, EPHA5, EPHA6, EPHA7, EPHA8, EPHB1, EPHB2, EPHB3, EPHB4, ERBB2/HER2, ERBB4/HER4, ERK1/MAPK3, ERK2/MAPK1, ERK5/MAPK7, FAK/PTK2, FER, FES/FPS, FGFR1, FGFR2, FGFR3, FGFR4, FGR, FLT1/VEGFR1, FLT3, FLT4/VEGFR3, FMS, FRK/PTK5, FYN, GCK/MAP4K2, GRK1, GRK2, GRK3, GRK4, GRK5, GRK6, GRK7, GSK3a, GSK3b, Haspin, HCK, HGK/MAP4K4, HIPK1, HIPK2, HIPK3, HIPK4, HPK1/MAP4K1, IGF1R, IKKa/CHUK, IKKb/IKBKB, IKKe/IKBKE, IR, IRAK1, IRAK4, IRR/INSRR, ITK, JAK1, JAK2, JAK3, JNK1, JNK2, JNK3, KDR/VEGFR2, KHS/MAP4K5, LATS1, LATS2, LCK, LCK2/ICK, LKB1, LIMK1, LOK/STK10, LRRK2, LYN, LYNB, MAPKAPK2, MAPKAPK3, MAPKAPK5/PRAK, MARK1, MARK2/PAR-1Ba, MARK3, MARK4, MEK1, MEK2, MEKK1, MEKK2, MEKK3, MELK, MINK/MINK1, MKK4, MKK6, MLCK/MYLK, MLCK2/MYLK2, MLK1/MAP3K9, MLK2/MAP3K10, MLK3/MAP3K11, MNK1, MNK2, MRCKa/, CDC42BPA, MRCKb/, CDC42BPB, MSK1/RPS6KA5, MSK2/RPS6KA4, MSSK1/STK23, MST1/STK4, MST2/STK3, MST3/STK24, MST4, mTOR/FRAP1, MUSK, MYLK3, MYO3b, NEK1, NEK2, NEK3, NEK4, NEK6, NEK7, NEK9, NEK11, NIK/MAP3K14, NLK, OSR1/OXSR1, P38a/MAPK14, P38b/MAPK11, P38d/MAPK13, P38g/MAPK12, P70S6K/RPS6KB1, p70S6Kb/, RPS6KB2, PAK1, PAK2, PAK3, PAK4, PAK5, PAK6, PASK, PBK/TOPK, PDGFRa, PDGFRb, PDK1/PDPK1, PDK1/PDHK1, PDK2/PDHK2, PDK3/PDHK3, PDK4/PDHK4, PHKg1, PHKg2, PI3Ka, (p110a/p85a), PI3Kb, (p110b/p85a), PI3Kd, (p110d/p85a), PI3Kg(p120g), PIM1, PIM2, PIM3, PKA, PKAcb, PKAcg, PKCa, PKCb1, PKCb2, PKCd, PKCepsilon, PKCeta, PKCg, PKCiota, PKCmu/PRKD1, PKCnu/PRKD3, PKCtheta, PKCzeta, PKD2/PRKD2, PKG1a, PKG1b, PKG2/PRKG2, PKN1/PRK1, PKN2/PRK2, PKN3/PRK3, PLK1, PLK2, PLK3, PLK4/SAK, PRKX, PYK2, RAF1, RET, RIPK2, RIPK3, RIPK5, ROCK1, ROCK2, RON/MST1R, ROS/ROS1, RSK1, RSK2, RSK3, RSK4, SGK1, SGK2, SGK3/SGKL, SIK1, SIK2, SLK/STK2, SNARK/NUAK2, SRMS, SSTK/TSSK6, STK16, STK22D/TSSK1, STK25/YSK1, STK32b/YANK2, STK32c/YANK3, STK33, STK38/NDR1, STK38L/NDR2, STK39/STLK3, SRPK1, SRPK2, SYK, TAK1, TAOK1, TAOK2/TAO1, TAOK3/JIK, TBK1, TEC, TESK1, TGFBR2, TIE2/TEK, TLK1, TLK2, TNIK, TNK1, TRKA, TRKB, TRKC, TRPM7/CHAK1, TSSK2, TSSK3/STK22C, TTBK1, TTBK2, TTK, TXK, TYK1/LTK, TYK2, TYRO3/SKY, ULK1, ULK2, ULK3, VRK1, VRK2, WEE1, WNK1, WNK2, WNK3, YES/YES1, ZAK/MLTK, ZAP70, ZIPK/DAPK3, KINASE, MUTANTS, ABL1(E255K), ABL1(F3171), ABL1(G250E), ABL1(H396P), ABL1 (M351T), ABL1(Q252H), ABL1(T3151), ABL1(Y253F), ALK (C1156Y), ALK(L1196M), ALK (F1174L), ALK (R1275Q), BRAF(V599E), BTK(E41K), CHK2(I157T), c-Kit(A829P), c-KIT(D816H), c-KIT(D816V), c-Kit (D820E), c-Kit(N822K), C-Kit (T670I), c-Kit(V559D), c-Kit(V559D/V654A), c-Kit(V559D/T670I), C-Kit (V560G), c-KIT(V654A), C-MET(D1228H), C-MET (D1228N), C-MET(F1200I), c-MET(M1250T), C-MET (Y1230A), C-MET(Y1230C), C-MET(Y1230D), C-MET (Y1230H), c-Src(T341M), EGFR(G719C), EGFR(G719S), EGFR(L858R), EGFR(L861Q), EGFR(T790M), EGFR, (L858R,T790M), EGFR(d746-750/T790M), EGFR(d746-750), EGFR(d747-749/A750P), EGFR(d747-752/P753S), EGFR(d752-759), FGFR1(V561M), FGFR2(N549H), FGFR3(G697C), FGFR3(K650E), FGFR3(K650M), FGFR4(N535K), FGFR4(V550E), FGFR4(V550L), FLT3 (D835Y), FLT3(ITD), JAK2 (V617F), LRRK2 (G2019S), LRRK2 (I2020T), LRRK2 (R1441C), p38a(T106M), PDG-FRa(D842V), PDGFRa(T674I), PDGFRa(V561D), RET (E762Q), RET(G691S), RET(M918T), RET(R749T), RET (R813Q), RET(V804L), RET(V804M), RET(Y791F), TIF2 (R849W), TIF2(Y897S), and TIF2(Y1108F).

In another aspect of the invention, the subject compounds may be administered in combination with one or more targeted anti-cancer agents that modulate non-kinase biological targets, pathway, or processes. Such targets pathways, or processes include but not limited to heat shock proteins (e.g. HSP90), poly-ADP (adenosine diphosphate)-ribose polymerase (PARP), hypoxia-inducible factors (HIF), proteasome, Wnt/Hedgehog/Notch signaling proteins, TNF-alpha, matrix metalloproteinase, farnesyl transferase, apoptosis pathway (e.g Bcl-xL, Bcl-2, Bcl-w), histone deacetylases (HDAC), histone acetyltransferases (HAT), and methyltransferase (e.g histone lysine methyltransferases, histone arginine methyltransferase, DNA methyltransferase, etc).

In another aspect of the invention, the compounds of the invention are administered in combination with one or more of other anti-cancer agents that include, but are not limited to, hormonal therapies (e.g Tamoxifen, Fulvestrant, Clomifene, Anastrozole, Exemestane, Formestane, Letrozole, etc), vascular disrupting agent, gene therapy, RNAi cancer therapy, chemoprotective agents (e.g., amfostine, mesna, and dexrazoxane), antibody conjugate (e.g brentuximab vedotin, ibritumomab tioxetan), cancer immunotherapy such as Interleukin-2, cancer vaccines (e.g., sipuleucel-T) or monoclonal antibodies (e.g., Bevacizumab, Alemtuzumab, Rituximab, Trastuzumab, etc).

In another aspect of the invention, the subject compounds are administered in combination with radiation therapy or surgeries. Radiation is commonly delivered internally (implantation of radioactive material near cancer site) or externally from a machine that employs photon (x-ray or gamma-ray) or particle radiation. Where the combination therapy further comprises radiation treatment, the radiation treatment may be conducted at any suitable time so long as a beneficial effect from the co-action of the combination of the therapeutic agents and radiation treatment is achieved. For example, in appropriate cases, the beneficial effect is still achieved when the radiation treatment is temporally removed from the administration of the therapeutic agents, perhaps by days or even weeks.

In certain preferred embodiments, the compounds of the invention are administered in combination with one or more of radiation therapy, surgery, or anti-cancer agents that include, but are not limited to, DNA damaging agents, anti-metabolites, topoisomerase inhibitors, anti-microtubule agents, EGFR inhibitors, HER2 inhibitors, VEGFR2 inhibitors, BRAF inhibitors, Bcr-Abl inhibitors, PDGFR inhibitors, ALK inhibitors, PLK inhibitors, MET inhibitors, epigenetic agents, HSP90 inhibitors, PARP inhibitors, CHK inhibitors, aromatase inhibitor, estrogen receptor antagonist, and antibodies targeting VEGF, HER2, EGFR, LD50, CD20, CD30, CD33, etc.

In certain preferred embodiments, the compounds of the invention are administered in combination with one or more of abarelix, abiraterone acetate, aldesleukin, alemtuzumab, altretamine, anastrozole, asparaginase, bevacizumab, bexarotene, bicalutamide, bleomycin, bortezomib, brentuximab vedotin, busulfan, capecitabine, carboplatin, carmustine, cetuximab, chlorambucil, cisplatin, cladribine, clofarabine, clomifene, crizotinib, cyclophosphamide, dasatinib, daunorubicin liposomal, decitabine, degarelix, denileukin diftitox, denileukin diftitox, denosumab, docetaxel, doxorubicin, doxorubicin liposomal, epirubicin, eribulin mesylate, erlotinib, estramustine, etoposide phosphate, everolimus, exemestane, fludarabine, fluorouracil, fotemustine, fulvestrant, gefitinib, gemcitabine, gemtuzumab ozogamicin, goserelin acetate, histrelin acetate, hydroxyurea, ibritumomab tiuxetan, idarubicin, ifosfamide, imatinib mesylate, interferon alfa 2a, ipilimumab, ixabepilone, lapatinib ditosylate, lenalidomide, letrozole, leucovorin, leuprolide acetate, levamisole, lomustine, mechlorethamine, melphalan, methotrexate, mitomycin C, mitoxantrone, nelarabine, nilotinib, oxaliplatin, paclitaxel, paclitaxel protein-bound particle, pamidronate, panitumumab, pegaspargase, peginterferon alfa-2b, pemetrexed disodium, pentostatin, raloxifene, rituximab, sorafenib, streptozocin, sunitinib maleate, tamoxifen, temsirolimus, teniposide, thalidomide, toremifene, tositumomab, trastuzumab, tretinoin, uramustine, vandetanib, vemurafenib, vinorelbine, zoledronate, radiation therapy, or surgery.

A wide variety of administration methods may be used in conjunction with the compounds of the present invention. Compounds of the present invention may be administered or coadministered orally, parenterally, intraperitoneally, intravenously, intraarterially, transdermally, sublingually, intramuscularly, rectally, transbuccally, intranasally, liposomally, via inhalation, vaginally, intraoccularly, via local delivery (for example by catheter or stent), subcutaneously, intraadiposally, intraarticularly, or intrathecally. The compounds according to the invention may also be administered or coadministered in slow release dosage forms. Compounds may be in gaseous, liquid, semi-liquid or solid form, formulated in a manner suitable for the route of administration to be used. For oral administration, suitable solid oral formulations include tablets, capsules, pills, granules, pellets, sachets and effervescent, powders, and the like. Suitable liquid oral formulations include solutions, suspensions, dispersions, emulsions, oils and the like. For parenteral administration, reconstitution of a lyophilized powder is typically used. Tablets and iv infusion may be preferred.

The invention further provides methods for the prevention or treatment of a neoplastic disease or immune disease. In one embodiment, the invention relates to a method of treating a neoplastic disease or immune disease in a subject in need of treatment comprising administering to said subject a therapeutically effective amount of a compound of the invention. In one embodiment, the invention further provides for the use of a compound of the invention in the manufacture of a medicament for halting or decreasing a neoplastic disease or immune disease.

The neoplastic disease includes but not limited to lung cancer, head and neck cancer, central nervous system cancer, prostate cancer, testicular cancer, colorectal cancer, pancreatic cancer, liver cancer, stomach cancer, biliary tract cancer, esophageal cancer, gastrointestinal stromal tumor, breast cancer, cervical cancer, ovarian cancer, uterine cancer, leukemia, lymphomas, multiple myeloma, melanoma, basal cell carcinoma, squamous cell carcinoma, bladder cancer, renal cancer, sarcoma, mesothelioma, thymoma, myelodysplastic syndrome and myeloproliferative disease.

In certain embodiments, the neoplastic disease is a solid tumor. Representative treatable solid tumors include melanoma, breast cancer, lung cancer (e.g., small cell lung cancer (SCLC), or non-small cell lung cancer (NSCLC)), colon cancer, renal cancer, or sarcoma.kyl In certain embodiments, the method may further include administering a second therapeutic agent known to be effective for treating the solid tumor.

For example, effective second therapeutic agent known to be effective for treating breast cancer includes: Methotrexate (Abitrexate, Folex, Folex PFS, Methotrexate LPF, Mexate-AQ); Paclitaxel (Taxol); Paclitaxel Albumin-stabilized Nanoparticle Formulation (Abraxane); Doxorubicin Hydrochloride (Adriamycin, Adriamycin PFS; Adriamycin RDF); Fluorouracil (Adrucil, Efudex, Fluoroplex); Everolimus (Afinitor); Anastrozole (Arimidex); Exemestane (Aromasin); Capecitabine (Xeloda); Cyclophosphamide (Clafen, Cytoxan, Neosar); Docetaxel (Taxotere); Epirubicin Hydrochloride (Ellence); Everolimus; Toremifene (Fareston); Fulvestrant (Faslodex); Letrozole (Femara); Gemcitabine Hydrochloride (Gemzar); Trastuzumab (Herceptin); Ixabepilone (Ixempra); Lapatinib Ditosylate; Tamoxifen Citrate (Nolvadex, Novaldex); Pertuzumab (Perjeta); Toremifene; Lapatinib Ditosylate (Tykerb); Doxorubicin Hydrochloride & Cyclophosphamide; Doxorubicin Hydrochloride & Cyclophosphamide & Paclitaxel; Doxorubicin Hydrochloride & Cyclophosphamide & Fluorouracil; Cyclophosphamide & Methotrexate & Fluorouracil; Fluorouracil & Cyclophosphamide & Epirubicin Hydrochloride.

Effective second therapeutic agent known to be effective for treating small cell lung cancer (SCLC) includes: Methotrexate (Abitrexate, Folex, Folex PFS, Methotrexate LPF, Mexate, Mexate-AQ); Etoposide (Toposar, VePesid); Etoposide Phosphate (Etopophos); Topotecan Hydrochloride (Hycamtin).

Effective second therapeutic agent known to be effective for treating non-small cell lung cancer (NSCLC) includes: Methotrexate (Abitrexate, Folex, Folex PFS, Methotrexate LPF, Mexate, Mexate-AQ); Paclitaxel (Taxol); Paclitaxel Albumin-stabilized Nanoparticle Formulation (Abraxane); Pemetrexed Disodium (Alimta); Bevacizumab (Avastin); Carboplatin (Paraplat, Paraplatin); Cisplatin (Platinol, Platinol-AQ); Crizotinib (Xalkori); Erlotinib Hydrochloride; Gefitinib (Iressa); Gemcitabine Hydrochloride (Gemzar); Pemetrexed Disodium; Erlotinib Hydrochloride (Tarceva); Carboplatin & Paclitaxel; Gemcitabine Hydrochloride & Cisplatin.

Other than the standard surgical treatment, effective second therapeutic agent known to be effective for treating melanoma includes: imiquimod (Zyclara, Aldara, Beselna, R-837); interferon (adjuvant therapy after surgery); Bacille Calmette-Guerin (BCG) vaccine; interleukin-2; Ipilimumab (Yervoy); Vemurafenib (Zelboraf); Dacarbazine (DTIC); Temozolomide (Temodar); interferon & temozolomide; interferon, interleukin-2, and temozolomide; or isolated limb perfusion (ILF, infusing the limb with a heated solution of chemotherapy), depending on the specific stages of the melanoma at the time of diagnosis.

Effective second therapeutic agent known to be effective for treating colon cancer includes: Fluorouracil (Adrucil, Efudex, Fluoroplex); Bevacizumab (Avastin); Irinotecan Hydrochloride (Camptosar); Capecitabine (Xeloda); Cetuximab (Erbitux); Oxaliplatin (Eloxatin); Leucovorin Calcium; Panitumumab (Vectibix); Regorafenib (Stivarga); Leucovorin Calcium (Wellcovorin); Ziv-Aflibercept (Zaltrap); Leucovorin Calcium & Fluorouracil & Irinotecan Hydrochloride; Leucovorin Calcium & Fluorouracil & Irinotecan Hydrochloride+Bevacizumab; Leucovorin Calcium (Folinic Acid) & Fluorouracil & Oxaliplatin; Capecitabine & Oxaliplatin.

Effective second therapeutic agent known to be effective for treating renal cancer includes: Fluorouracil (Adrucil, Efudex, Fluoroplex); Bevacizumab (Avastin); Irinotecan Hydrochloride (Camptosar); Cetuximab (Erbitux); Panitumumab (Vectibix); Regorafenib (Stivarga); Ziv-Aflibercept (Zaltrap); Capecitabine & Oxaliplatin; Leucovorin Calcium (Folinic Acid) & Fluorouracil & Irinotecan Hydrochloride; Leucovorin Calcium & Fluorouracil & Irinotecan Hydrochloride+Bevacizumab; Leucovorin Calcium (Folinic Acid) & Fluorouracil & Oxaliplatin.

Preferred combinations of compounds of the invention, especially in combination with CY-102 or a pharmaceutically acceptable salt, solvate or polymorph thereof include combinations with:

Proteasome inhibitors (e.g. bortezomib, carfilzomib).
IMIDs (e.g. Thalidomide, lenalidomide, pomalidomide).
Platinum agents (e.g. cisplatin, carboplatin).
Folate antagonists (e.g. pemetrexed, pralatrexate).
CD30 antibodies and conjugates (e.g. brentuximab, vendotin).
Antibodies (also conjugated) to treat haematological malignancies like anti CD20 (e.g. ofatumumab, rituximab, GA101, etc).
B-cell receptor antagonists (e.g. ibrutinib).
PI3K antagonists (e.g. GS1101 or IPI145).
BTK inhibitors.
Taxanes (e.g. taxol, paclitaxel).
Antibodies (also conjugated) to treat ovarian cancer (e.g. alpha folate receptor mabs, CA125 antibodies).
Antibodies to treat multiple myeloma (e.g. elotuzumab, anti CD38 mabs).
Anthracyclines (e.g. doxorubicin, idarubicin).
Nucleoside analogues (purine antagonists) like cytarabine, fludarabine, gemcitabine.
PNP antagonists (e.g. forodesine).
Bcr-abl tyrosinekinase blockers (e.g. imatinib, dasatinib, ponatinib, nilotinib).
mTor antagonists (e.g. temsirolimus, everolimus).
Agents influencing the CD40 activation (e.g. CD40 antagonists, CD40 gene medicines).
Multi tyrosine kinase antagonists (e.g. sorafenib, axitinib).
Bifunctional antibodies (e.g. CD19/CD3, also conjugated, also recognising other CD epitopes).

Preferred combinations of compounds of the invention, especially in combination with CY-102 or a pharmaceutically acceptable salt, solvate or polymorph thereof include combinations with one or more, such as one, two or three, of the above-identified therapeutic agents.

Especially preferred combinations of compounds of the invention include combinations of CY-102 or a pharmaceutically acceptable salt, solvate or polymorph thereof and forodesine, optionally in combination with one or more, such as one, two or three, of the above-identified therapeutic agents.

The combinations of compounds of the invention include combinations of CY-102 or a pharmaceutically acceptable salt, solvate or polymorph thereof and forodesine, optionally in combination with one or more, such as one, two or three, of the above-identified therapeutic agents.

The treatment above may be in conjunction with other treatments, such as surgery, radiation therapy, laser therapy, stem cell transplant.

In a further aspect, the present invention is directed to combinations of one or more compounds of the invention with one or more additional therapeutic agents. In a further aspect, the present invention is directed to combinations of one or more compounds of the invention with one or more additional therapeutic agents for use as a medicament, and in particular, for use in the treatment of the diseases disclosed herein. In a further aspect, the present invention is directed to the use of combinations of one or more compounds of the invention with one or more additional therapeutic agents in the treatment of the diseases disclosed herein. In preferred embodiments of all aspects of the invention, the disease to be treated is CLL.

In a further aspect, the present invention is directed to a kit comprising (a) a first pharmaceutical composition comprising one or more compounds of the present invention and (b) a second pharmaceutical composition comprising one or more additional therapeutic agents as defined herein. In a further aspect, the present invention is directed to a kit comprising (a) a first pharmaceutical composition comprising one or more compounds of the present invention and (b) a second pharmaceutical composition comprising one or more additional therapeutic agents as defined herein for use as a medicament, and in particular, for use in the treatment of the diseases disclosed herein. In a further aspect, the present invention is directed to a kit comprising (a) a first pharmaceutical composition comprising one or more compounds of the present invention and (b) a second pharmaceutical composition comprising one or more additional therapeutic agents as defined herein in the treatment of the diseases disclosed herein. In preferred embodiments of all aspects of the invention, the disease to be treated is CLL.

In a further aspect, the present invention is directed to a product containing a compound of formula (I) as defined herein, or a tautomer thereof or a pharmaceutically acceptable salt, solvate or polymorph of said compound or tautomer, and one or more other therapeutic agents as defined herein, as a combined preparation for simultaneous, separate or sequential use in treating a neoplastic disease or an immune disease.

It is well known that immunosuppression is one of major side-effect of many conventional chemotherapeutics. For example, at low dose, cyclophosphamide can be used to treat immune diseases such as multiple sclerosis, rheumatoid arthritis and the suppression of transplant rejections (Emadi A, et al, *Nat Rev Clin Oncol.* 2009 November; 6(11):638-47; Perini P, et al. *Neurol Sci.* 2008 September; 29 Suppl 2:S233-4) and is also widely used in bone marrow transplantation "conditioning" and "mobilization" regimens, and for the treatment of refractory severe autoimmune conditions, such as systemic lupus erythematosus (SLE), minimal change disease, severe rheumatoid arthritis, Wegener's granulomatosis (with trade name Cytoxan), scleroderma, and multiple sclerosis (with trade name Revimmune). In addition, HDAC has recently emerging as a promising target for treating immune disease [Szyf M. *Clin Rev Allergy Immunol.* 2010 August; 39(1):62-77]. The compounds of present invention may therefore be used for treatment of an immune disease.

In a preferred embodiment, the immune disease is selected from the group consisting of the rejection of transplanted organs and tissues, a graft-versus-host disease, a non-autoimmune inflammatory disease, and an autoimmue disease, wherein said autoimmue disease is selected from the group consisting of acute disseminated encephalomyelitis, addison's disease, ankylosing spondylitis, antiphospholipid antibody syndrome, autoimmune hemolytic anemia, autoimmune hepatitis, autoimmune inner ear disease, bullous pemphigoid, coeliac disease, chagas disease, chronic obstructive pulmonary disease, churg-strauss syndrome, dermatomyositis, Crohn's disease, diabetes mellitus type 1, endometriosis, goodpasture's syndrome, graves' disease, guillain-barré syndrome, hashimoto's disease, hidradenitis suppurativa, idiopathic thrombocytopenic purpura, interstitial cystitis, lupus erythematosus, morphea, multiple sclerosis, myasthenia gravis, narcolepsy, neuromyotonia, pemphigus vulgaris, pernicious anaemia, polymyositis, primary biliary cirrhosis, psoriasis, psoriatic arthritis, rheumatoid arthritis, schizophrenia, scleroderma, temporal arteritis, vasculitis, vitiligo, and wegener's granulomatosis.

It should be understood that the invention is not limited to the particular embodiments shown and described herein, but that various changes and modifications may be made without departing from the spirit and scope of the invention as defined by the claims.

General Synthetic Methods

The compounds according to the present invention may be synthesized according to a variety of reaction schemes. Necessary starting materials may be obtained by standard procedures of organic chemistry. The compounds and processes of the present invention will be better understood in connection with the following representative synthetic schemes and examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, and/or methods of the invention may be made without departing from the spirit of the invention and the scope of the appended claims.

A typical approach using Z $(CH_2)_p$ as an example to illustrate the synthesis of the Formula (III) compounds is described in Scheme 1. $X_1$ and $R_d$ in general Scheme 1 are the same as those described in the Summary section above,

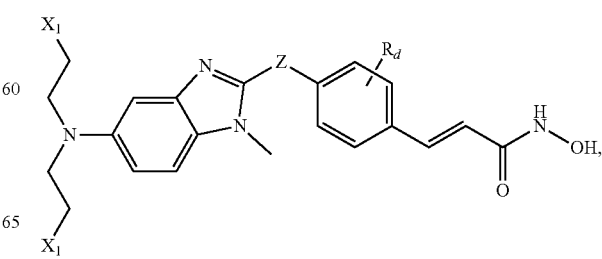

Formula (III)

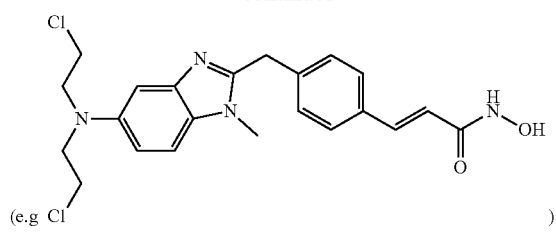

(e.g Cl),

Scheme 1

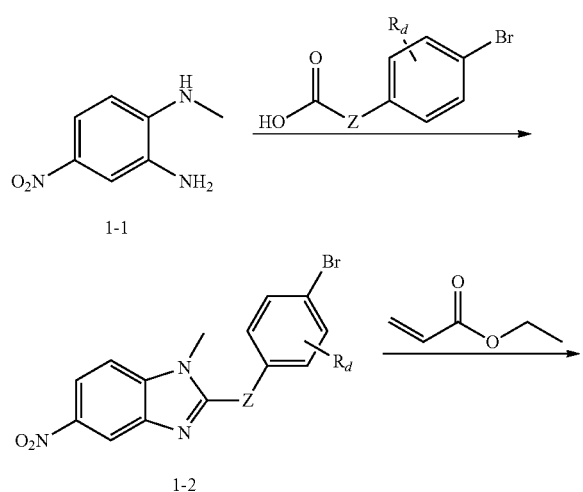

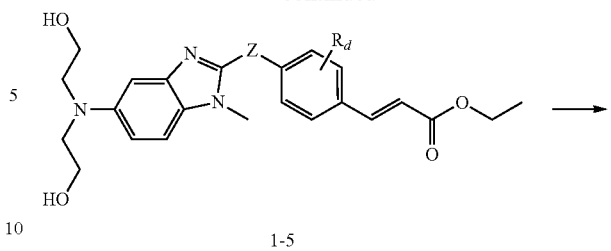

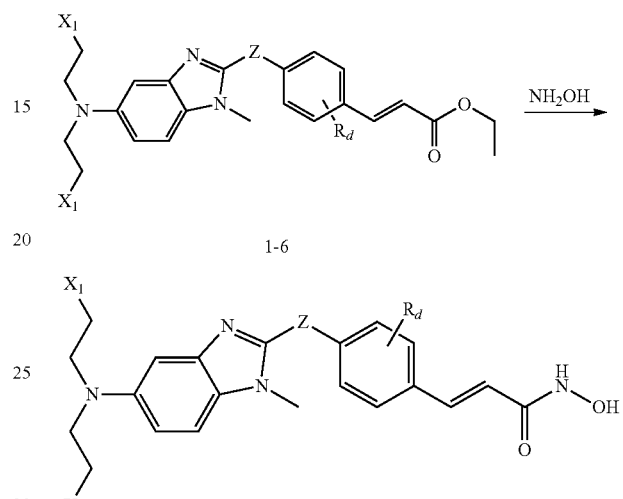

Formula (III)

The commercially available starting material 1-1 (CAS#: 41939-61-1) can react with appropriate carboxylic acid to form the benzimidazole intermediate 1-2, which can react with methyl acrylate by a Pd-catalyzed coupling to afford the cinnamate intermediate 1-3. The intermediate (1-3) can be subsequently reduced, for example with $H_2$, Pd/C, to an amino-substituted intermediate (1-4), which can react with oxirane to easily afford intermediate (1-5). After that, intermediate 1-5 can be converted to intermediate (1-6) with high yield by reaction with a chlorinating reagent such as thionyl chloride or phosphorus pentachloride. Finally the hydroxylamination of intermediate (1-6) in $NH_2OH$ can afford the target compounds.

Alternatively, Formula (III) compounds can be synthesized according to the general Scheme 1A. $X_1$ and $R_d$ in general Scheme 1A are the same as those described in the Summary section above.

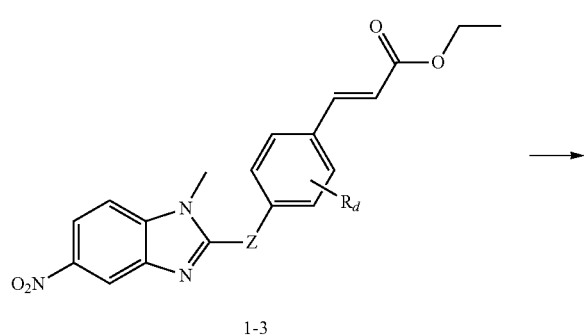

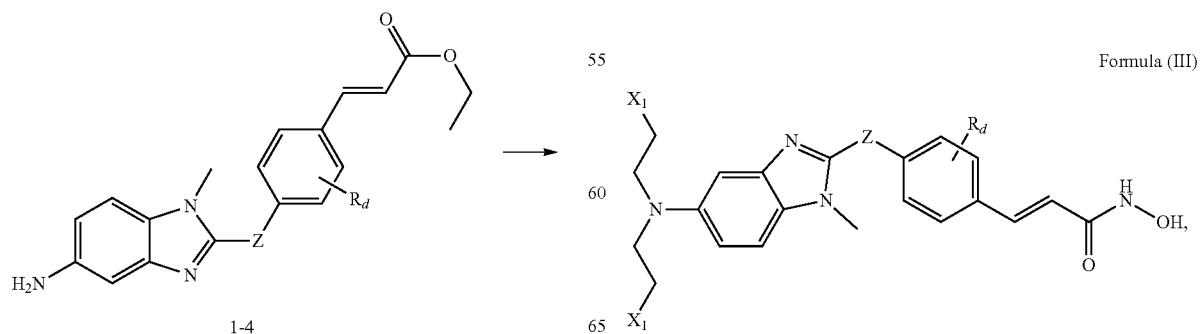

Formula (III)

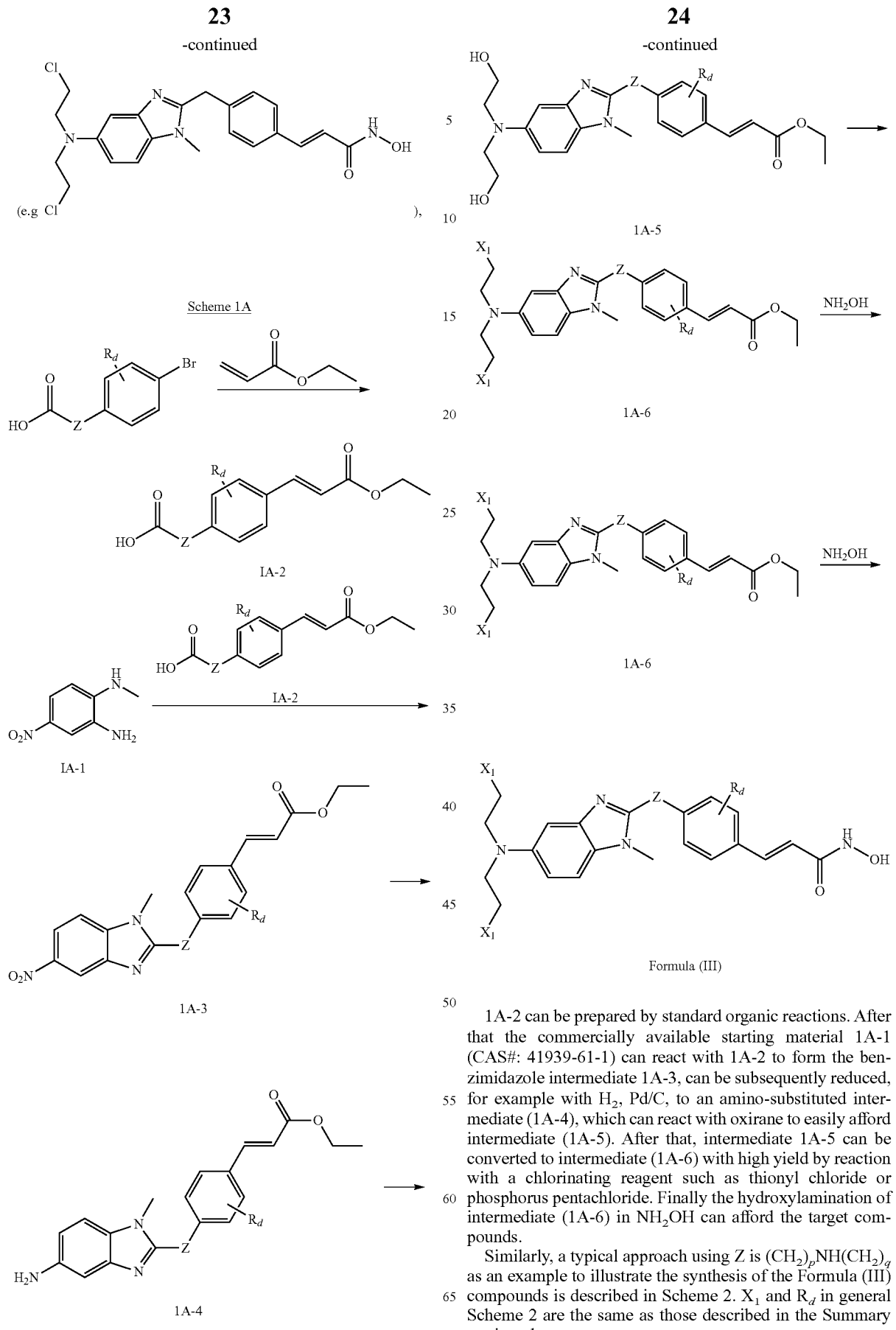

1A-2 can be prepared by standard organic reactions. After that the commercially available starting material 1A-1 (CAS#: 41939-61-1) can react with 1A-2 to form the benzimidazole intermediate 1A-3, can be subsequently reduced, for example with $H_2$, Pd/C, to an amino-substituted intermediate (1A-4), which can react with oxirane to easily afford intermediate (1A-5). After that, intermediate 1A-5 can be converted to intermediate (1A-6) with high yield by reaction with a chlorinating reagent such as thionyl chloride or phosphorus pentachloride. Finally the hydroxylamination of intermediate (1A-6) in $NH_2OH$ can afford the target compounds.

Similarly, a typical approach using Z is $(CH_2)_p NH(CH_2)_q$ as an example to illustrate the synthesis of the Formula (III) compounds is described in Scheme 2. $X_1$ and $R_d$ in general Scheme 2 are the same as those described in the Summary section above.

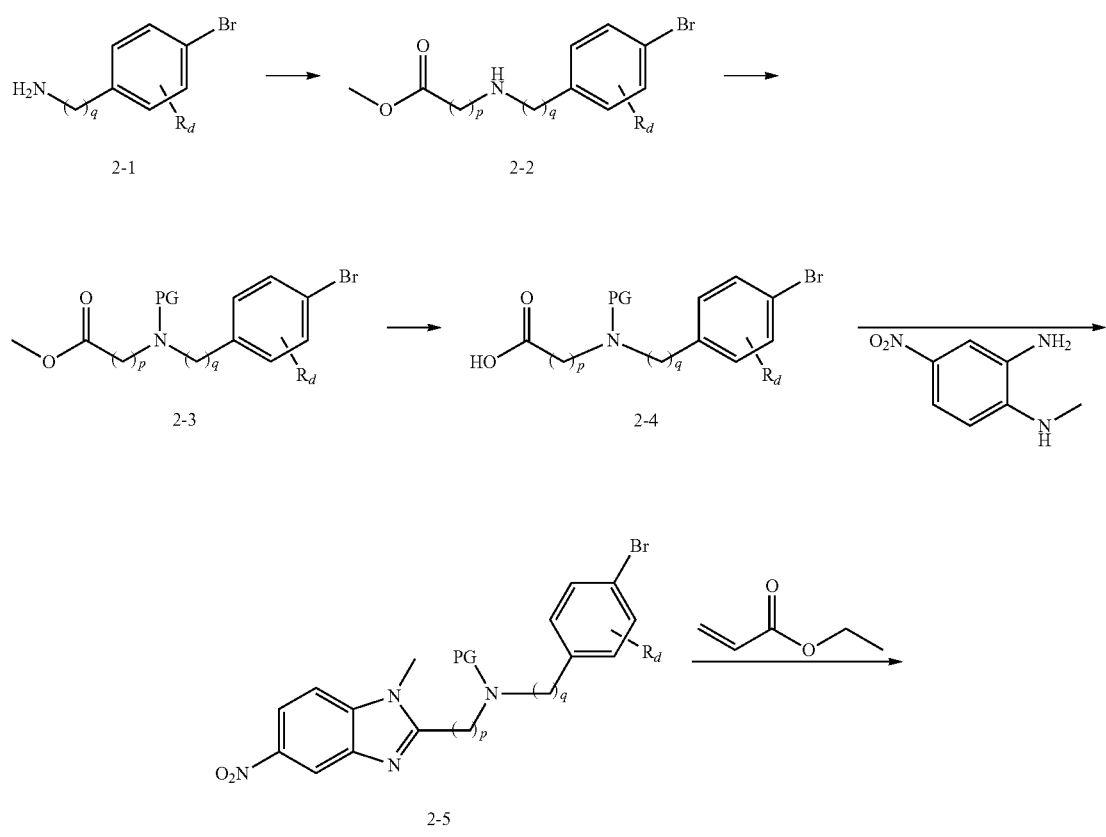

-continued
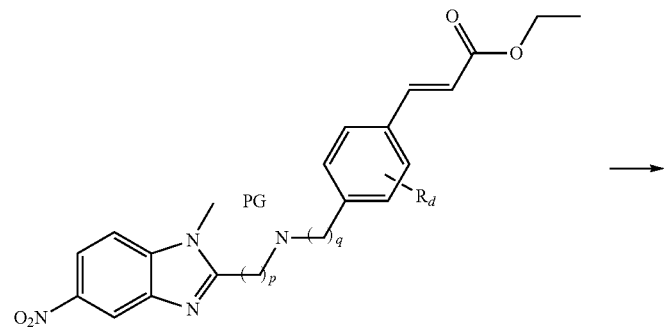
2-6
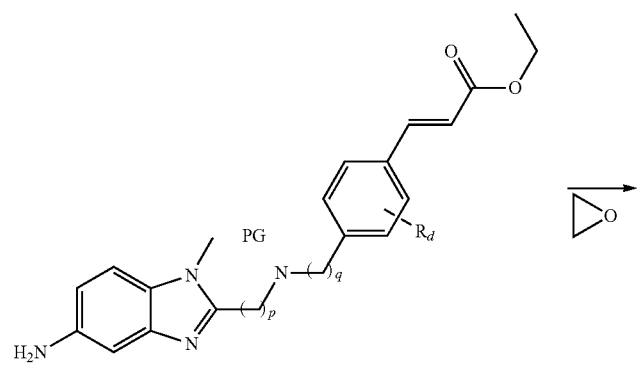
2-7
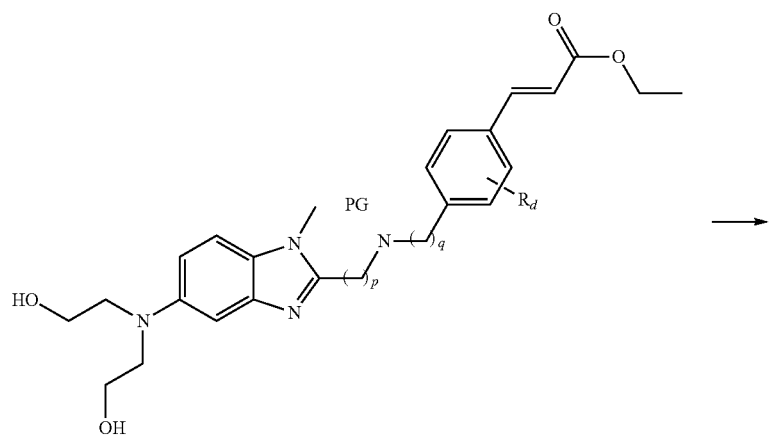
2-8

-continued

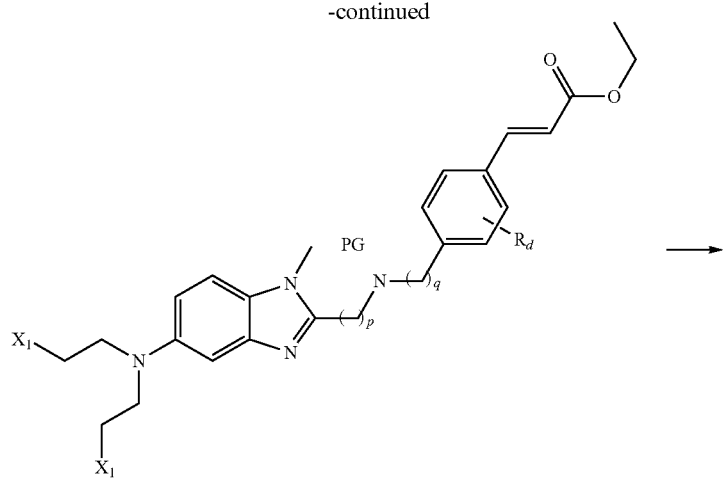

2-9

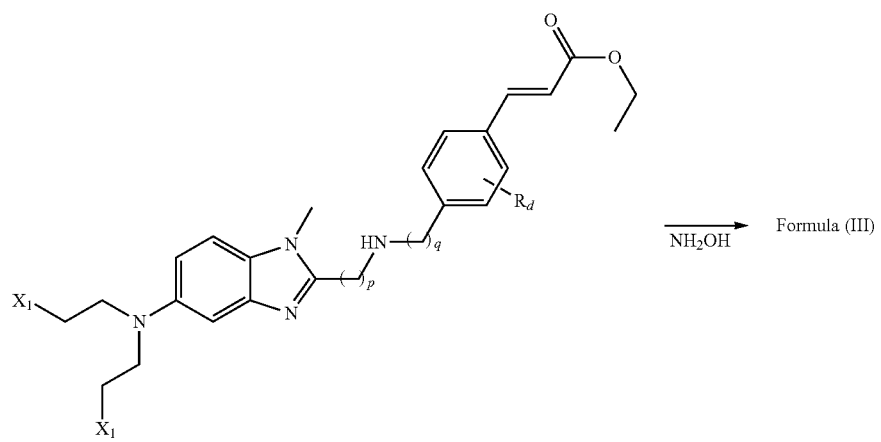

2-10

The starting material 2-1 can be converted to 2-2 by standard organic reactions. The secondary amine of intermediate (2-2) can be protected by a protecting group (-PG) such as Boc to yield intermediate (2-3), which undergo hydrolysis to afford the carboxylic acid intermediate 2-4. After that, 2-4 can react with $N^1$-methyl-4-nitrobenzene-1,2-diamine to form the benzimidazole intermediate 2-5, which can react with methyl acrylate by a Pd-catalyzed coupling to afford the cinnamate intermediate 2-6. The intermediate 2-6 can be subsequently reduced, for example Fe/$NH_4$Cl, Fe/HCl or Zn/$FeSO_4$, to an amino-substituted intermediate (2-7), which can react with oxirane to easily afford intermediate (2-8). After that 2-8 can be converted to intermediate (2-9) with high yield by reaction with a chlorinating reagent such as thionyl chloride or phosphorus pentachloride. The de-protection of intermediate (2-9) affords the intermediate 2-10. Finally the hydroxylamination of 2-10 in $NH_2OH$ can afford the target compounds of Formula (III).

Alternatively, Formula (III) compounds can be synthesized according to the Scheme $2^a$. $X_1$ and $R_d$ in general Scheme $2^a$ are the same as those described in the Summary section above.

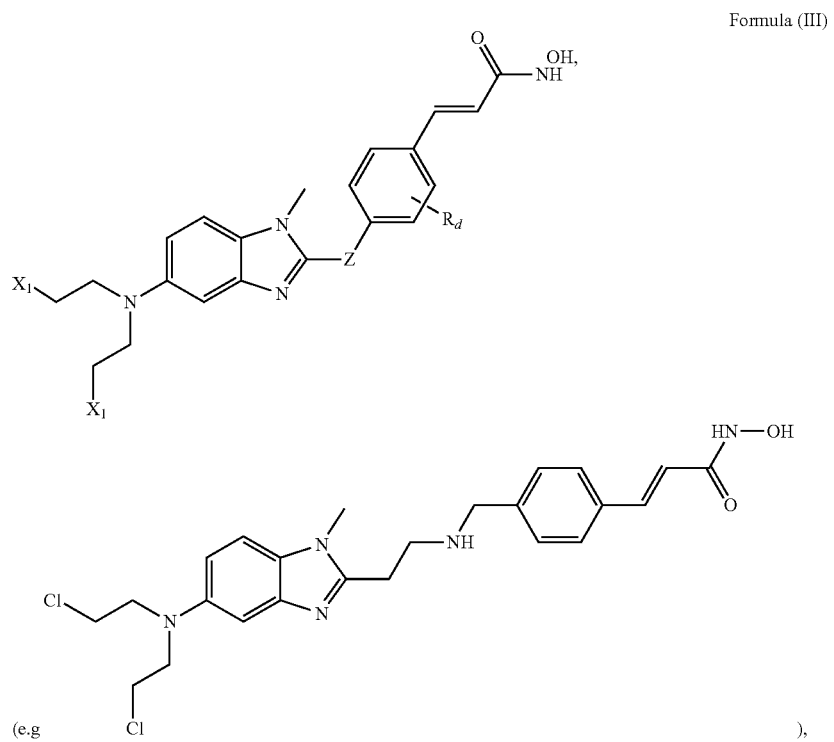
Formula (III)
(e.g ),
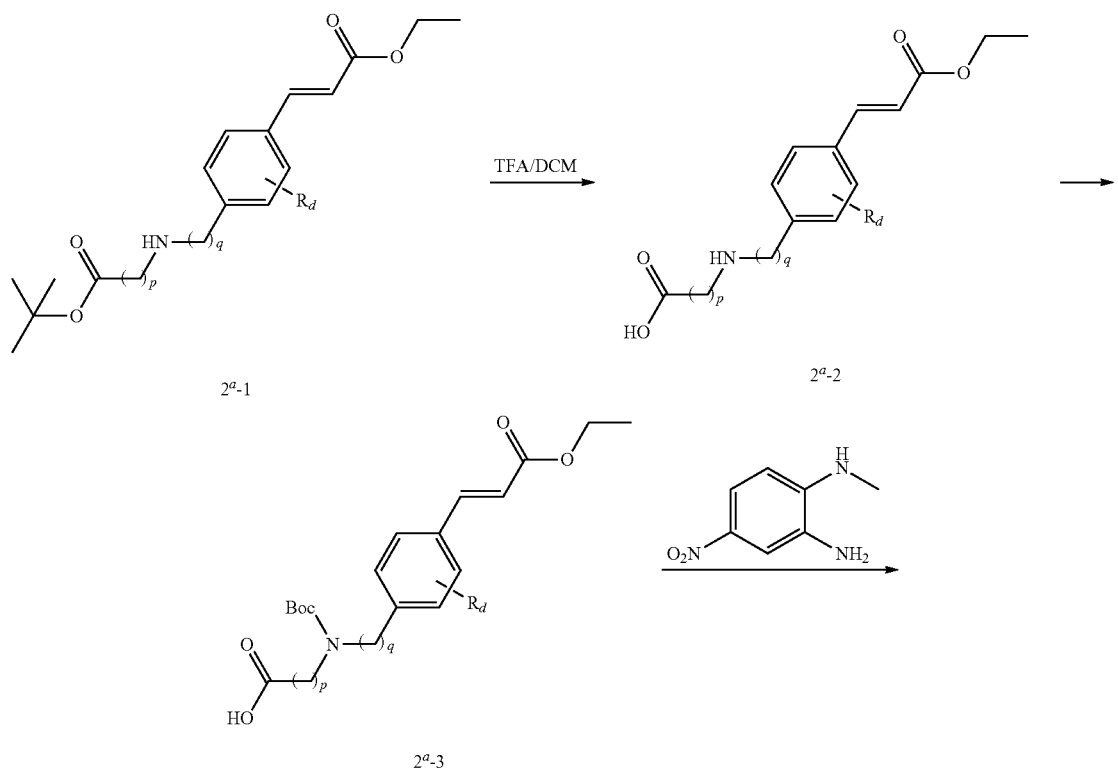
Scheme 2ª

-continued
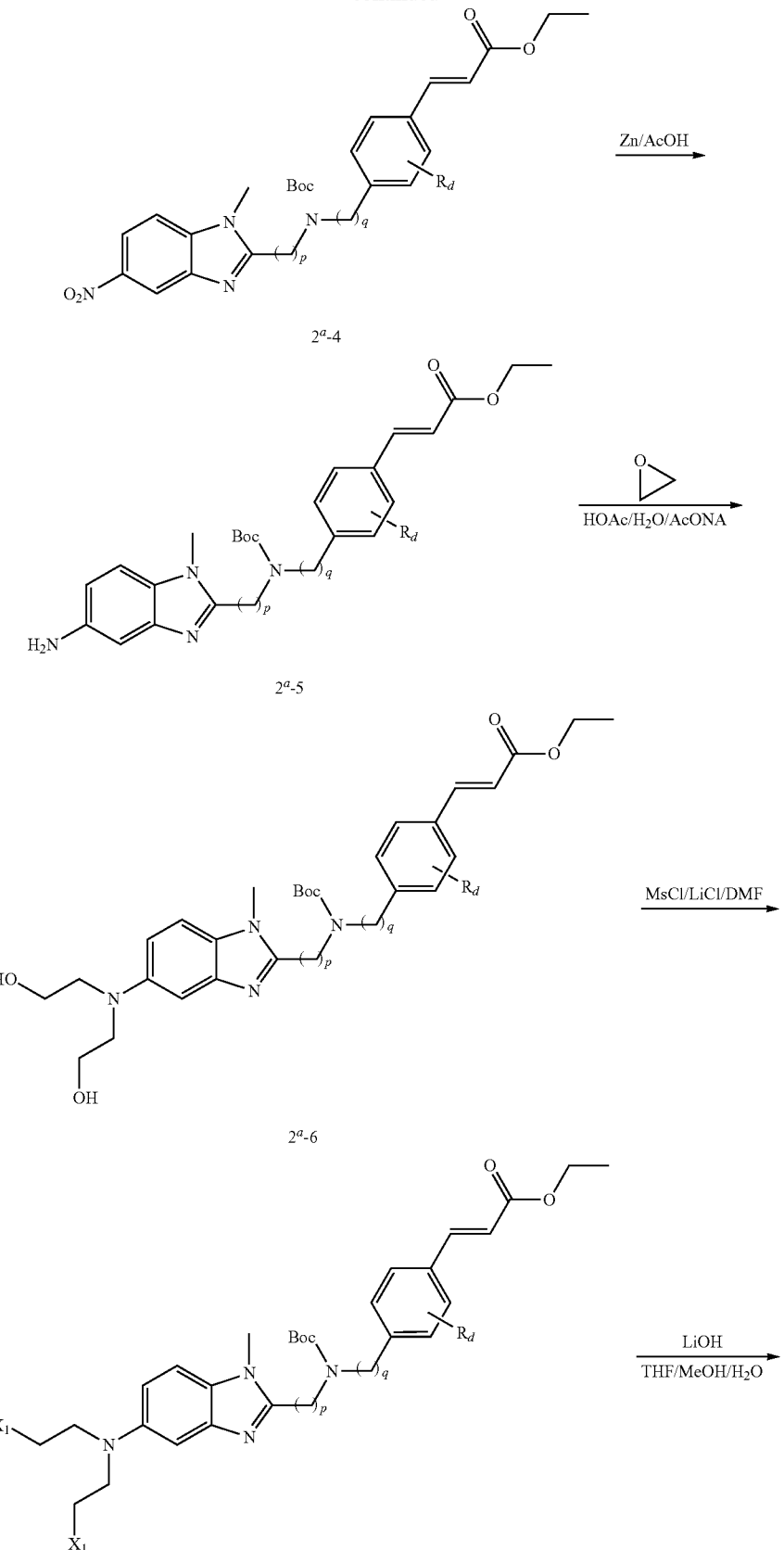

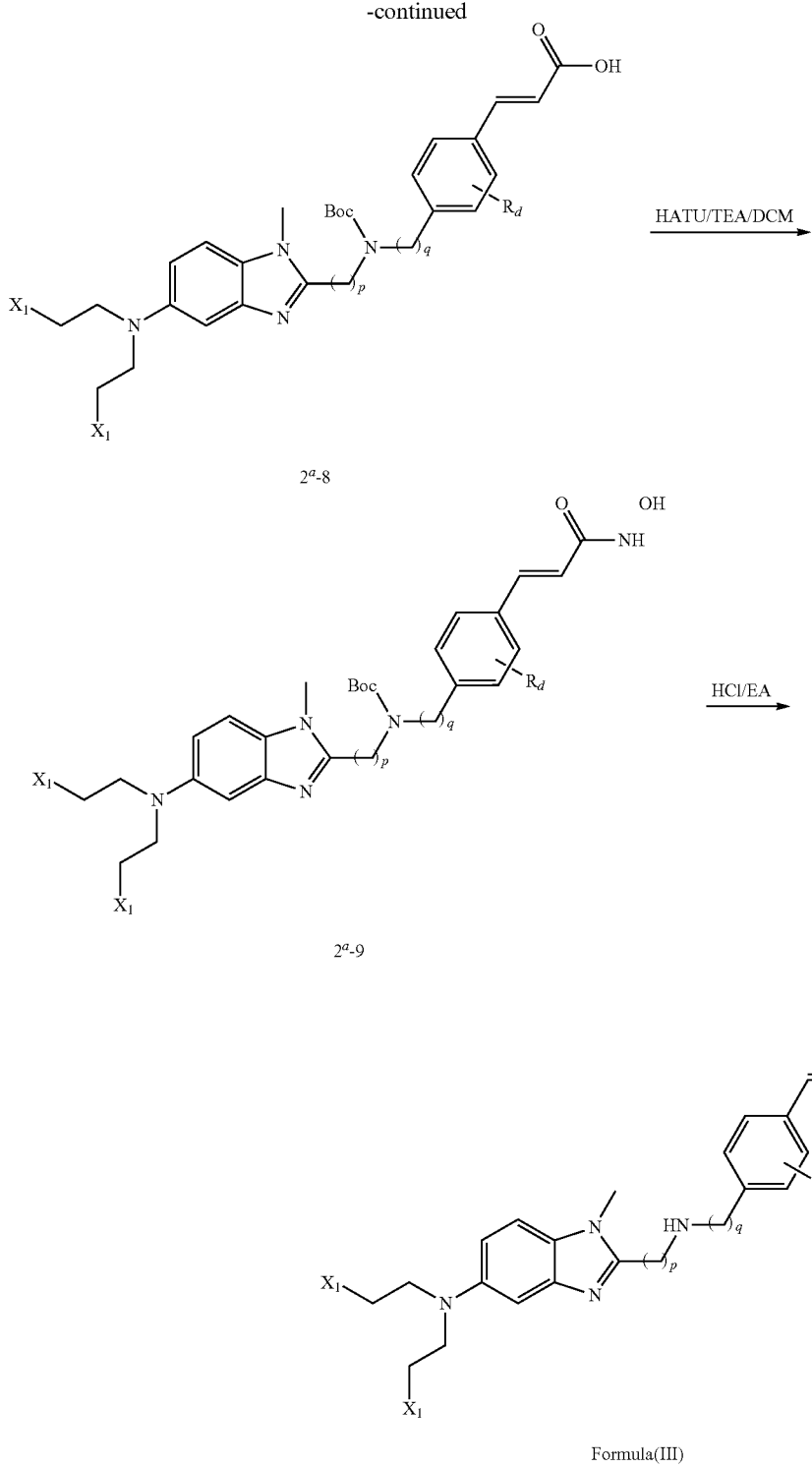

Formula(III)

The staring material $2^a$-1 with different p and q can be prepared by standard organic reactions. After that, $2^a$-1 can be converted to carboxylic acid intermediate $2^a$-2 with TFA. The secondary amine of intermediate $2^a$-2 can be protected by a protecting group such as Boc to yield intermediate $2^a$-3, which can react with $N^1$-methyl-4-nitrobenzene-1,2-diamine to form the benzimidazole intermediate $2^a$-4. Next, the intermediate $2^a$-4 can be subsequently reduced, for example Zn/AcOH, Fe/NH$_4$Cl, Fe/HCl or Zn/FeSO$_4$, to an amino-substituted intermediate ($2^a$-5), which can react with oxirane to easily afford alcohol intermediate ($2^a$-6). After that $2^a$-6 can be converted to intermediate ($2^a$-7) with high yield by reaction with a chlorinating reagent such as thionyl chloride, MsCl/LiCl, or phosphorus pentachloride. The hydrolysis of ester $2^a$-7, e.g. in LiOH will afford carboxylic acid intermediate $2^a$-8, which can couple with NH$_2$OH to form the hydroxamic acid intermediate $2^a$-9. Finally, the de-protection of $2^a$-9 afford the target compounds of Formula (III).
As a further example, the several different approaches to synthesize CY-102 are described in the following scheme 2A:
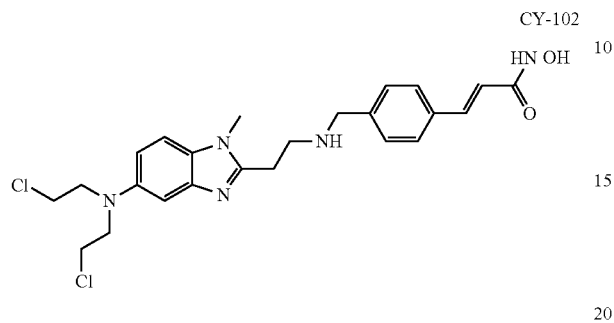

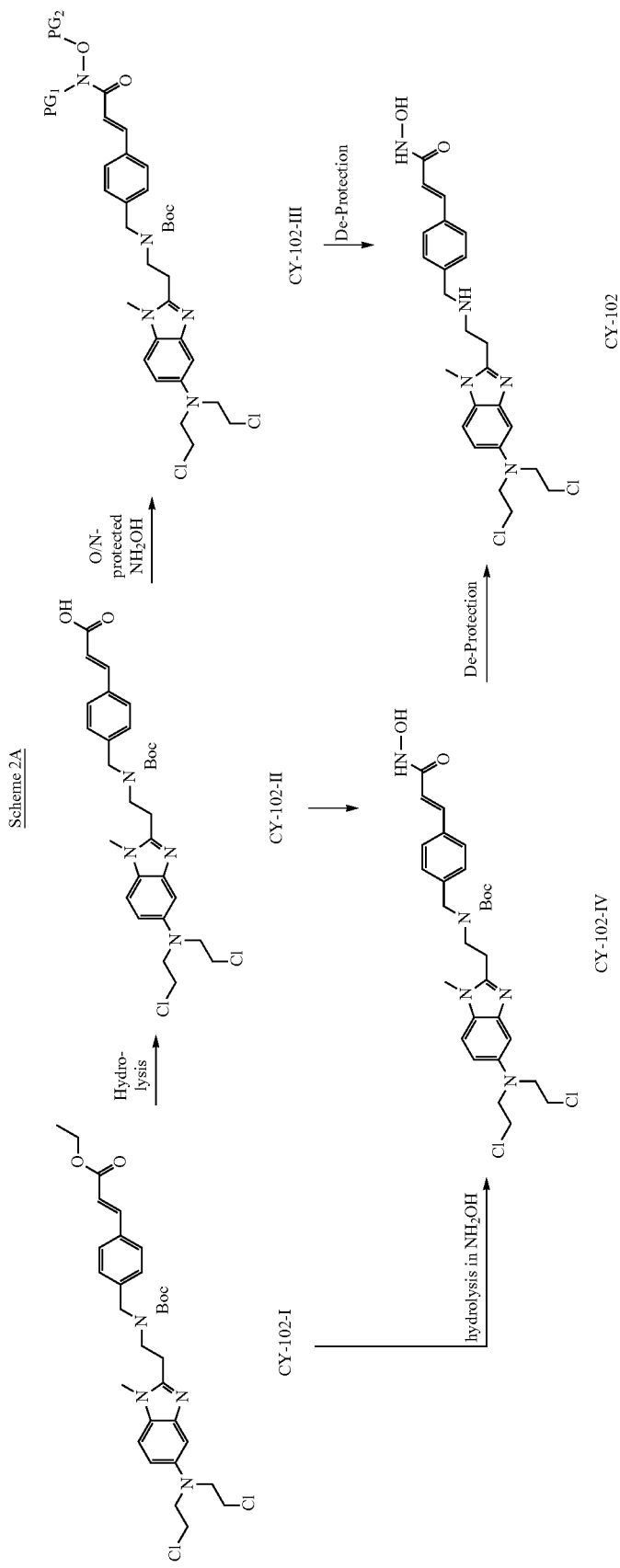

As showed in Scheme 2A, CY-102-IV can be prepared by reacting CY-102-I with hydroxylamine, in the presence of a base such as for example potassium hydroxide. Said reaction is performed in an appropriate solvent, such as, for example, methanol. Finally, the de-Boc of CY-102-IV will lead to CY-102.

Another route showed in Scheme 2A for the preparation of CY-102 is follows: first, the hydrolysis of CY-102-I, e.g in LiOH or HCl to afford the carboxylic acid intermediate CY-102-II; next, CY-102-II can either couple with NH$_2$OH at the presence of appropriate reagents such as HATU/TEA/DCM to form CY-102-IV or can be converted CY-102-IV by such as the method reported in Tetrahedron Letters, 41, (2000), 6285-6288; finally, the de-Boc of CY-102-IV will lead to CY-102.

Alternative route to prepare CY-102 is first to hydrolyze CY-102-I e.g in LiOH or HCl to afford the carboxylic acid intermediate CY-102-II, which can coupled with 0 or N-protected hydroxylamine such as NH$_2$—O-THP, NH$_2$—O-Bn, N-t-Boc-O-THP, N-t-Boc-O-TBDMS, N,O-bis-(phenoxycarbonyl)-hydroxylamine, N,O-bis(tert-butoxycarbonyl)hydroxylamine, and N,N,O-tris-(trimethylsilyl)-hydroxylamine to form intermediate CY-102-III. For example, CY-102-II can couple with NH$_2$—O-THP in the presence of appropriate reagents such as N$^1$-(ethylcarbonimidoyl)-N,N-dimethyl-1,3-propanediamine, monohydrochloride (EDC) and 1-hydroxy-1H-benzotriazole (HOBT) to form intermediate CY-102-III. This reaction may be performed in the presence of a base such as triethylamine, in a suitable solvent, such as, a mixture of dichloromethane and tetrahydrofuran. Finally CY-102 can be prepared by deprotecting CY-102-III with an appropriate reagents, such as for example, trifluoro acetic acid. Said reaction is performed in an appropriate solvent, such as, for example, methanol or dichloromethane.

The approaches to synthesize the intermediate CY-102-I

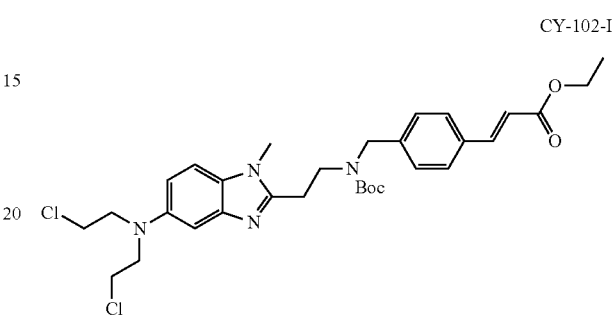

CY-102-I are described in Scheme 2B-2C.

Scheme 2B

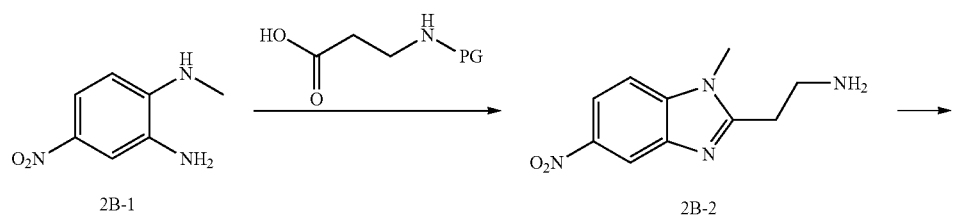

2B-1    2B-2

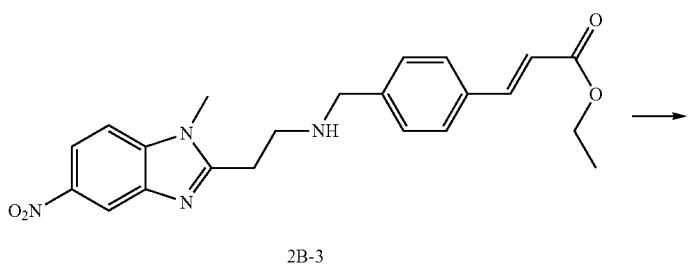

2B-3

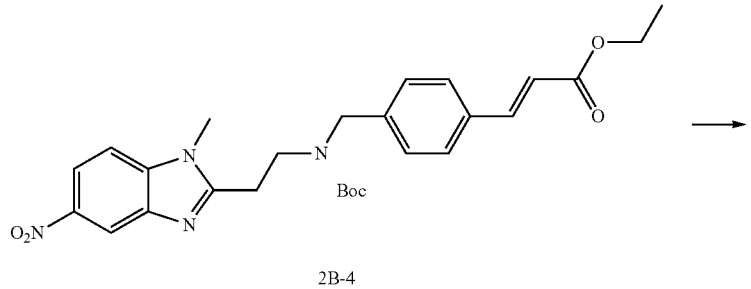

2B-4

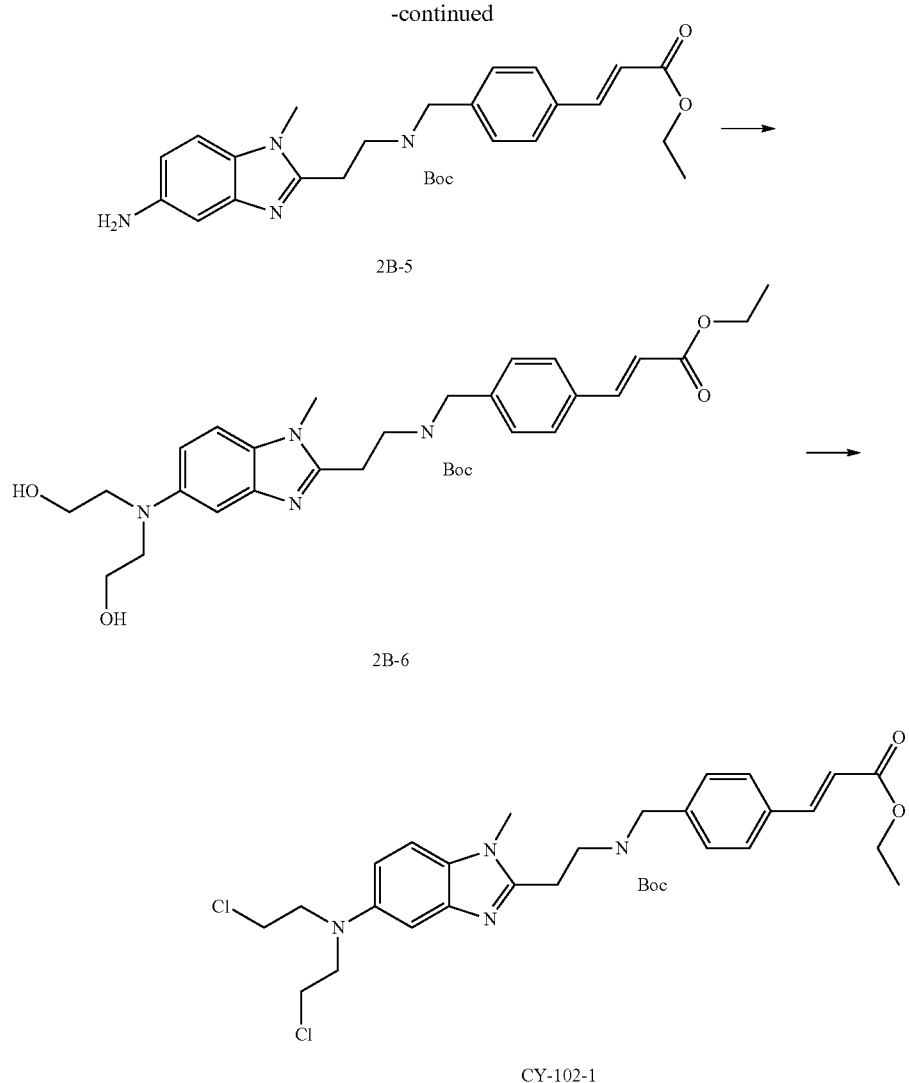

The commercially available starting material 2B-1 (CAS#: 41939-61-1) react with amine protected 3-aminopropanoic acid followed by a deprotection process to form the benzimidazole intermediate 2B-2, which can react with (E)-methyl 3-(4-formylphenyl)acrylate to afford the cinnamate intermediate 2B-3. The secondary amine of intermediate (2B-3) can be protected by a protecting group (-PG) such as Boc to yield intermediate (2B-4), which can be subsequently reduced, for example by Fe/NH$_4$Cl, Fe/HCl or Zn/FeSO$_4$, to an amino-substituted intermediate (2B-5). Intermediate 2B-5 can react with oxirane to easily afford intermediate (2B-6) which can be converted to intermediate (CY-102-I) with high yield by reaction with a chlorinating reagent such as thionyl chloride or phosphorus pentachloride.

Scheme 2C

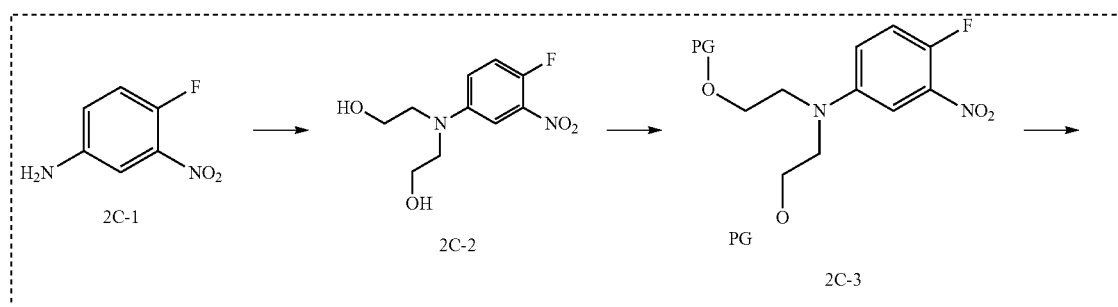

-continued
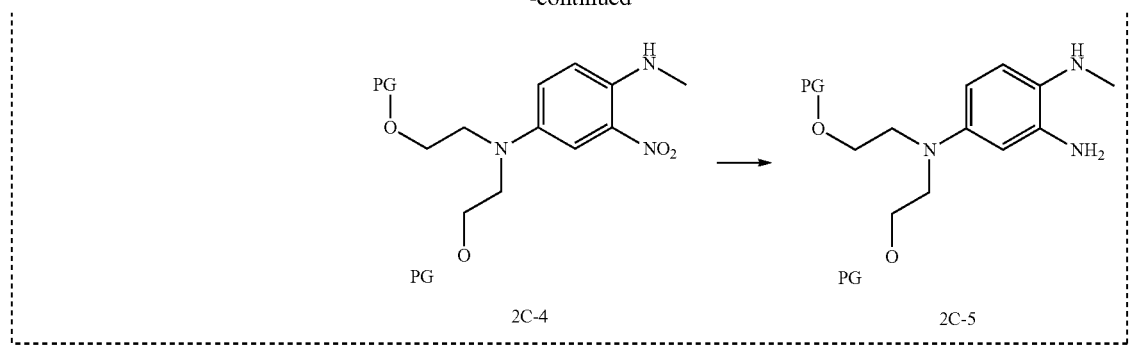
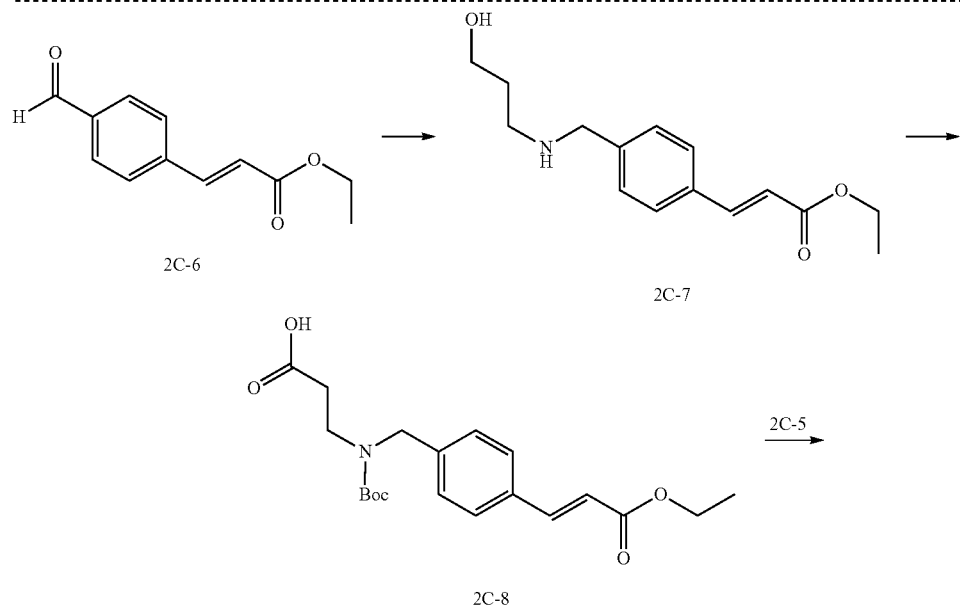
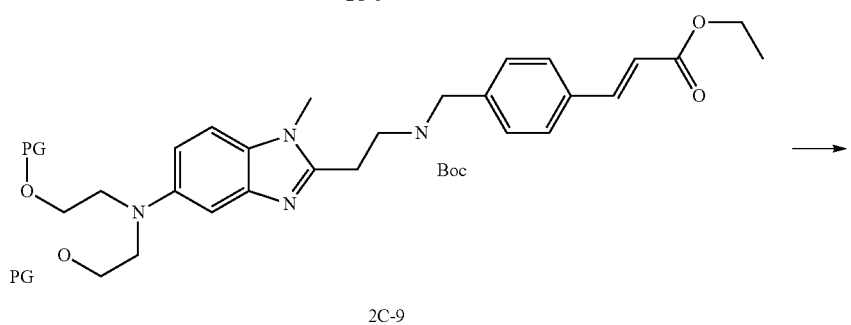
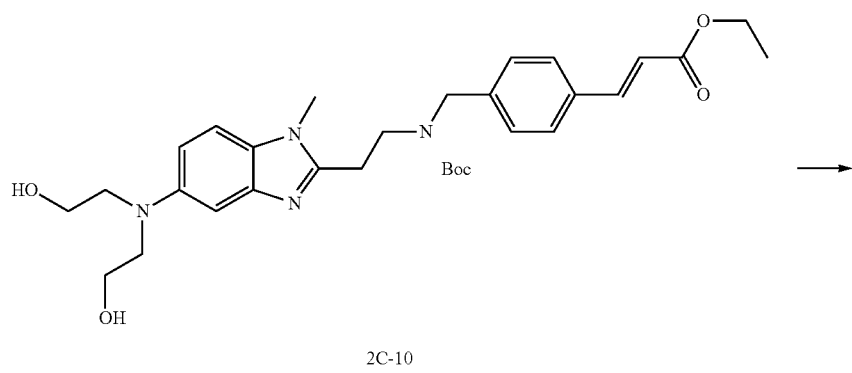

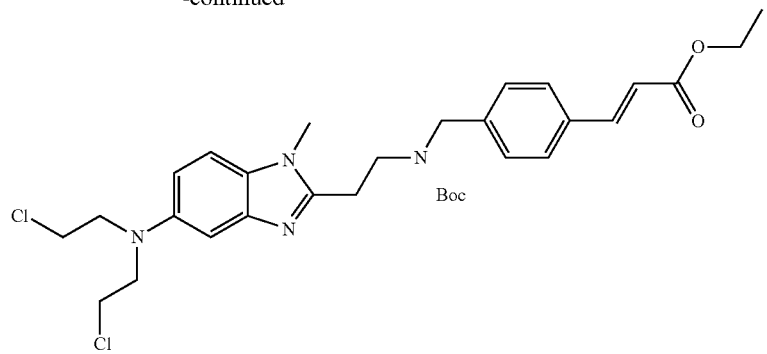

CY-102-1

The commercially available starting material 2C-1 (CAS#: 364-76-1) can react with oxirane to easily afford intermediate 2C-2. The OH group of intermediate (2C-2) can be protected by a protecting group (-PG) to form the intermediate (2C-3). After that 2C-3 can react with $NH_2CH_3$ to afford intermediate 2C-4, which can be reduced for example by $Fe/NH_4Cl$, Fe/HCl or $Zn/FeSO_4$, to an amino-substituted intermediate (2C-5). At the same time, the commercially available starting material 2C-6 can be converted to the intermediate 2C-7 and then the Boc protected 2C-8 by standard organic reactions, which will react with 2C-5 to form the benzimidazole intermediate 2C-9. Next, the OH group of 2C-9 will undergo the deprotection reaction to yield intermediate 2C-10, which can be subsequently converted to CY-102-I with high yield by reaction with a chlorinating reagent such as thionyl chloride or phosphorus pentachloride.

The preferred method to prepare CY-102 as shown in Scheme 2D.

Scheme 2D

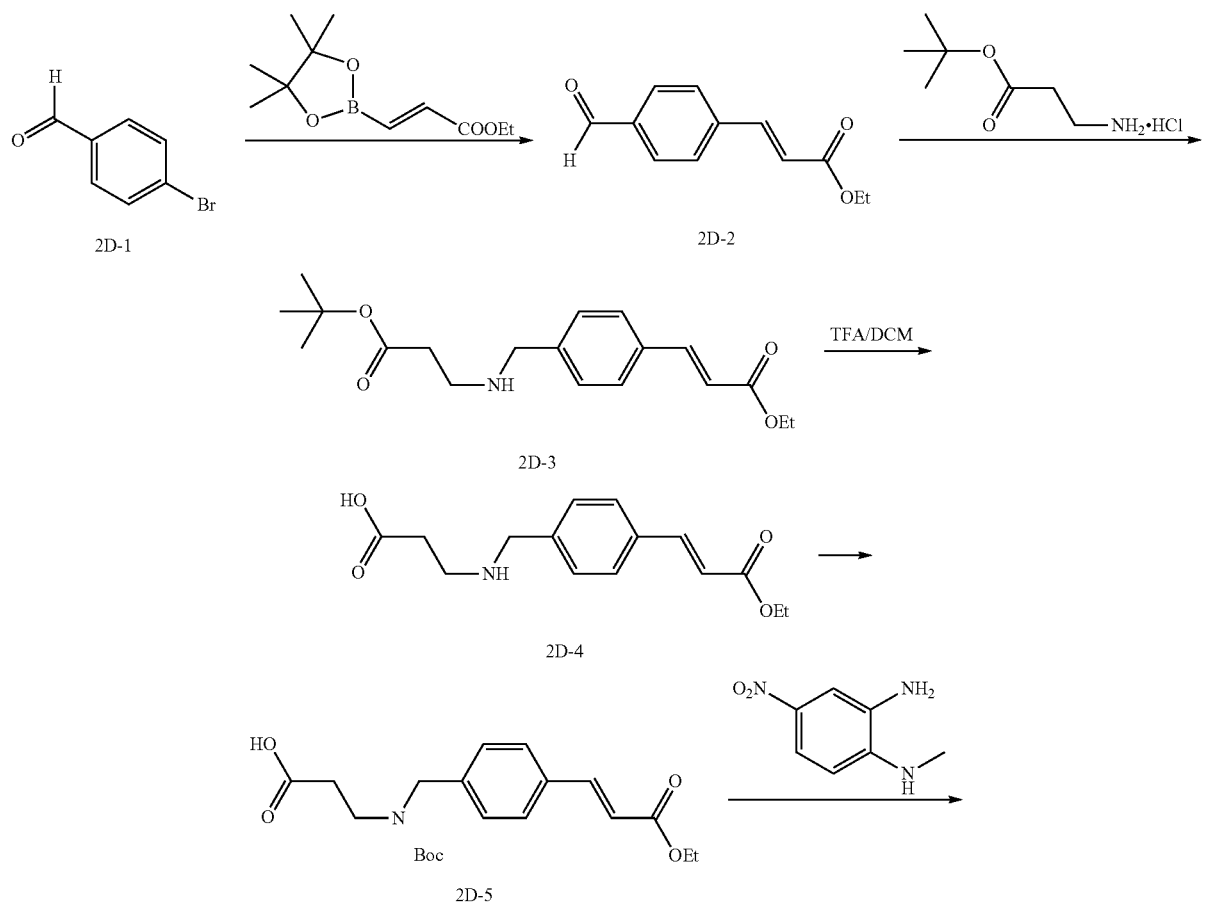

-continued
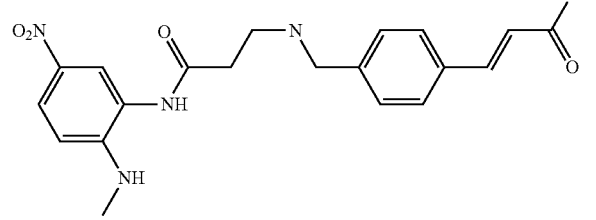
2D-6
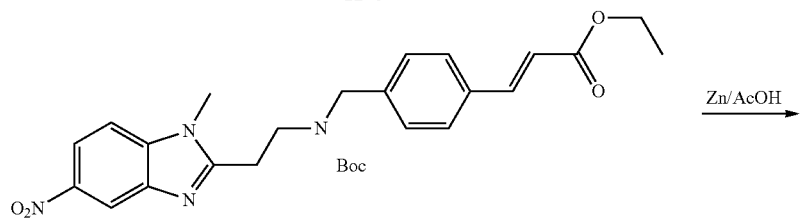
2D-7
Zn/AcOH →
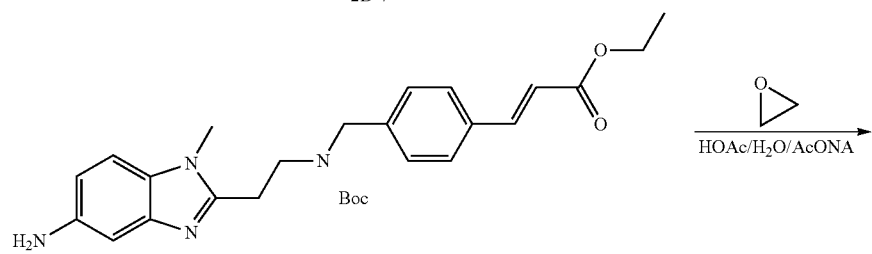
2D-8
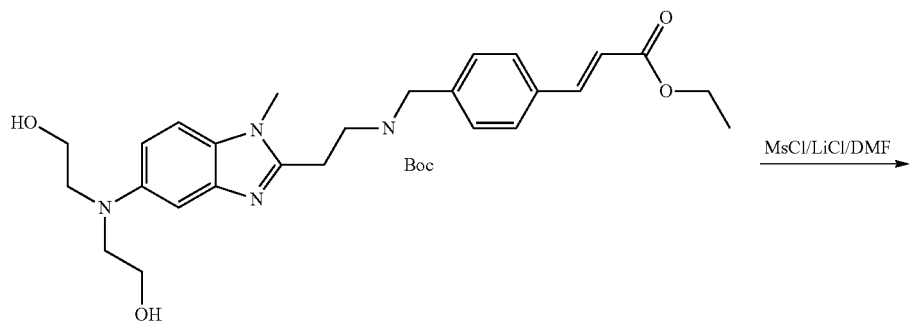
2D-9
MsCl/LiCl/DMF →
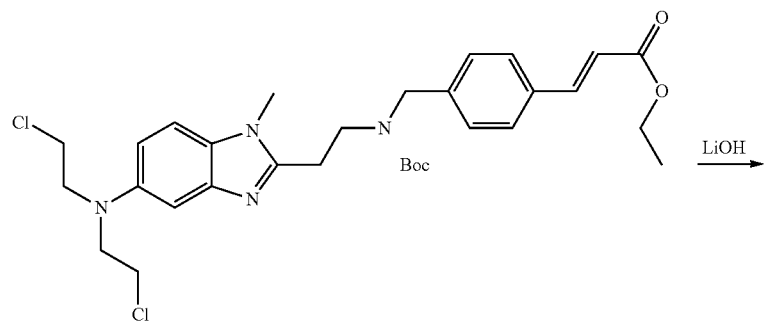
2D-10
LiOH →

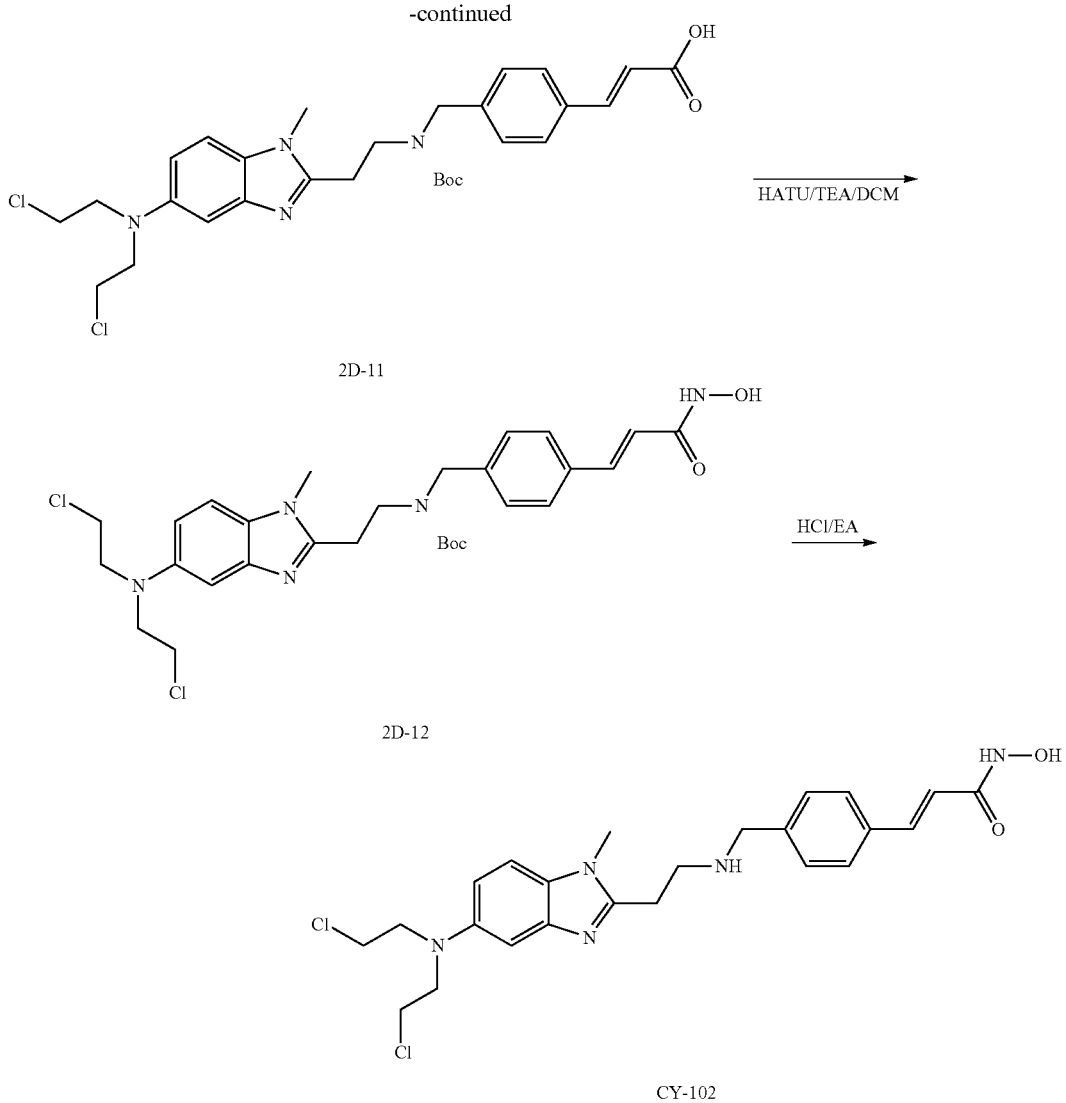

The commercially available starting material 2D-1 (4-bromobenzaldehyde) is converted to cinnamic intermediate 2D-2. After that 2D-2 can react with tert-butyl 3-aminopropanoate to form 2D-3, which can be converted to carboxylic acid intermediate 2D-4 with an appropriate reagent, such as for example, trifluoro acetic acid. The Boc protection of amine of 2D-4 will lead to intermediate 2D-5, which will react with N1-methyl-4-nitrobenzene-1,2-diamine (CAS#: 41939-61-1) to form intermediate 2D-6 followed by a cyclization reaction to form benzimidazole intermediate 2D-7. Intermediate 2D-7 can be reduced for example by Zn/AcOH, Fe/NH$_4$Cl, Fe/HCl or Zn/FeSO$_4$, to an amino-substituted intermediate (2D-8), which can react with oxirane to easily afford intermediate (2D-9). 2D-9 can be converted to intermediate 2D-10 with high yield by reaction with a chlorinating reagent such as thionyl chloride, MsCl/LiCl, or phosphorus pentachloride. The hydrolysis of 2D-10 e.g in LiOH will afford the carboxylic acid intermediate 2D-11, which can couple with NH$_2$OH at the presence of appropriate coupling reagents such as HATU/TEA/DCM to form intermediate 2D-12. Finally, the de-Boc of 2D-12 will lead to the target molecule of CY-102.

EXAMPLES

The invention is illustrated by the following non-limiting examples.

Where NMR data are presented, $^1$H spectra were obtained on either a Varian VXR-200 (200 MHz, $^1$H), Varian Gemini-300 (300 MHz) or XL400 (400 MHz) and are reported as ppm down field from Me$_4$Si with number of protons, multiplicities, and coupling constants in Hertz indicated parenthetically. Where HPLC data are presented, analyses were performed using an Agilent 1100 system. Where LC/MS data are presented, analyses were performed using an Agilent 6210 TOF LC/MS or an Applied Biosystems API-100 mass spectrometer and Shimadzu SCL-10A LC column: Altech platinum C18, 3 micron, 33 mm×7 mm ID; Samples were eluted using a linear gradient of 0-100% acetonitrile/pH4.50, 200 mM NH$_4$ acetate over 10 minutes with a flow rate of 3.0 mL/min. Chromatograms were generated over the range 240-400 nm using a diode array detector.

In the following examples:
DCM=dichloromethane
Boc=tert-butyloxycarbonyl

HATU=O-(7-azabenzotriazol-1-yl)-N,N,N',N'-tetramethyluronium hexafluorophosphate
TEA=triethanolamine
MsCl=methanesulfonyl chloride
DMF=dimethyl fluoride
THF=tetrahydrofuran
EA=ethyl acetate
Example 1: Preparation of CY-102
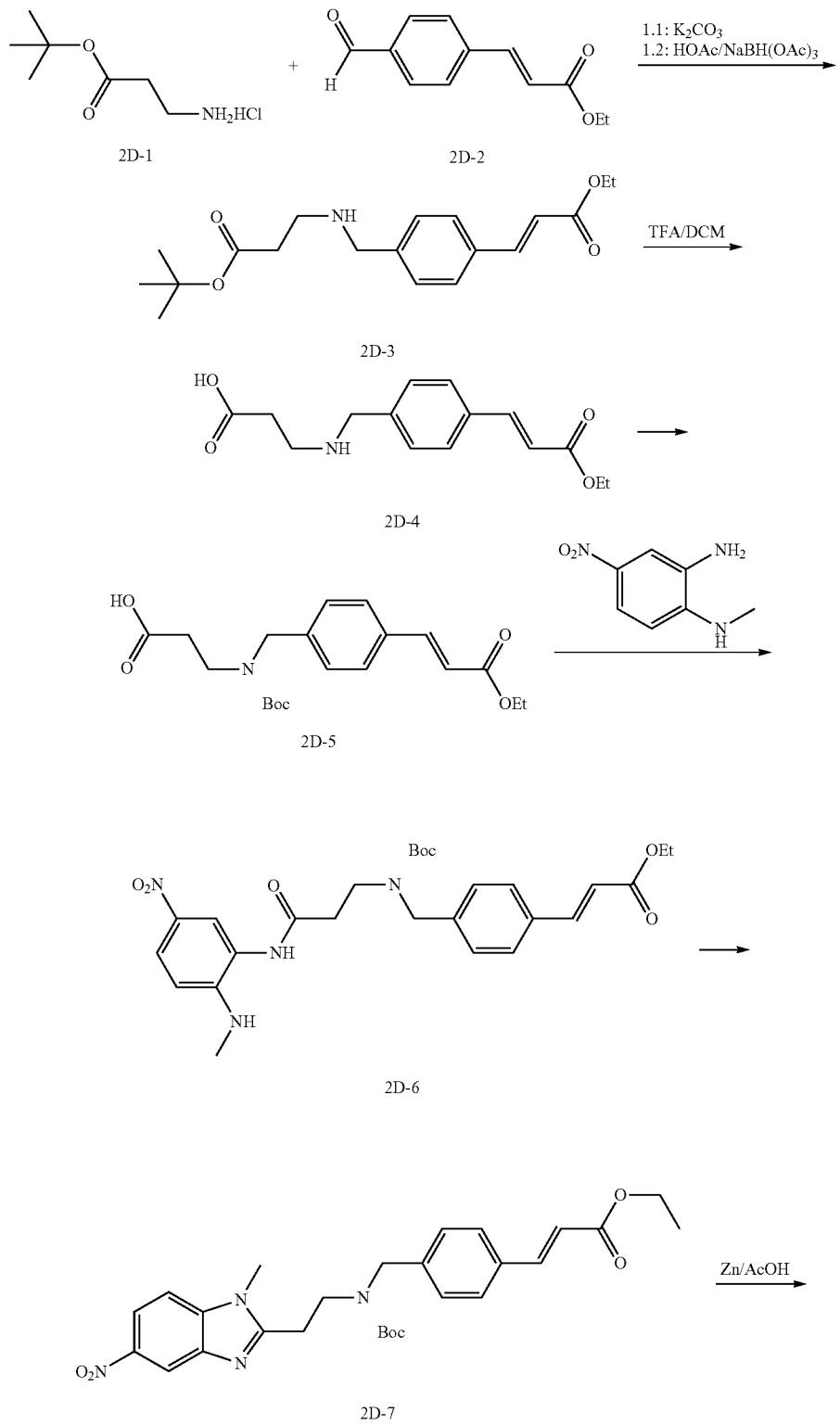

-continued
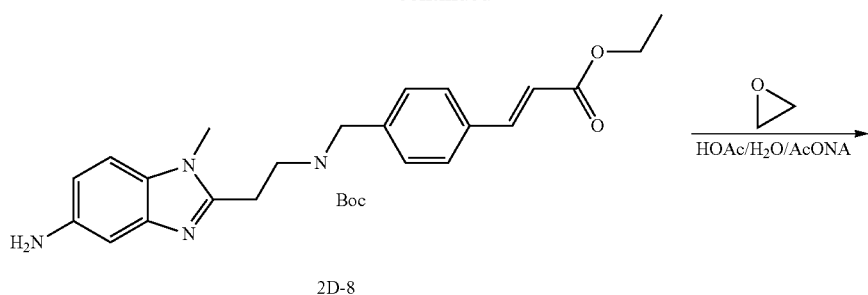
2D-8
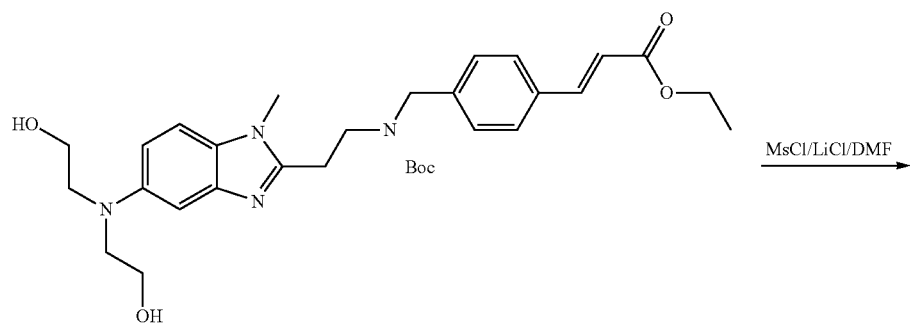
2D-9
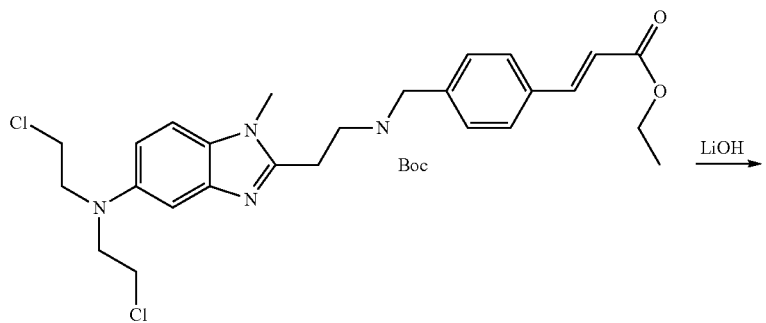
2D-10
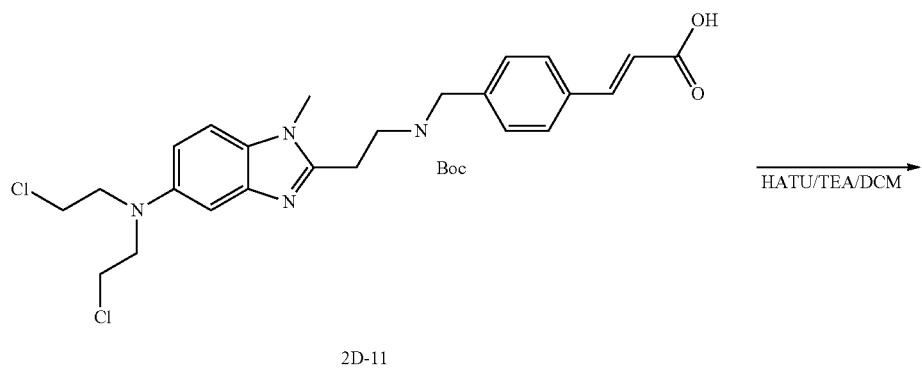
2D-11

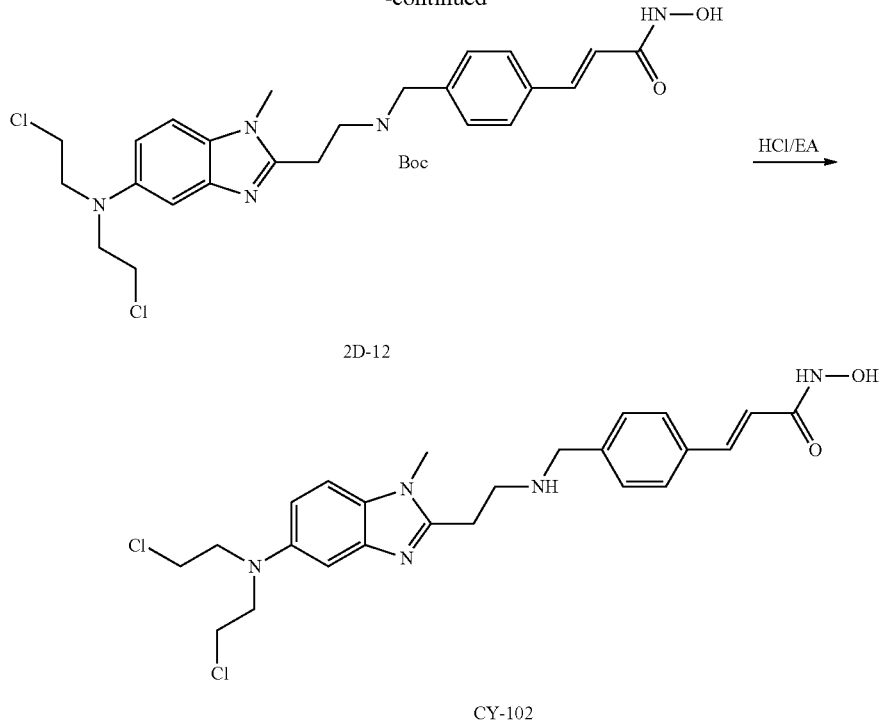

1.1: General Procedure for Preparation of 2D-3:

A mixture of 2D-1 (5.8 g, 31.8 mmol) and K$_2$CO$_3$ (13.2 g, 95.6 mmol) in 1,2-dichloroethane (150 mL) was stirred for 20 mins and filtered. To the filtrate was added 2D-2 (5 g, 24.51 mmol), and then NaBH(OAc)$_3$ (6.24 g, 29.4 mmol) was added in portions. The resulting mixture was stirred at r.t. overnight. The mixture was quenched with water and extracted with DCM. The organic phases were dried and concentrated. The residue was re-crystallized by DCM to give the product 2D-3 (4.0 g, yield 49.2%), as a white solid. HNMR-Analysis: $^1$H NMR (CDCl3) δ: 7.67 (d, J=16.04 Hz, 1H), 7.49 (d, J=7.43 Hz, 2H), 7.35 (d, J=7.43 Hz, 2H), 6.42 (d, J=16.04 Hz, 1H), 4.27 (q, J=6.91 Hz, 2H), 3.84 (s, 3H), 2.87 (t, J=5.87 Hz, 3H), 2.48 (t, J=6.06 Hz, 3H), 1.44 (s, 11H), 1.34 (t, J=7.04 Hz, 3H).

1.2: General Procedure for Preparation of 2D-4:

To a suspension of 2D-3 (25.0 g, 75.1 mmol) in DCM (300 mL) was added TFA (30 mL) and the mixture was stirred at r.t. overnight. The mixture was concentrated, the residue was dissolved in DCM, adjusted to pH=7 with NaOH solution, the mixture was concentrated. The residue was dissolved in DCM and MeOH, then filtered and the filtrate was concentrated to give the crude product 2D-4 (20.0 g, yield 96.2%). HNMR-Analysis: $^1$H NMR (DMSO-d$_6$) δ: 1.23 (t, J=7.04 Hz, 3H), 2.67 (t, J=7.43 Hz, 2H), 3.01-3.12 (m, 2H), 4.16 (d, J=7.04 Hz, 4H), 6.67 (d, J=16.04 Hz, 1H), 7.53 (d, J=7.83 Hz, 2H), 7.63 (d, J=16.04 Hz, 1H), 7.77 (d, J=8.22 Hz, 2H), 9.13 (brs., 2H).

1.3: General Procedure for Preparation of 2D-5:

A mixture of 2D-4 (20 g, 72.2 mmol) and Boc$_2$O (31.5 g, 144.4 mmol) in 1,4-dioxane (250 mL) was heated to reflux for 5 hrs. The mixture was concentrated and the residue was purified by column flash to give 2D-5 (22.1 g, yield 81.2%) as a white solid. HNMR-Analysis: $^1$H NMR (CDCl3) δ: 1.33 (t, J=7.24 Hz, 3H), 1.46 (brs., 9H), 2.60 (brs., 2H), 3.48 (brs., 2H), 4.26 (q, J=7.17 Hz, 2H), 4.47 (br. s., 2H), 6.41 (d, J=16.04 Hz, 1H), 7.23 (d, J=6.26 Hz, 2H), 7.48 (d, J=8.22 Hz, 2H), 7.66 (d, J=16.04 Hz, 1H).

1.4: General Procedure for Preparation of 2D-6:

To a mixture of compound N$^1$-methyl-4-nitrobenzene-1,2-diamine (41 g, 0.11 mol) and TEA (20.4 g, 0.2 mol) in DCM (1000 mL) was added HATU (45.7 g, 0.12 mol) and 2D-5 (16.1 g, 0.11 mol) at 0° C. and the reaction mixture was stirred at 20° C. for 12 hrs. The reaction mixture was poured into water, washed with water for three times. The organic phase was dried over Na$_2$SO$_4$ and concentrated to give 2D-6 (50 g), as a red oil, which was used directly in the next step without further purification. $^1$HNMR of 2D-6: 1.44 (s, 9H) 1.33 (m, 3H) 2.67 (t, J=6 Hz, 2H) 2.92 (s, 3H) 3.18 (m, 2H) 3.61 (t, J=5.6, 2H) 4.26 (q, J=7.2 Hz, 2H) 4.48 (s, 2H) 6.41 (d, J=16. Hz, 1H) 6.57 (d, J=9.2 Hz, 1H) 7.23 (d, J=7.6, 2H) 7.49 (d, J=8 Hz, 2H) 7.65 (d, J=16. Hz, 1H) 7.98-8.11 (m, 2H).

1.5: General Procedure for Preparation of 2D-7:

a mixture of compound 2D-6 (45 g, crude) in toluene and acetic acid (500 mL) was stirred at 100° C. for 30 mins. The reaction mixture was concentrated to give 2D-7 (50 g), as a red oil, which was used directly in the next step without further purification. $^1$HNMR-Analysis of 2D-7: 1.27 (t, 3H) 1.33 (brs, 9H) 3.05-3.18 (m, 4H) 3.50-3.76 (m, 5H) 4.20 (m, 2H) 4.39 (s., 2H) 6.31 (dd, J=16.04, 2.35 Hz, 1H) 7.15-7.34 (m, 5H) 7.48-7.60 (dd, J=16, 3.2 Hz, 1H) 8.13 (d, J=4.4 Hz, 1H) 8.52 (s, 1H)

1.6: General Procedure for Preparation of 2D-8:

To a mixture of compound 2D-7 (50 g, crude) and AcOH (20 mL) in DCM (1000 mL) was added Zn (15 g, 0.23 mol) at 0° C. and the reaction mixture was stirred at 20° C. for 1 h. The reaction mixture was filtered; the filtrate was concentrated to give the crude product (80 g) as red oil which was used to next step without further purification. $^1$HNMR-Analysis of 2D-8: 1.39-1.50 (m, 9H) 3.11 (q, J=7.30 Hz, 3H) 3.38 (br. s., 2H) 3.67 (d, J=11.74 Hz, 3H) 4.22-4.38 (m, 4H)

6.36 (d, J=16.04 Hz, 1H) 6.74 (d, J=8.61 Hz, 1H) 6.99-7.20 (m, 3H) 7.22 (s, 1H) 7.33 (d, J=6.65 Hz, 2H) 7.56 (d, J=16.04 Hz, 1H).

1.7: General Procedure for Preparation of 2D-9:

a mixture of compound 2D-8 (80 g, crude) and ethylene oxide (80 mL) in water (1000 mL) and acetic acid (20 mL) was stirred at 23° C. for 5 hrs. The reaction mixture was concentrated to give 2D-9 (63 g), as a red oil, which was used directly in the next step without further purification. $^1$HNMR (MeOD 400 MHz): 1.30 (m, 12H) 3.22 (br. s., 2H) 3.50 (d, J=4.8, 3H) 3.563 (q, 1H) 3.67 (m, 10H) 4.23 (q, 2H) 6.43 (d, 2H) 6.38 (d, J=16, 1H) 6.91 (d, J=8.4, 2H) 7.22 (t, 2H) 7.29 (d, 2H) 7.33 (d, J=8 Hz, 2H) 7.44 (q, 2H) 7.60 (t, 1H).

1.8: General Procedure for Preparation of 2D-10:

to a mixture of compound 2D-9 (70 g, crude) and TEA (20.4 g, 0.2 mol) in DCM (1000 mL) was added MsCl (13.74 g, 0.12 mol) at 0° C. and the reaction mixture was stirred at 20° C. for 1 h. The reaction mixture was poured into water, washed with water three times. The organic phase was dried over $Na_2SO_4$ and concentrated to give the crude product (100 g). The crude product was dissolved in DMF (500 mL) and LiCl (16.8 g, 0.4 mol) and the resulting mixture was stirred at 100° C. for 2 hrs. The mixture was concentrated and purified by silica gel chromatography to give 2D-10 (18 g). $^1$HNMR (DMSO 400 MHz): 1.25 (m, 12H) 3.03 (br. s., 2H) 3.51 (m, 2H) 3.58-3.69 (m, 10H) 4.17 (q, J=7.6 Hz, 2H) 4.45 (br. s., 2H) 6.58 (d, J=16 Hz, 1H) 6.8 (t, 1H) 6.9 (br.s, 1H) 7.25 (d, J=8, 1H) 7.33 (d, J=9.2, 1H) 7.60 (d, J=16, 1H) 7.66 (d, J=7.2, 2H).

1.9: General Procedure for Preparation of 2D-11:

A mixture of compound 2D-10 (36 g, 59.6 mmol) and LiOH $H_2O$ (3.78 g, 88 mmol) in a mixture of THF and water (600 mL) was stirred at 23° C. for 5 hrs. The reaction mixture was acidified with HCl (1M) to pH=7 and the mixture was filtered. The solid was collected to give 2D-11 (20 g, yield: 59%), as a white solid, which was used directly in the next step without further purification.

1.10: General Procedure for Preparation of 2D-12:

To a mixture of 2D-11 (16.4 g, 28.52 mmol) and TEA (15.0 g, 0.147 mol) in DCM (500 mL) was added HATU (16.8 g, 44 mmol) and $NH_2OH$—HCl (5.16 g, 73.7 mmol) in turn at 20° C. The reaction mixture was stirred at 20° C. for 5 hrs. The mixture was poured into water, diluted with DCM, washed with water for three times. The organic phase was dried over $Na_2SO_4$ and concentrated to give the crude product. The crude product was purified with prep-HPLC to give 2D-12 (7 g, yield: 42%) as white solid.

1.11: General Procedure for Preparation of CY-102:

a mixture of compound 2D-12 (7 g, 11.86 mmol) and HCl/EA (50 mL) in DCM (100 mL) was stirred at 23° C. for 2 hrs. The reaction mixture was concentrated to give CY-102 (5.875 g, yield: 95%) as a yellow powder. $^1$HNMR (MeOD 400 MHz): 3.73 (m, 8H) 3.87 (m, 4H) 4.04 (s, 3H) 4.38 (s, 2H) 6.50 (d, J=16 Hz, 1H) 6.88 (d, J=2 Hz, 1H) 7.18 (dd, J=9.2, 2 Hz, 1H) 7.50 (d, J=16 Hz, 1H) 7.68 (m, 5H). m/z (MH$^+$) is 490.

Example 2: Inhibition of Histone Deacetylase Enzymatic Activity

The following assay protocol is used to assess the inhibitory activity of the compounds of the invention against the HDAC enzymes (Hela Nuclear Extract assay):

Buffer: 25 mM HEPES, pH 8.0, 137 mM NaCl, 2.7 mM KCl, 1 mM $MgCl_2$

Subtrate: Fluor-de-Lys substrate (Biomol, Cat. # KI-104) in a 50 mM stock solution in DMSO.

Enzyme stock solution: 4 µg/mL enzyme in buffer.

To begin the assay, test compounds (2 µl in DMSO diluted to 13 µl in buffer for transfer to the assay plate) are pre-incubated with enzyme (20 µl of 4 µg/mL stock solution) for 10 minutes at room temperature in 35 µl pre-incubation volume. The reaction is started by bringing the temperature to 37° C. and adding 15 µl substrate. Total reaction volume is 50 µl. The reaction is stopped after 20 minutes by adding 50 µl developer, prepared as directed by Biomol (Fluor-de-Lys developer, Cat. # KI-105). Assay plate is incubated in the dark for 10 minutes at room temperature before reading ($\lambda_{Ex}$=360 nm, $\lambda_{Em}$=470 nm, Cutoff filter at 435 nm). The HDAC inhibitors SAHA and TSA are used as reference compounds. Such assays, carried out with a range of doses of test compounds, allow the determination of an approximate $IC_{50}$ value.

As an example, the following table shows the results obtained for CY-102 and Bendamustine. In the HDAC (nucleare extract) assay, CY-102 is about 10-fold more potent than the FDA approved HDAC inhibitor SAHA.

| HDAC | CY-102 | SAHA | Trichostatin A | Bendamustinie |
|---|---|---|---|---|
| $IC_{50}$ (Nuclear Extract) | 3.5 nM | 26.4 nM | 2.1 nM | N/A* |

*No HDAC activity up to highest testing concentration of 10 µM

Example 3: Molecular Docketing Study

Computer modeling with the MOE program (Chemical Computer Group, Canada) was used to assess the interaction between CY-102 and HDAC8. The result (not shown) indicates that CY-102 tightly binds to HDAC8 at its catalytic center, which is consistent with the existing data showing that CY-102 is a strong HDAC inhibitor.

Example 4: Water Solubility

To measure water solubility, to approximately 10 mg of a sample in a tube-stoppered 10 mL graduated cylinder, increasing volumes of distilled water at room temperature were added according to the steps shown in the table below:

| Water Solubility | step 1 | step 2 | step 3 | step 4 | step 5 |
|---|---|---|---|---|---|
| Total volume of H$_2$O added (mL) | 1 | 2 | 4 | 5 | 10 |
| Approximate solubility (mg/mL) | 10 | 5 | 2.5 | 2 | 1 |

After each addition of water to give the indicated total volume, the mixture was vortexed or sonicated for 1 min and was visually inspected for any undissolved parts of the sample. If, after a total of 10 mL of water had been added (step 5), the sample or parts of it remained undissolved, the contents of the measuring cylinder was transferred to a 100 mL measuring cylinder which was then filled up with water up to 100 mL (20 ml, 25 ml, 50 ml, 100 ml) and shaken. The approximate solubility was given in the table under that volume of added water in which complete dissolution of the sample occurred. If the substance was still apparently insoluble, further dilution was undertaken to ascertain whether the column elution or the flask solubility method should be used.

Using the method described above, water solubility of CY-102 was determined to be greater than about 20 mg/mL, which is at least about 200-fold more water soluble than NL-101.

Example 5: General In Vitro Anti-Proliferation Assay

Cell antiproliferation assay is performed by using the PerkinElmer ATPlite™ Luminescence Assay System. Briefly, the various test cancer cell lines are plated at a density of about 1×10$^4$ cells per well in Costar 96-well plates, and are incubated with different concentrations of compounds for about 72 hours in medium supplemented with 5% FBS. One lyophilized substrate solution vial is then reconstituted by adding 5 mL of substrate buffer solution, and is agitated gently until the solution is homogeneous. About 50 µL of mammalian cell lysis solution is added to 100 µL of cell suspension per well of a microplate, and the plate is shaken for about five minutes in an orbital shaker at ~700 rpm. This procedure is used to lyse the cells and to stabilize the ATP. Next, 50 µL substrate solution is added to the wells and microplate is shaken for five minutes in an orbital shaker at ~700 rpm. Finally, the luminescence is measured by a PerkinElmer TopCount® Microplate Scintillation Counter. Such assays, carried out with a range of doses of test compounds, allow the determination of the cellular anti-antiproliferative IC$_{50}$ of the compounds of the present invention.

Example 6: In Vitro Assay: NCI-60 DTP Human Tumor Cell Line Screen at 10 µM

NL-101 and CY-102 was sent to U.S. National Cancer Institute (NCI) for NCI 60-cell line screening using a single compound dose (10 µM).

The human tumor cell lines of the cancer screening panel were grown in RPMI 1640 medium containing 5% fetal bovine serum (5% FBS) and 2 mM L-glutamine. For a typical screening experiment, cells were inoculated into 96-well microtiter plates in 100 µL, at plating densities ranging from 5,000 to 40,000 cells/well depending on the doubling time of individual cell lines. After cell inoculation, the microtiter plates were incubated at 37° C., 5% CO$_2$, 95% air, and 100% relative humidity for 24 h prior to addition of experimental compounds. After 24 hr, two plates of each cell line were fixed in situ with TCA, to represent a measurement of the cell population for each cell line at the time of drug addition (Tz). Experimental drugs were solubilized in dimethyl sulfoxide at 400-fold the desired final maximum test concentration and stored frozen prior to use. At the time of drug addition, an aliquot of frozen concentrate was thawed and diluted to twice the desired final maximum test concentration with complete medium containing 50 µg/ml gentamicin. Aliquots of 100 µL of these different drug dilutions were added to the appropriate microtiter wells already containing 100 µL of medium, resulting in the required final drug concentrations.

Following drug addition, the plates were incubated for an additional 48 hrs at 37° C., 5% CO$_2$, 95% air, and 100% relative humidity. For adherent cells, the assay was terminated by the addition of cold TCA. Cells were then fixed in situ by the gentle addition of 50 µL of cold 50% (w/v) TCA (final concentration, 10% TCA) and incubated for 60 minutes at 4° C. The supernatant was discarded, and the plates were washed five times with tap water and air dried. Sulforhodamine B (SRB) solution (100 µL) at 0.4% (w/v) in 1% acetic acid was added to each well, and plates were incubated for 10 minutes at room temperature. After staining, unbound dye was removed by washing five times with 1% acetic acid and the plates were air dried. Bound stain was subsequently solubilized with 10 mM trizma base, and the absorbance was read on an automated plate reader at a wavelength of 515 nm. For suspension cells, the methodology was the same except that the assay was terminated by fixing settled cells at the bottom of the wells by gently adding 50 µL of 80% TCA (final concentration, 16% TCA).

Using the seven absorbance measurements [time zero, (Tz), control growth, (C), and test growth in the presence of drug at the 10 µM concentration levels (Ti)], percentage growth was calculated at each of the drug concentrations levels. Percentage growth inhibition was calculated as: [(Ti−Tz)/(C−Tz)]×100 for which Ti>/=Tz or [(Ti−Tz)/Tz]×100 for which Ti<Tz.

The results of the assays for CY-102 and NL-101 are summarized in the table below.

| Cell Panel | Cell Line | NL-101 Growth % | CY-102 Growth % |
|---|---|---|---|
| Leukemia | HL-60(TB) | 18.98 | −10.34 |
| Leukemia | K-562 | 31.63 | 1.07 |
| Leukemia | MOLT-4 | 18.01 | 2.17 |
| Leukemia | CCRF-CEM | 17.16 | |
| Leukemia | RPMI-8226 | 49.23 | 2.28 |
| Leukemia | SR | 29.62 | 0.09 |
| NSCLC | A549/ATCC | 43.54 | −32.69 |
| NSCLC | EKVX | 92.48 | |
| NSCLC | HOP-62 | 13.56 | −30.02 |
| NSCLC | HOP-92 | 22.07 | −35.89 |
| NSCLC | NCI-H226 | 60.27 | −20.77 |
| NSCLC | NCI-H23 | 30.14 | −6.76 |
| NSCLC | NCI-H322M | 75.30 | −15.30 |
| NSCLC | NCI-H460 | 25.56 | 2.61 |
| NSCLC | NCI-H522 | −5.90 | |
| Colon Cancer | COLO 205 | 54.36 | −81.34 |
| Colon Cancer | HCC-2998 | 86.98 | −80.55 |
| Colon Cancer | HCT-116 | 23.73 | −1.84 |
| Colon Cancer | HCT-15 | 76.48 | 9.96 |
| Colon Cancer | HT29 | 37.10 | −50.67 |
| Colon Cancer | KM12 | 65.79 | −78.14 |
| Colon Cancer | SW-620 | 30.40 | 2.33 |
| CNS Cancer (Glioma) | SF-268 | 10.27 | −31.46 |

63

-continued

| Cell Panel | Cell Line | NL-101 Growth % | CY-102 Growth % |
|---|---|---|---|
| CNS Cancer (Glioma) | SF-295 | 43.95 | -53.87 |
| CNS Cancer (Glioma) | SF-539 | 23.72 | |
| CNS Cancer (Glioma) | SNB-19 | 55.62 | -10.81 |
| CNS Cancer (Glioma) | SNB-75 | 19.79 | -48.45 |
| CNS Cancer (Glioma) | U251 | 35.03 | -39.66 |
| Melanoma | LOX IMVI | -23.43 | -26.41 |
| Melanoma | MALME-3M | 28.59 | -64.17 |
| Melanoma | M14 | 39.93 | -76.75 |
| Melanoma | MDA-MB-435 | 49.07 | -73.24 |
| Melanoma | SK-MEL-2 | 37.31 | -21.36 |
| Melanoma | SK-MEL-28 | 59.32 | -21.36 |
| Melanoma | SK-MEL-5 | -6.55 | -79.31 |
| Melanoma | UACC-257 | 33.75 | -36.39 |
| Melanoma | UACC-62 | 12.99 | -69.24 |
| Ovarian Cancer | IGROV1 | 55.99 | -14.43 |
| Ovarian Cancer | OVCAR-3 | 50.40 | -55.02 |
| Ovarian Cancer | OVCAR-4 | 68.52 | -19.00 |
| Ovarian Cancer | OVCAR-5 | 66.28 | -3.75 |
| Ovarian Cancer | OVCAR-8 | 32.65 | -26.88 |
| Ovarian Cancer | NCI/ADR-RES | 77.80 | 17.78 |
| Ovarian Cancer | SK-OV-3 | 34.40 | -41.53 |
| Renal Cancer | 786-0 | 19.82 | -30.40 |
| Renal Cancer | A498 | 49.70 | -81.56 |
| Renal Cancer | ACHN | 14.30 | -19.97 |
| Renal Cancer | CAKI-1 | 27.64 | -25.49 |
| Renal Cancer | RXF 393 | 5.95 | -35.55 |
| Renal Cancer | SN12C | 17.91 | -1.53 |
| Renal Cancer | TK-10 | 48.48 | -28.81 |
| Renal Cancer | UO-31 | 63.69 | -9.19 |
| Prostate Cancer | PC-3 | 51.40 | -1.86 |
| Prostate Cancer | DU-145 | 18.47 | -16.06 |
| Breast Cancer | MCF7 | 37.24 | -15.28 |
| Breast Cancer | MDA-MB-231 | 72.24 | -35.33 |
| Breast Cancer | HS 578T | 24.01 | 8.17 |
| Breast Cancer | BT-549 | 79.21 | -33.26 |
| Breast Cancer | T-47D | -16.57 | -27.48 |
| Breast Cancer | MDA-MB-468 | -34.68 | -21.52 |
| | Median | 36.35 | -28.5 |

The results show that, when NL-101 and CY-102 were tested side-by-side at a single dose of about 10 μM in 60 cancer cell lines of leukemia, multiple myeloma, non small cell lung cancer (NSCLC), breast cancer, melanoma, ovarian cancer, prostate cancer, colon cancer, CNS cancer, and renal cancer, the mean growth percent of NL-101 in the 60 cancer cell lines is 36%. In contrast, the mean growth percent of CY-102 is -28%. Based on this data, the average celluar $IC_{50}$ of CY-102 in the 60 cancer cell lines is expected to be at least 10-fold more potent than the $IC_{50}$ of NL-101, which on average is about 2 μM.

More impressively, CY-102 was found to be particularly potent in several solid tumor cell lines, such as breast cancer (e.g., MCF7, MDA-MB-231, BT-549, T-47D, MDA-MB-468), colon cancer (e.g., COLO 205, HCC-2998, HT29, SW-620), renal (e.g., A498), and particularly in melanoma (e.g., MALME-3M, M14, MDA-MB-435, SK-MEL-5, UACC-62), suggesting that CY-102 may have wide applications in treating solid tumors. On the other hand, NL-101 appears to be more effective against hematological cancers such as leukemia, lymphoma, and multiple myeloma.

Example 7: In Vitro hERG Assay

The hERG (Human Ether-á-go-go-Related-Gene) assay was used to assess cardiotoxic effects of drug candidates, CY-102. Results (not shown) demonstrated that CY-102 has much lower (about 5-10 fold less) cardiotoxicity compared to that of NL-101.

Example 8: In Vivo Xenograft Studies

As compared to NL-101, CY-102 is much more potent in in vitro celluar antiproliferative assay (about 10-fold more potent, see above), shows much less in vitro cardiotoxicity in the hERG assay (about 5-10 fold less, see above), and is significantly more (>200 fold) soluble in water (see above). Thus, CY-102 is selected for in vivo studies in the xenograft models of Breast cancer (MBA-MD-231, MX-1), SCLC (H69, H526), Sarcoma (HT-1080, SJSA-1), Melanoma (MDA-MB-435, SK-MEL-5), and NSCLC (H1975, HCC827, H3255, PC-9).

Athymic nude mice (CD-1 nu/nu) or SCID mice are obtained at age 6-8 weeks from vendors and acclimated for a minimum 7-day period. The cancer cells are then implanted into the nude mice. Depending on the specific tumor type, tumors are typically detectable about two weeks following implantation. When tumor sizes reach ~100-200 mm³, the animals with appreciable tumor size and shape are randomly assigned into groups of 8 mice each, including one vehicle control group and treatment groups. Dosing varies depending on the purpose and length of each study, which typically proceeds for about 3-4 weeks. Tumor sizes and body weight are typically measured three times per week. In addition to the determination of tumor size changes, the last tumor measurement is used to generate the tumor size change ratio (T/C value), a standard metric developed by the National Cancer Institute for xenograft tumor evaluation. In most cases, % T/C values are calculated using the following formula: % T/C=100×ΔT/ΔC if ΔT>0. When tumor regression occurred (ΔT<0), however, the following formula is used: % T/T0=100×ΔT/T0. Values of <42% are considered significant.

The invention claimed is:
1. A compound of Formula (I) or an N-oxide thereof, or a pharmaceutically acceptable salt of said compound of formula (I) or N-oxide thereof:

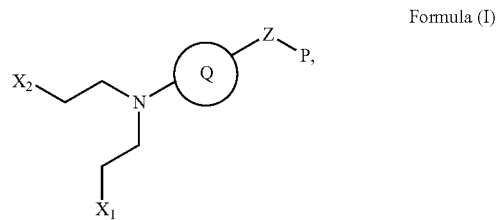

Formula (I)

wherein
Z is $(CR_aR_b)_pN(R_a)(CR_aR_b)_q$;
$X_1$ and $X_2$ are each independently selected from halo and $OSO_2R_c$;
P is

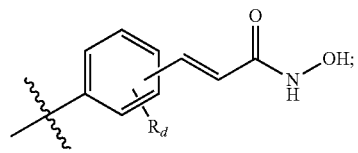

Q is benzimidazolyl, which is optionally substituted with alkyl, alkenyl, alkynyl, cycloalkyl, halo, nitro, oxo, cyano or $OR_e$;

$R_a$, $R_b$, $R_d$ and $R_e$ are each independently selected from H, alkyl, alkenyl and alkynyl;

$R_c$ is selected from alkyl, alkenyl and alkynyl; and p and q are each independently selected from 1, 2, 3 and 4.

2. The compound according to claim 1 or an N-oxide thereof, or a pharmaceutically acceptable salt thereof, wherein p is 1 and q is 2; or p is 2 and q is 1; or p and q are both 2.

3. The compound according to claim 1 or an N-oxide thereof, or a pharmaceutically acceptable salt thereof, wherein Z is $(CH_2)_p NH(CH_2)_q$.

4. The compound according to claim 3 or an N-oxide thereof, or a pharmaceutically acceptable salt thereof, wherein Z is $(CH_2)_2 NH(CH_2)$.

5. The compound according to claim 1 or an N-oxide thereof, or a pharmaceutically acceptable salt thereof, wherein $X_1$ and $X_2$ are each independently selected from chloro, bromo and iodo.

6. The compound according to claim 5 or an N-oxide thereof, or a pharmaceutically acceptable salt thereof, wherein $X_1$ and $X_2$ are both chloro.

7. The compound according to claim 1 or an N-oxide thereof, or a pharmaceutically acceptable salt thereof, wherein Q is benzimidazolyl substituted by one or more alkyl groups.

8. The compound according to claim 7 or an N-oxide thereof, or a pharmaceutically acceptable salt thereof, wherein the compound of Formula (I) is represented by Formula(II):

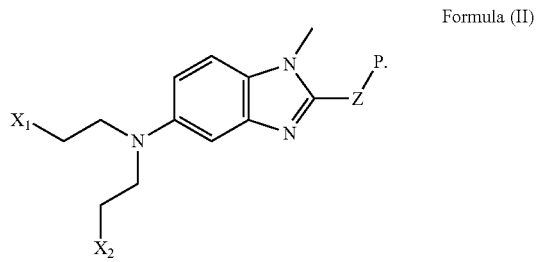

Formula (II)

9. The compound according to claim 8 or an N-oxide thereof, or a pharmaceutically acceptable salt thereof wherein the compound of Formula (I) is represented by Formula (III):

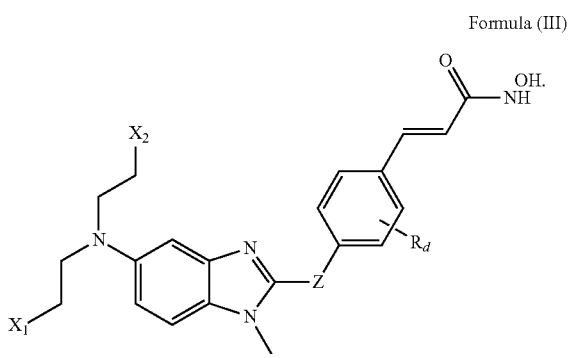

Formula (III)

10. The compound according to claim 9, which is

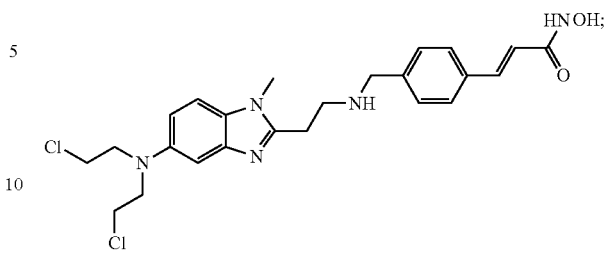

or a pharmaceutically acceptable salt thereof.

11. The compound according to claim 10, which is the hydrochloride salt thereof.

12. A pharmaceutical composition comprising a compound of formula (I) or an N-oxide thereof as defined in claim 1, or a pharmaceutically acceptable salt of said compound of formula (I) or an N-oxide thereof, and a pharmaceutically acceptable diluent or carrier.

13. A combination comprising a compound of formula (I) or an N-oxide thereof as defined in claim 1, or a pharmaceutically acceptable salt of said compound of formula (I) or N-oxide thereof, together with one or more other therapeutic agents.

14. The combination according to claim 13 wherein the one or more other therapeutic agents is selected from: proteasome inhibitors, IMIDs, platinum agents, folate antagonists, CD30 antibodies and conjugates, antibodies or conjugated antibodies to treat haematological malignancies, anti-CD20 antibodies, B-cell receptor antagonists, PI3K antagonists, BTK inhibitors, taxanes, antibodies or conjugated antibodies—to treat ovarian cancer, antibodies to treat multiple myeloma, anthracyclines, nucleoside analogues, purine antagonists, PNP antagonists, Bcr-abl tyrosinekinase blockers, mTor antagonists, Agents influencing the CD40 activation, multi tyrosine kinase antagonists, and bifunctional antibodies.

15. A product containing a compound of formula (I) or an N-oxide thereof as defined in claim 1, or a pharmaceutically acceptable salt of said compound of formula (I) or N-oxide thereof, and one or more other therapeutic agents, as a combined preparation for simultaneous, separate or sequential use in treating a neoplastic disease or an immune disease, wherein said one or more other therapeutic agents is selected from: proteasome inhibitors, IMIDs, platinum agents, folate antagonists, CD30 antibodies and conjugates, antibodies or conjugated antibodies to treat haematological malignancies, anti-CD20 antibodies, B-cell receptor antagonists, PI3K antagonists, BTK inhibitors, taxanes, antibodies or conjugated antibodies to treat ovarian cancer, antibodies to treat multiple myeloma, anthracyclines, nucleoside analogues, purine antagonists, PNP antagonists, Bcr-abl tyrosinekinase blockers, mTor antagonists, Agents influencing the CD40 activation, multi tyrosine kinase antagonists, and bifunctional antibodies.

16. The combination according to claim 13, wherein the one or more other therapeutic agents is selected from: bortezomib, carfilzomib, thalidomide, lenalidomide, pomalidomide, cisplatin, carboplatin, pemetrexed, pralatrexate, brentuximab, vendotin, ofatumumab, rituximab, GA101, ibrutinib, GS1101, IPI145, taxol, paclitaxel, alpha folate receptor monoclonal antibodies, CA125 antibodies, elotuzumab, anti CD38 monoclonal antibodies, doxorubicin, idarubicin, cytarabine, fludarabine, gemcitabine, cytarabine, fludarabine, gemcitabine, forodesine, imatinib, dasatinib, ponatinib, nilotinib, temsirolimus, everolimus, CD40 antagonists, CD40 gene medicines, sorafenib, axitinib, CD19/CD3 bifunctional antibodies, conjugated bifunctional antibodies, and bifunctional antibodies recognizing CD epitopes.

17. The product according to claim 15, wherein said one or more other therapeutic agents is selected from: bortezomib, carfilzomib, thalidomide, lenalidomide, pomalidomide, cisplatin, carboplatin, pemetrexed, pralatrexate, brentuximab, vendotin, ofatumumab, rituximab, GA101, ibrutinib, GS1101, IPI145, taxol, paclitaxel, alpha folate receptor monoclonal antibodies, CA125 antibodies, elotuzumab, anti CD38 monoclonal antibodies, doxorubicin, idarubicin, cytarabine, fludarabine, gemcitabine, cytarabine, fludarabine, gemcitabine, forodesine, imatinib, dasatinib, ponatinib, nilotinib, temsirolimus, everolimus, CD40 antagonists, CD40 gene medicines, sorafenib, axitinib, CD19/CD3 bifunctional antibodies, conjugated bifunctional antibodies, and bifunctional antibodies recognizing CD epitopes.

\* \* \* \* \*

UNITED STATES PATENT AND TRADEMARK OFFICE
CERTIFICATE OF CORRECTION

PATENT NO.        : 10,118,901 B2
APPLICATION NO.   : 14/374995
DATED             : November 6, 2018
INVENTOR(S)       : Yu Chen et al.

Page 1 of 2

It is certified that error appears in the above-identified patent and that said Letters Patent is hereby corrected as shown below:

On the Title Page

In the left column, between existing items (65) and (51), please insert a new item (60):
-- Related U.S. Application Data
(60) Provisional application No. 61/678,064, filed on July 31, 2012; provisional application No. 61/593,459, filed on February 1, 2012. --.

In the Claims

At Column 65, Claim number 9, Line numbers 51-65, replace:

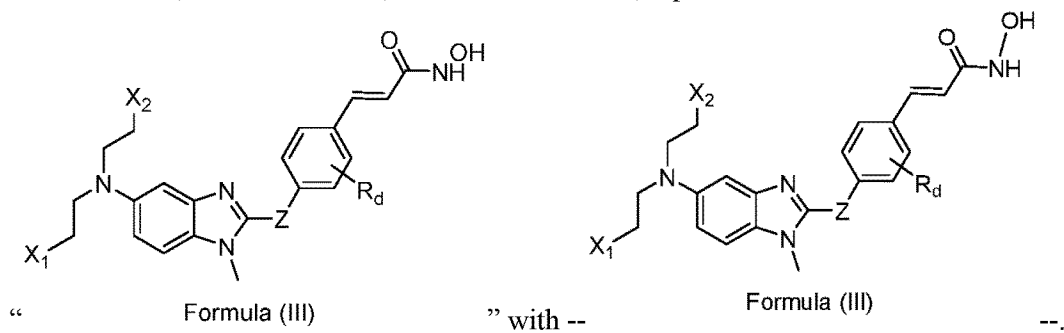

" Formula (III)     " with --     Formula (III)     --.

At Column 66, Claim number 10, Line numbers 4-13, replace:

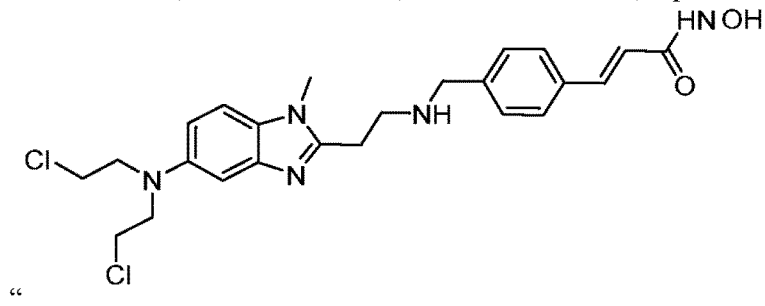

"                   " with

Signed and Sealed this
Twenty-fifth Day of December, 2018

Andrei Iancu
*Director of the United States Patent and Trademark Office*

CERTIFICATE OF CORRECTION (continued)
U.S. Pat. No. 10,118,901 B2

-- 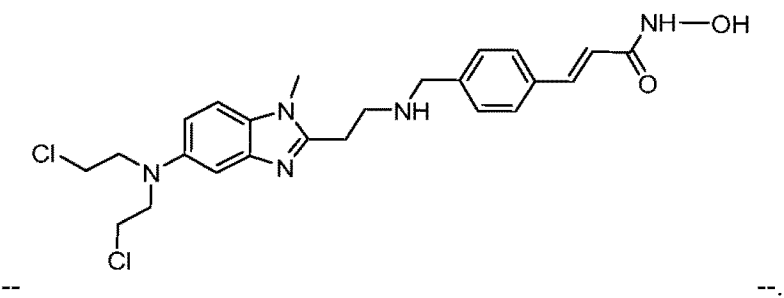 --.